(12) United States Patent
Verkman et al.

(10) Patent No.: US 9,790,218 B2
(45) Date of Patent: Oct. 17, 2017

(54) SMALL MOLECULE ACTIVATORS OF CALCIUM-ACTIVATED CHLORIDE CHANNELS AND METHODS OF USE

(75) Inventors: Alan S. Verkman, San Francisco, CA (US); Wan Namkung, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 49 days.

(21) Appl. No.: 14/237,079

(22) PCT Filed: Aug. 3, 2012

(86) PCT No.: PCT/US2012/049631
§ 371 (c)(1),
(2), (4) Date: Sep. 5, 2014

(87) PCT Pub. No.: WO2013/022793
PCT Pub. Date: Feb. 14, 2013

(65) Prior Publication Data
US 2014/0378510 A1    Dec. 25, 2014

Related U.S. Application Data

(60) Provisional application No. 61/515,555, filed on Aug. 5, 2011.

(51) Int. Cl.
| | |
|---|---|
| *C07D 417/12* | (2006.01) |
| *A61K 31/41* | (2006.01) |
| *A61K 31/426* | (2006.01) |
| *A61K 31/4439* | (2006.01) |
| *C07D 277/46* | (2006.01) |

(52) U.S. Cl.
CPC .......... *C07D 417/12* (2013.01); *A61K 31/41* (2013.01); *A61K 31/426* (2013.01); *A61K 31/4439* (2013.01); *C07D 277/46* (2013.01)

(58) Field of Classification Search
CPC ................................................ C07D 417/12
See application file for complete search history.

(56) References Cited

U.S. PATENT DOCUMENTS

| | | | | |
|---|---|---|---|---|
| 3,549,770 | A | * 12/1970 | Jacob ...................... | A61K 8/46 514/708 |
| 2009/0048313 | A1 | 2/2009 | Dickson, Jr. et al. | |
| 2009/0163476 | A1 | 6/2009 | Milburn et al. | |
| 2010/0168084 | A1 | 7/2010 | Huber et al. | |
| 2011/0015239 | A1 | 1/2011 | Verkman et al. | |
| 2013/0143765 | A1 | 6/2013 | Verkman et al. | |

FOREIGN PATENT DOCUMENTS

| | | |
|---|---|---|
| WO | 2009/079373 A2 | 6/2009 |

OTHER PUBLICATIONS

Chemical Abstracts Registry No. 1217112-67-8, indexed in the Registry file on STN CAS Online Apr. 6, 2010.*
Chemical Abstracts Registry No. 483983-00-2, indexed in the Registry file on STN CAS Online Jan. 31, 2003.*
Chemical Abstracts Registry No. 483982-27-0, indexed in the Registry file on STN CAS Online Jan. 31, 2003.*
National Center for Biotechnology Information. PubChem Substance Database; SID=4136745, Source=ASINEX, http://pubchem.ncbi.nlm.nih.gov/summary/summary.cgi?sid=4136745 (accessed Dec. 14, 2015), deposit date Aug. 10, 2005.*
National Center for Biotechnology Information. PubChem Substance Database; SID=4136646, Source=ASINEX, http://pubchem.ncbi.nlm.nih.gov/summary/summary.cgi?sid=4136646 (accessed Dec. 14, 2015), deposit date Aug. 10, 2005.*
ASINEX website home page back in Jan. 2011, compliments of the Internet Archive Way Back Machine, https://web.archive.org/web/20110105210501/http://www.asinex.com/Libraries.html.*
Handbook of Pharmaceutical Excipients, Fourth Edition, Ed. Raymond C. Rowe, 2003, pp. 219-221.*
Mukherjee et al., Bioorganic & Medicinal Chemistry, 16, 2008, pp. 4138-4149.*
Chemical Abstracts Registry No. 845284-73-3, indexed in the Registry file on STN CAS Online Mar. 11, 2005.*
Chemical Abstracts Registry No. 845284-18-6, indexed in the Registry file on STN CAS Online Mar. 11, 2005.*
Chemical Abstracts Registry No. 845284-83-5, indexed in the Registry file on STN CAS Online Mar. 11, 2005.*
Gabriela Segura, MD, "DMSO: The Real Miracle Solution", http://healthmatrix.net/2011/03/15/dmsotherealmiraclesolution/, dated Mar. 15, 2011, accessed Feb. 23, 2017.*
Boucher, "Airway Surface Dehydration in Cystic Fibrosis: Pathogenesis and Therapy," *Annu. Rev. Med.* 58:157-170, 2007.
Caputo et al., "TMEM16A, A Membrane Protein Associated with Calcium-Dependent Chloride Channel Activity," *Science* 322:590-594, Oct. 24, 2008.
Cheng et al., "Synthesis and Structure—Activity Relationship of Small-Molecule Malonyl Coenzyme A Decarboxylase Inhibitors," *J. Med. Chem.* 49:1517-1525, 2006.
Davis et al., "Potent vasorelaxant activity of the TMEM16A inhibitor T16A$_{inh}$-A01," *British Journal of Pharmacology* 168:773-784, 2013.
De La Fuente et al., "Small-Molecule Screen Identifies Inhibitors of a Human Intestinal Calcium-Activated Chloride Channel," *Mol Pharmacol* 73(3):758-768, 2008.
Donaldson et al., "Sodium Channels and Cystic Fibrosis," *Chest* 132(5):1631-1636, Nov. 2007.
Dutta et al., "Identification and Functional Characterization of TMEM16A, a $Ca^{2+}$-activated $Cl^-$ Channel Activated by Extracellular Nucleotides, in Biliary Epithelium," *The Journal of Biological Chemistry* 286(1):766-776, Jan. 7, 2011.
Eggermont, "Calcium-activated Chloride Channels: (Un)known, (Un)loved?," *Proc Am Thorac Soc* 1:22-27, 2004.
Ferrera et al., "TMEM16A Protein: A New Identity for $Ca^{2+}$-Dependent $Cl^-$ Channels," *Physiology* 25:357-363, 2010.

(Continued)

*Primary Examiner* — Laura L. Stockton
(74) *Attorney, Agent, or Firm* — Seed IP Law Group LLP

(57) ABSTRACT

Provided herein are small molecule activators of calcium-activated chloride channels. These small molecules may be used for treatment of diseases and disorders that are treatable by activating calcium-activated chloride channels, such as cystic fibrosis, disorders related to salivary gland dysfunction (for example, Sjogren's syndrome and dysfunction following radiation injury), dry eye syndrome, and intestinal hypomotility.

8 Claims, 17 Drawing Sheets

(56) References Cited

OTHER PUBLICATIONS

Fischer et al., "CFTR and calcium-activated chloride channels in primary cultures of human airway gland cells of serous or mucous phenotype," *Am J Physiol Lung Cell Mol Physiol* 299:L585-L594 2010.
Gomez-Pinilla et al., "Ano1 is a selective marker of interstitial cells of Cajal in the human and mouse gastrointestinal tract," *Am J Physiol Gastrointest Liver Physiol* 296:G1370-G1381, 2009.
Hartzell et al., "Calcium-Activated Chloride Channels," *Annu. Rev. Physiol.* 67:719-758, 2005.
Huang et al., "Studies on expression and function of the TMEM16A calcium-activated chloride channel," *PNAS* 106(50):21413-21418, Dec. 15, 2009.
Hwang et al., "Expression of anoctamin 1/TMEM16A by interstitial cells of Cajal is fundamental for slow wave activity in gastrointestinal muscles," *J Physiol* 587.20:4887-4904, 2009.
Kashyap et al., "Immunoreactivity for Ano1 detects depletion of Kit-positive interstitial cells of Cajal in patients with slow transit constipation," *Neurogastroenterol Motil* 23:760-765, 2011.
Kawamatsu et al., "2-Amino-4-phenylthiazole derivatives as antiatherogenic agents," *Eur J Med Chem* 16(4):355-362, 1981.
Kellerman et al., "Denufosol: A review of studies with inhaled P2Y$_2$ agonists that led to Phase 3," *Pulmonary Pharmacology & Therapeutics* 21:600-607, 2008.
Kumar et al., "Novel 5-substituted benzyloxy-2-arylbenzofuran-3-carboxylic acids as calcium activated chloride channel inhibitors," *Bioorganic & Medicinal Chemistry* 20:4237-4244, 2012.
Lee et al., "Mechanisms of $Ca^{2+}$-stimulated fluid secretion by porcine bronchial submucosal gland serous acinar cells," *Am J Physiol Lung Cell Mol Physiol* 298:L210-L231, 2010.
Lee et al., "Pharmacophore modeling and virtual screening studies for new VEGFR-2 kinase inhibitors," *European Journal of Medicinal Chemistry* 45:5420-5427, 2010.
Liu et al., "The acute nociceptive signals induced by bradykinin in rat sensory neurons are mediated by inhibition of M-type $K^+$ channels and activation of $Ca^{2+}$-activated Cl$^-$ channels," *The Journal of Clinical Investigation* 120(4):1240-1252, Apr. 2010.
Manoury et al., "TMEM16A/Anoctamin 1 protein mediates calcium-activated chloride currents in pulmonary arterial smooth muscle cells," *J Physiol* 588.13:2305-2314, 2010.
Mokale et al., "Synthesis and hypolipidemic activity of novel 2-(4-(2-substituted aminothiazole-4-yl) phenoxy) acetic acid derivatives," *European Journal of Medicinal Chemistry* 45:3096-3100, 2010.
Munchhof et al., "The identification of orally bioavailable thrombopoietin agonists," *Bioorganic &Medicinal Chemistry Letters* 19:1428-1430, 2009.
Namkung et al., "CFTR-Adenylyl Cyclase I Association Responsible for UTP Activation of CFTR in Well-Differentiated Primary Human Bronchial Cell Cultures," *Molecular Biology of the Cell* 21:2639-2648, Aug. 1, 2010.
Namkung et al., "Inhibition of $Ca^{2+}$-activated Cl$^-$ channels by gallotannins as a possible molecular basis for health benefits of red wine and green tea," *The FASEB Journal* 24:4178-4186, Nov. 2010.
Namkung et al., "Small-molecule activators of TMEM16A, a calcium-activated chloride channel, stimulate epithelial chloride secretion and intestinal contraction," *The FASEB Journal* 25:4048-4062, Nov. 2011.
Namkung et al., "TMEM16A Inhibitors Reveal TMEM16A as a Minor Component of Calcium-activated Chloride Channel Conductance in Airway and Intestinal Epithelial Cells," *The Journal of Biological Chemistry* 286(3):2365-2374, Jan. 21, 2011.
Nichols et al., "Diquafosol tetrasodium: a novel dry eye therapy," *Expert Opin. Investig. Drugs* 13(1):47-54, 2004.
Riordan et al., "Identification of the Cystic Fibrosis Gene: Cloning and Characterization of Complementary DNA," *Science* 245:1066-1073, Sep. 8, 1989.
Rock et al., "The transmembrane protein TMEM16A is required for normal development of the murine trachea," *Developmental Biology* 321:141-149, 2008.
Rock et al., "Transmembrane Protein 16A (TMEM16A) Is a $Ca^{2+}$-regulated Cl$^-$ Secretory Channel in Mouse Airways," *The Journal of Biological Chemistry* 284(22):14875-14880, May 29, 2009.
Romanenko et al., "*Tmem16A* Encodes the $Ca^{2+}$-activated Cl$^-$ Channel in Mouse Submandibular Salivary Gland Acinar Cells," *The Journal of Biological Chemistry* 285(17):12990-13001, Apr. 23, 2010.
Scheiff et al., "2-Amino5-benzoyl-4-phenylthiasoles: Development of Potent and selective adenosine $A_1$ receptor antagonists," *Bioorganic & Medicinal Chemistry* 18:2195-2203, 2010.
Schroeder et al., "Expression Cloning of TMEM16A as a Calcium-Activated Chloride Channel Subunit," *Cell* 134:1019-1029, Sep. 19, 2008.
Shipps, Jr. et al., "Aminothiazole inhibitors of HCV RNA Polymerase," *Bioorganic & Medicinal Chemistry Letters* 15:115-119, 2005.
Sloane et al., "Cystic fibrosis transmembrane conductance regulator protein repair as a therapeutic strategy in cystic fibrosis," *Curr Opin Pulm Med* 16(6):591-597, 2010.
Stadelmann et al., "Application of an in vitro drug screening assay based on the release of phosphoglucose isomerase to determine the structure-activity relationship of thiazolides against *Echinococcus multilocularis* metacestodes," *J Antimicrob Chemother* 65:512-519, 2010.
Steiner et al., "Pulmonary pharmacokinetics and safety of nebulized duramycin in healthy male volunteers," *Naunyn-Schmiedeberg's Arch Pharmacol* 378:323-333, 2008.
Tabbara et al., "Sjögren syndrome," *Current Opinion in Ophthalmology* 11:449-454, 2000.
Veit et al., "Proinflammatory cytokine secretion is suppressed by TMEM16A or CFTR channel activity in human cystic fibrosis bronchial epithelia," *Molecular Biology of the Cell* 23:4188-4202, Nov. 1, 2012.
Verkman et al., "Chloride channels as drug targets," *Nat Rev Drug Discov* 8(2):153-171, Feb. 2009.
Verkman et al., "Role of airway surface liquid and submucosal glands in cystic fibrosis lung disease," *Am J Physiol Cell Physiol* 284:C2-C15, 2003.
White et al., "Airway Epithelium Directed Gene Therapy for Cystic Fibrosis," *Medicinal Chemistry* 2:499-503, 2006.
Yang et al., "TMEM16A confers receptor-activated calcium-dependent chloride conductance," *Nature* 455:1210-1216, Oct. 30, 2008.

* cited by examiner

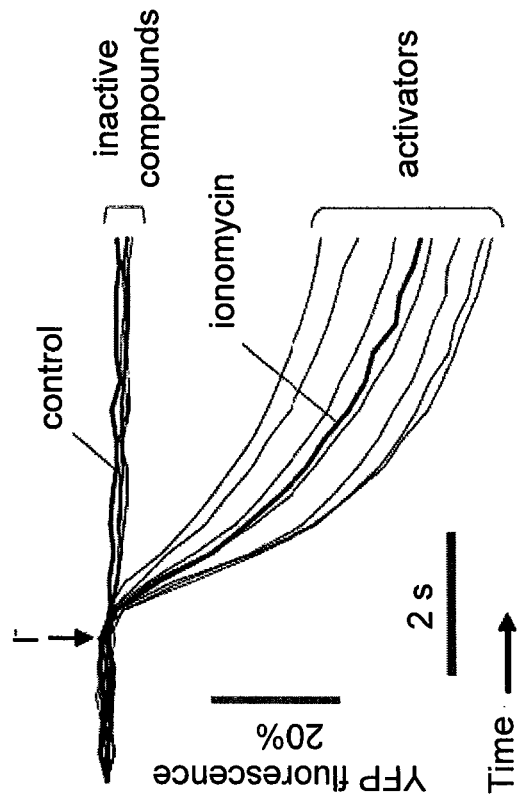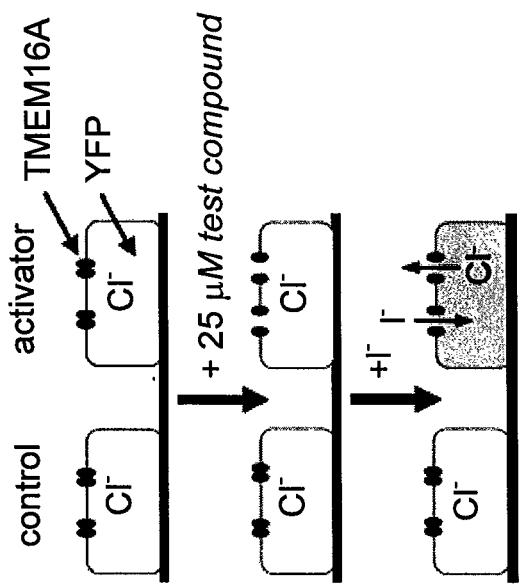
Fig. 1A
Fig. 1B

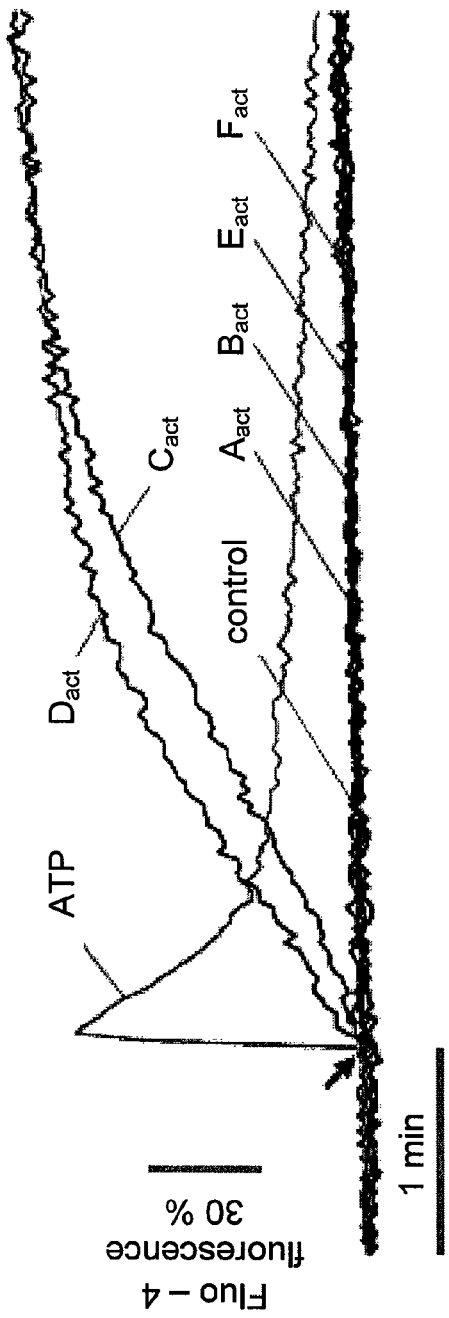
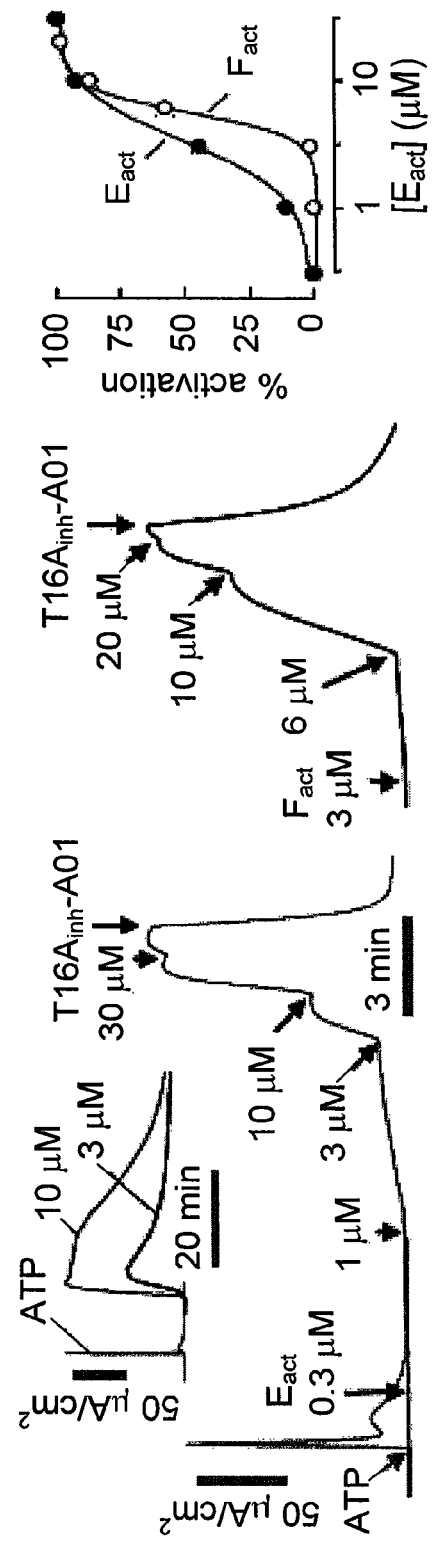
Fig. 2A
Fig. 2B

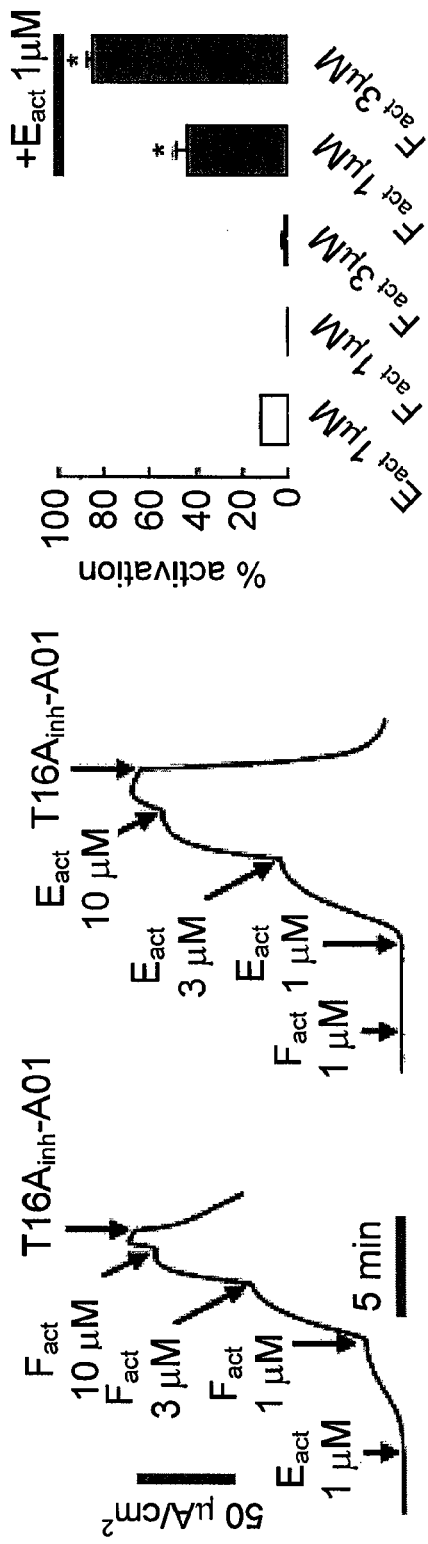
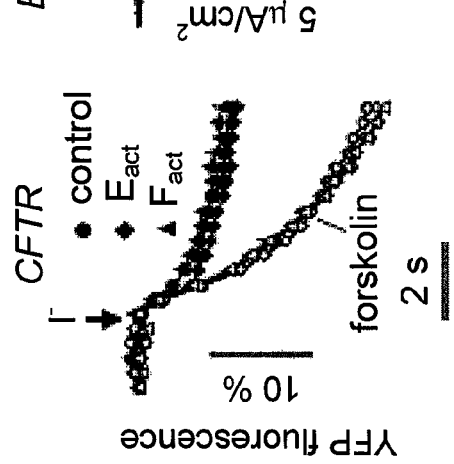
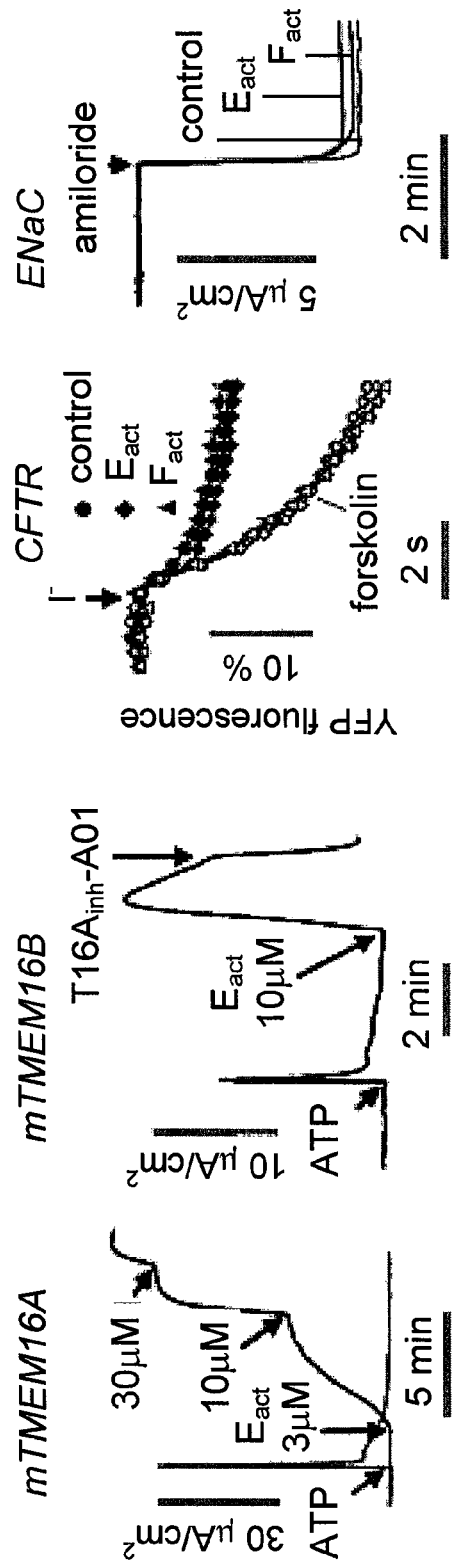
Fig. 2C
Fig. 2D
Fig. 2E

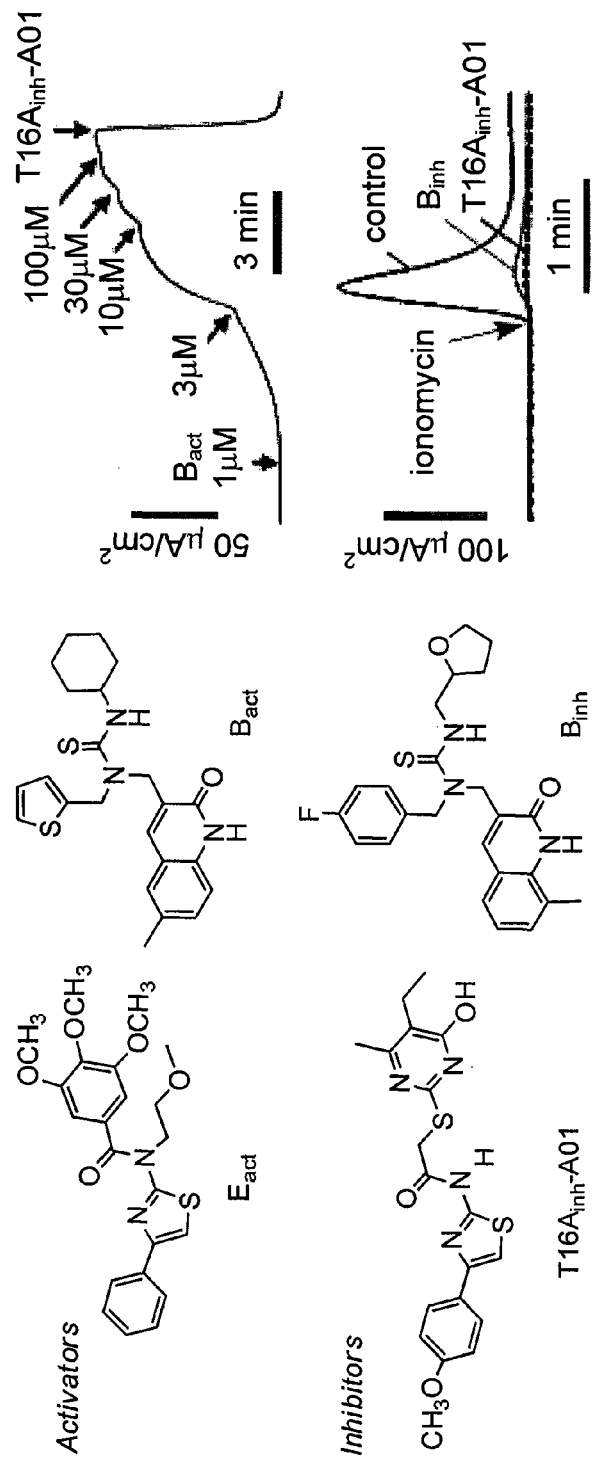
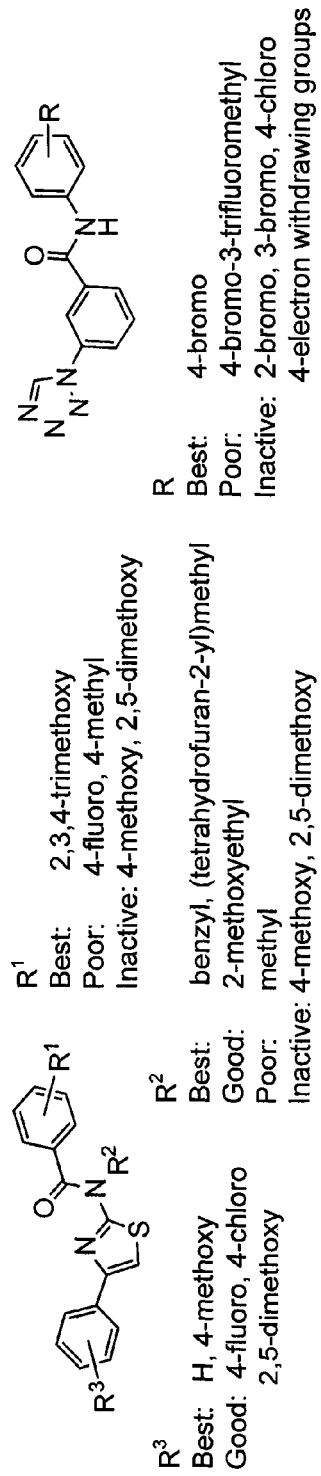
Fig. 3A
Fig. 3B

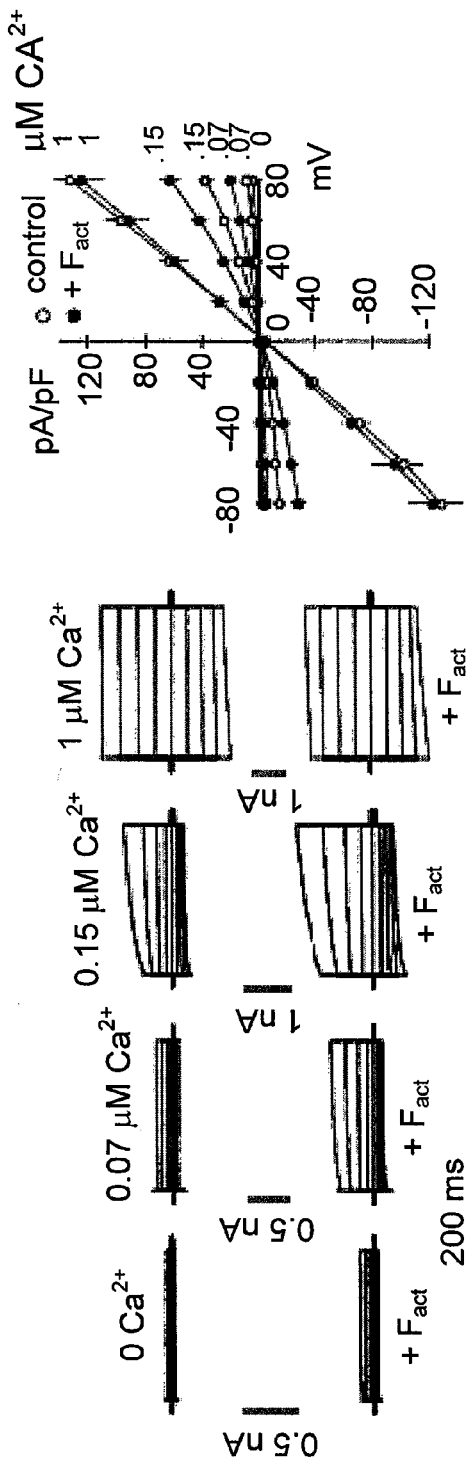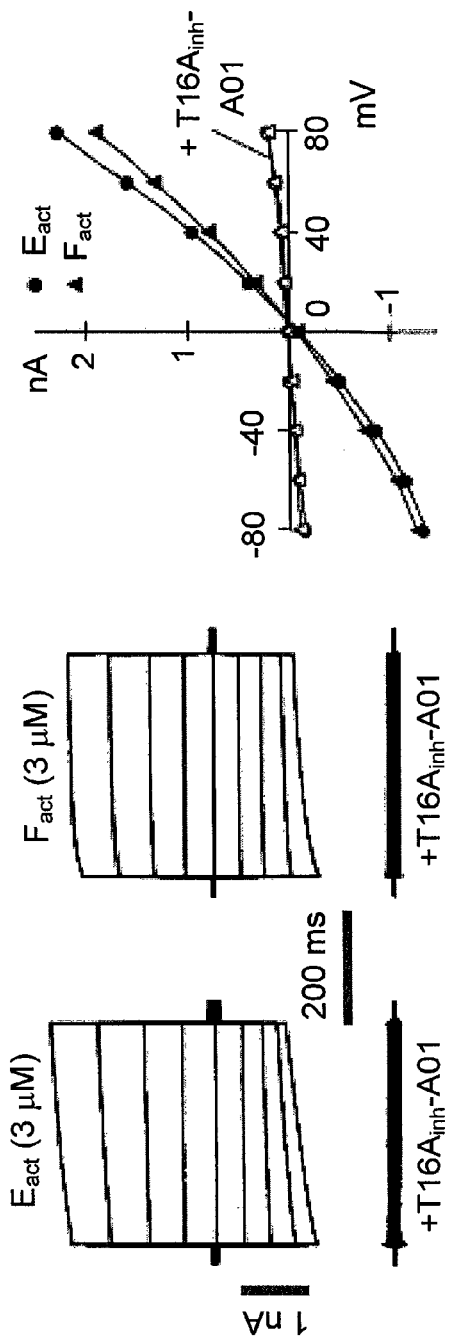

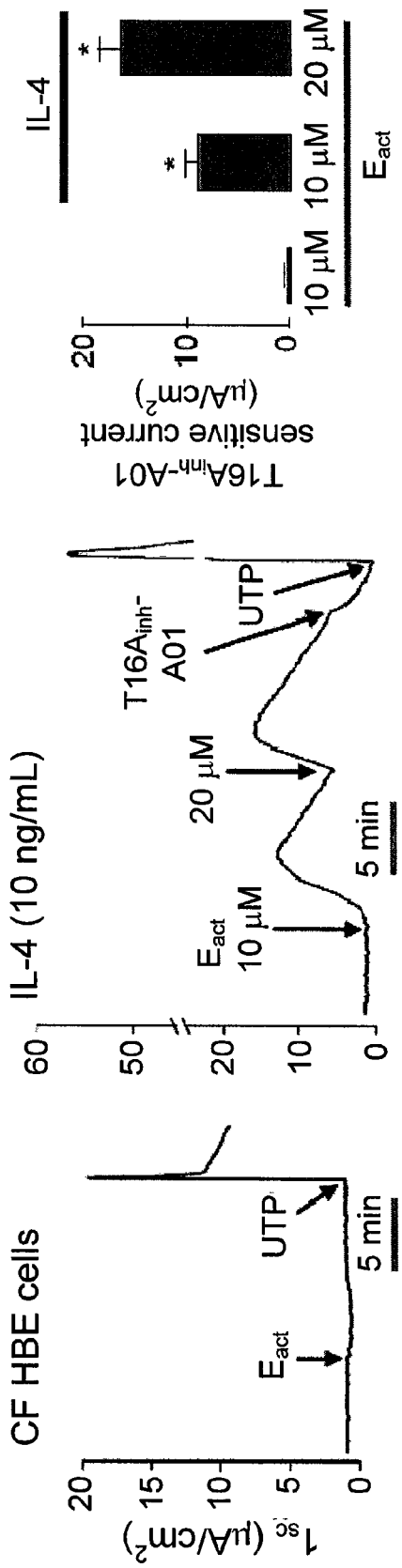
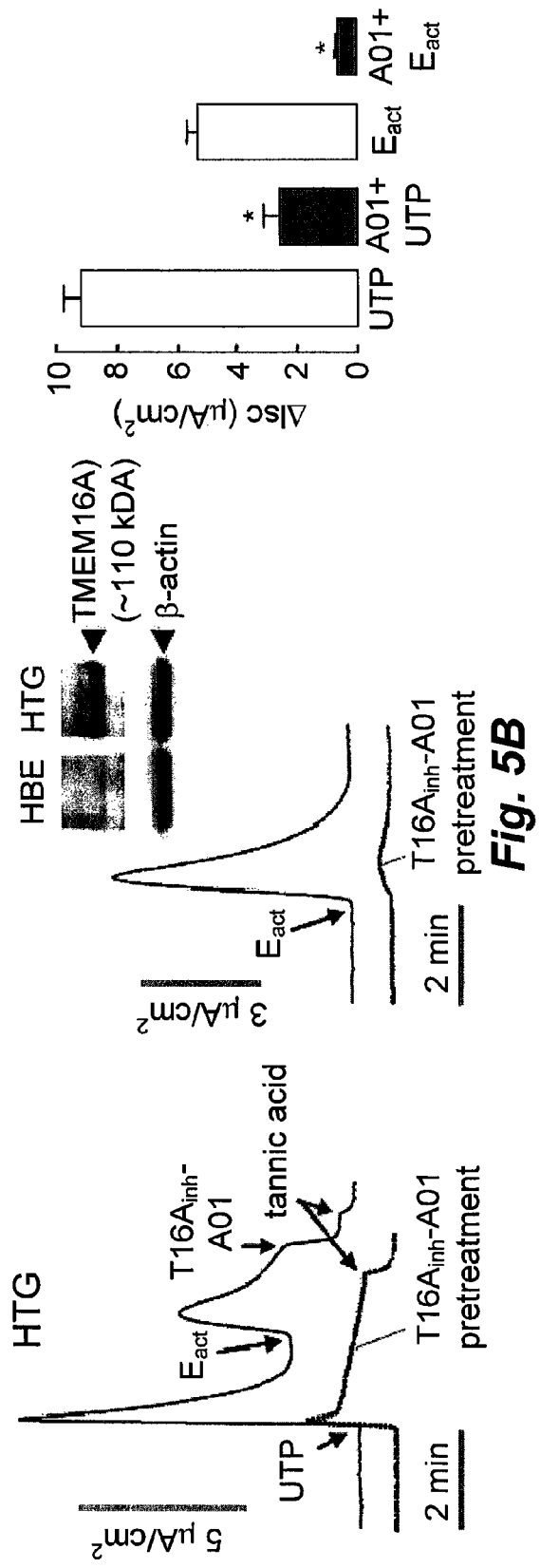
Fig. 5A
Fig. 5B

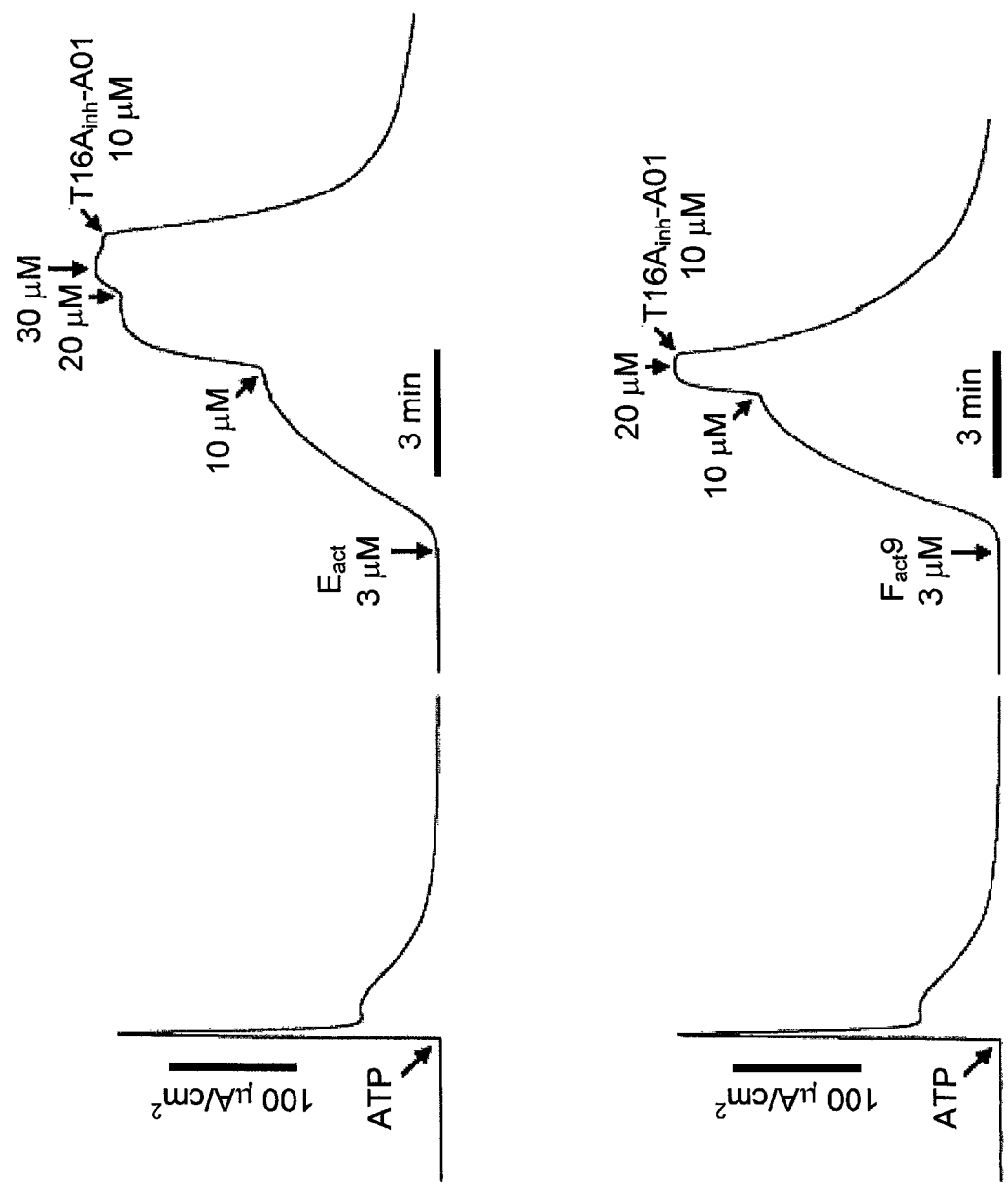

SMALL MOLECULE ACTIVATORS OF CALCIUM-ACTIVATED CHLORIDE CHANNELS AND METHODS OF USE

CROSS-REFERENCE TO RELATED APPLICATION

This application claims benefit of priority under 35 U.S.C. §119(e) of U.S. Provisional Patent Application Ser. No. 61/515,555, filed Aug. 5, 2011, which is incorporated herein by reference in its entirety.

STATEMENT OF GOVERNMENT INTEREST

This invention was made with government support under Grant Nos. DK72517, HL73856, DK35124, DK86125, EB00415, and EY13574 awarded by the National Institutes of Health. The government has certain rights in this invention.

BACKGROUND

Technical Field

Therapeutics are needed for treating diseases and disorders related to aberrant calcium-activated chloride channel (CaCC) activity, such as cystic fibrosis dry mouth, dry eye, and gastrointestinal hypomotility disorders. Small molecule compounds are described herein that are potent activators of CaCC activity and may be used for treating such diseases and disorders.

Description of the Related Art

Lung disease pathogenesis in cystic fibrosis (CF) is thought to involve distinct defects in airway submucosal gland fluid secretion, causing secretion of hyperviscous mucus (Boucher (2007) *Annu. Rev. Med.* 58, 157-170), and in airway surface transport, causing reduced airway surface liquid volume (Verkman et al. (2003) *Am. J. Physiol. Cell Physiol.* 284, C2-15). Both related defects are likely attributed to defective cystic fibrosis transmembrane conductance regulator (CFTR)-mediated secretion, and perhaps epithelial sodium channel (ENaC) hyperactivity, though the evidence remains controversial (Donaldson et al. (2007) *Chest.* 132, 1631-1636). Small-molecule therapies under development to correct the underlying CFTR defect include correctors, potentiators, and read-though enhancers to restore Cl⁻ conductance in cells expressing CF-causing mutant CFTRs (Verkman, A. S., and Galietta, L. J. (2009) Chloride channels as drug targets. *Nat. Rev. Drug. Discov.* 8, 153-171; Sloane, et al. (2010) *Curr. Opin. Pulm. Med.* 16, 591-597), as well as gene replacement therapies (White et al. (2006) *Med. Chem.* 2, 499-503. Therapies targeting the activation of alternative Cl⁻ channels, the calcium-activated chloride channels (CaCCs), have received considerable attention as well, as CaCCs are robustly expressed in non-CF and CF airways where CFTR is normally expressed. Other disorders associated with Cl⁻ channel dysfunction include salivary gland dysfunction, such as in Sjogren's syndrome and following radiation injury, dry eye syndrome, and intestinal hypomotility. Drug candidates for treatment of these diseases and disorders are needed (Verkman et al., (2009) *Nat. Rev. Drug Discovery* 8, 153-171; Tabbara et al. (2000) *Curr Opin Ophthalmol* 11, 449-454).

BRIEF SUMMARY

Provided herein are compounds, pharmaceutical compositions comprising these compounds, and methods for using these compounds and compositions for treatment of diseases, disorders, and conditions that are treatable by activating a CaCC. The following embodiments are provided herein.

Embodiment 1

A pharmaceutical composition comprising a pharmaceutically acceptable excipient and a compound of structure (I):

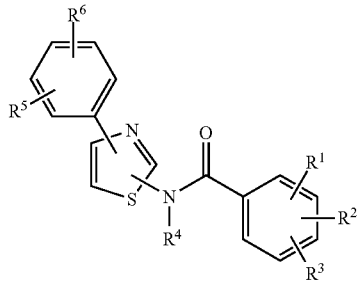

(I)

or a stereoisomer, tautomer, solvate, or pharmaceutically acceptable salt thereof, wherein $R^1$, $R^2$ and $R^3$ are each independently alkoxy; $R^4$ is aralkyl, heteroaralkyl, heterocyclylalkyl or alkoxyalkyl; and $R^5$ and $R^6$ are each independently hydrogen, alkoxy or halo.

Embodiment 2

The pharmaceutical composition of Embodiment 1, wherein the compound has the following structure (Ia):

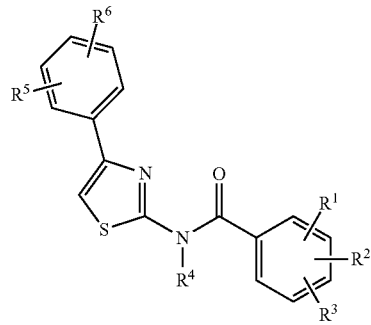

(Ia)

Embodiment 3

The pharmaceutical composition of Embodiment 1, wherein the compound has one of the following structures (Ib) or (Ic):

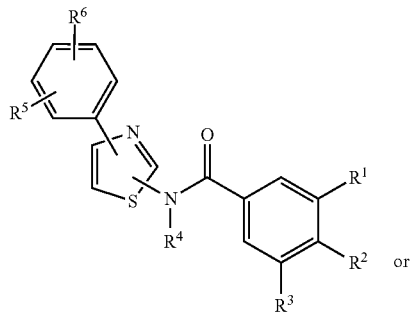

(Ib)

or

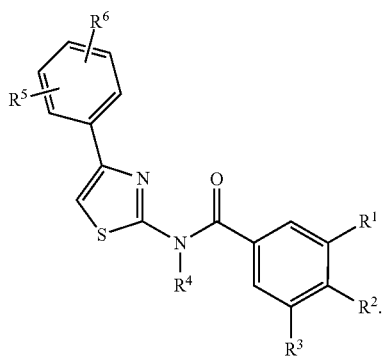

(Ic)

Embodiment 4

The pharmaceutical composition of any of Embodiments 1-3, wherein at least one of $R^1$, $R^2$ or $R^3$ is methoxy.

Embodiment 5

The pharmaceutical composition of any of Embodiments 1-4, wherein each of $R^1$, $R^2$ and $R^3$ is methoxy.

Embodiment 6

The pharmaceutical composition of any of Embodiments 1-5, wherein $R^4$ is benzyl, tetrahydrofuran-2-yl-methyl, furan-2-yl-methyl, 2-methoxyethyl, tetrahydropyran-2-yl-methyl, pyrid-4-yl-methyl or pyrid-2-yl-methyl.

Embodiment 7

The pharmaceutical composition of any of Embodiments 1-6, wherein at least one of $R^5$ or $R^6$ is at the 4-position.

Embodiment 8

The pharmaceutical composition of any of Embodiments 1-6, wherein $R^5$ is at the 2-position and $R^6$ is at the 5-position.

Embodiment 9

The pharmaceutical composition of any of Embodiments 1-8, wherein at least one of $R^5$ or $R^6$ is hydrogen.

Embodiment 10

The pharmaceutical composition of any of Embodiments 1-8, wherein each of $R^5$ and $R^6$ is hydrogen.

Embodiment 11

The pharmaceutical composition of any of Embodiments 1-8, wherein at least one of $R^5$ or $R^6$ is methoxy.

Embodiment 12

The pharmaceutical composition of any of Embodiments 1-8, wherein each of $R^5$ and $R^6$ is methoxy.

Embodiment 13

The pharmaceutical composition of any of Embodiments 1-8, wherein at least one of $R^5$ or $R^6$ is chloro.

Embodiment 14

The pharmaceutical composition of any of Embodiments 1-8, wherein at least one of $R^5$ or $R^6$ is fluoro.

Embodiment 15

The pharmaceutical composition of any of Embodiments 1-8, wherein $R^5$ is hydrogen and $R^6$ is methoxy.

Embodiment 16

The pharmaceutical composition of any of Embodiments 1-8, wherein $R^5$ hydrogen and $R^6$ is chloro.

Embodiment 17

The pharmaceutical composition of any of Embodiments 1-8, wherein $R^5$ is hydrogen and $R^6$ is fluoro.

Embodiment 18

The pharmaceutical composition of any of Embodiments 1-17, wherein $R^4$ is tetrahydropyran-2-yl-methyl, pyrid-4-yl-methyl, or pyrid-2-yl-methyl.

Embodiment 19

The pharmaceutical composition of any of Embodiments 1, 2, or 3, wherein the compound has one of the following structures:

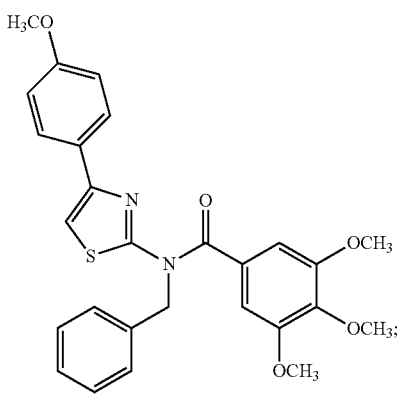

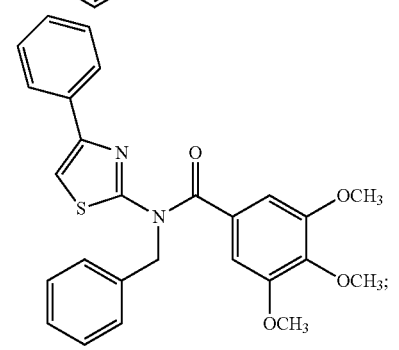

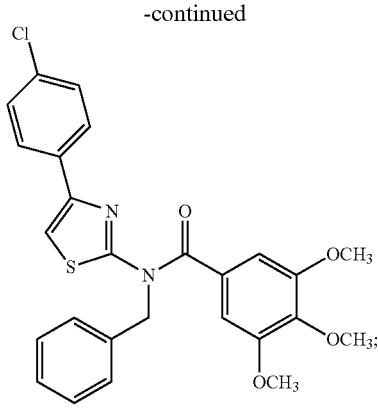
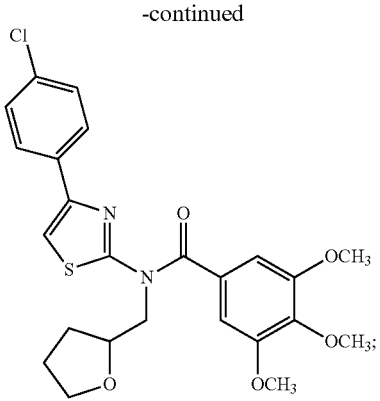
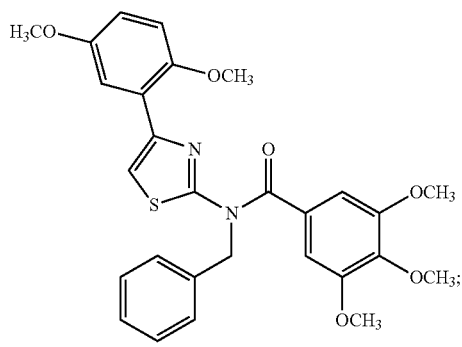
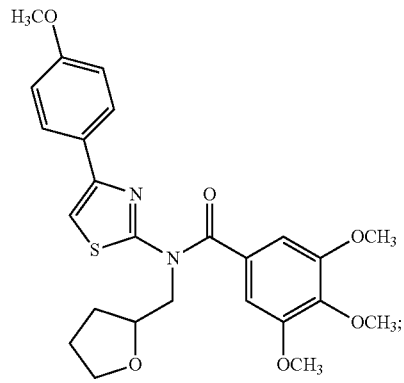
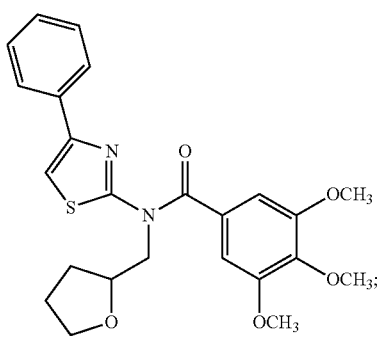
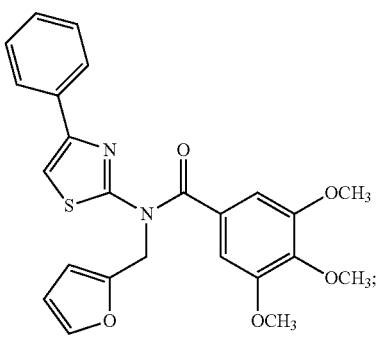
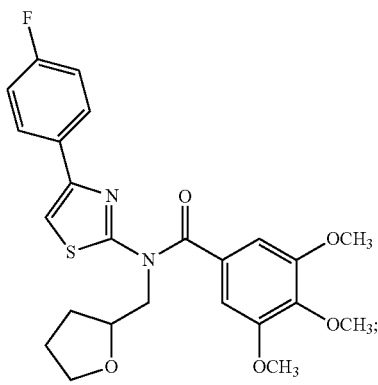
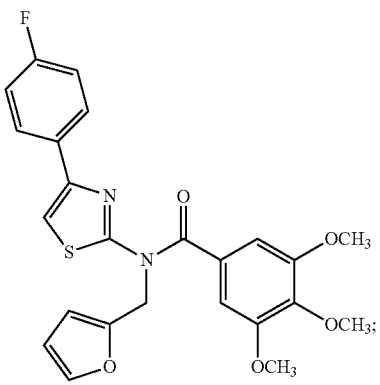

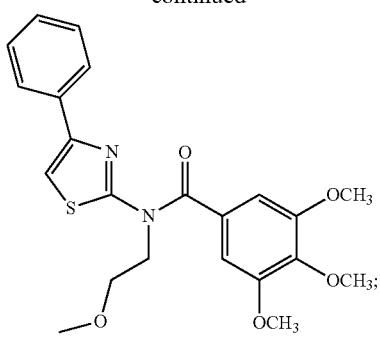

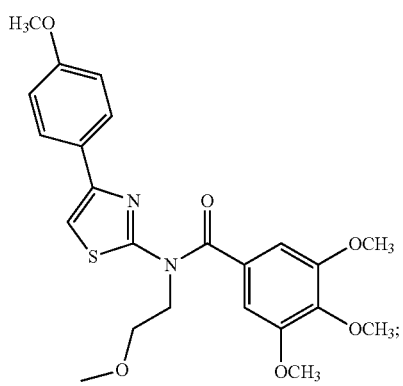

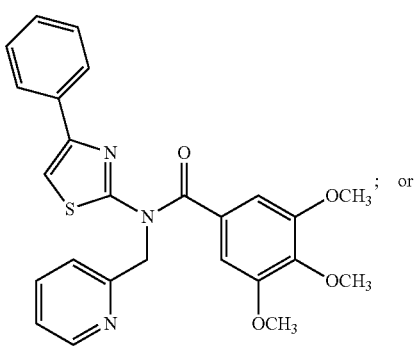

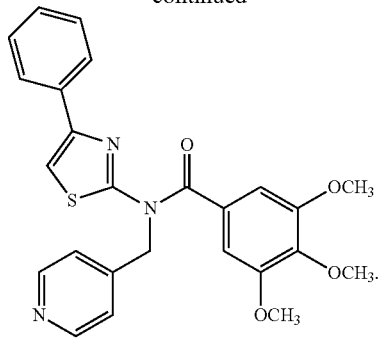

Embodiment 20

A pharmaceutical composition comprising a pharmaceutically acceptable excipient and a compound of structure (II):

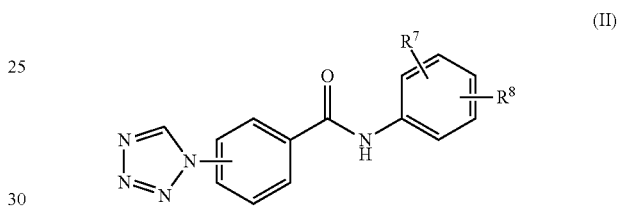

or a stereoisomer, tautomer, solvate, or pharmaceutically acceptable salt thereof, wherein $R^7$ is hydrogen or trifluoroalkyl; and $R^8$ is bromo or alkyl.

Embodiment 21

The pharmaceutical composition of Embodiment 20, wherein the compound has the following structure (IIa):

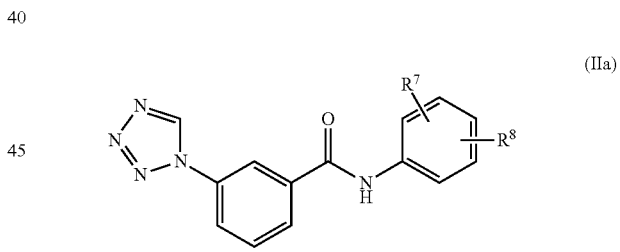

Embodiment 22

The pharmaceutical composition of Embodiment 20, wherein the compound has one of the following structures (IIb) or (IIc):

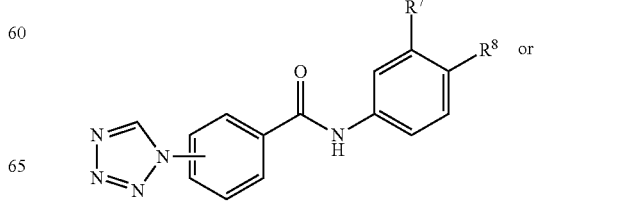

-continued

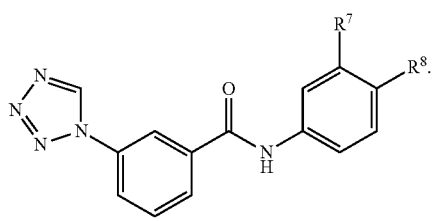

(IIc)

Embodiment 23

The pharmaceutical composition of any of Embodiments 20-22, wherein R⁷ is hydrogen.

Embodiment 24

The pharmaceutical composition of any of Embodiments 20-23, wherein R⁸ is bromo.

Embodiment 25

The pharmaceutical composition of any of Embodiments 20-22 or 24, wherein R⁷ is —CF₃.

Embodiment 26

The pharmaceutical composition of any of Embodiments 20-23 or 25, wherein R⁸ is alkyl.

Embodiment 27

The pharmaceutical composition of Embodiment 26, wherein R⁸ is isopropyl.

Embodiment 28

The pharmaceutical composition of Embodiment 20, wherein the compound has one of the following structures:

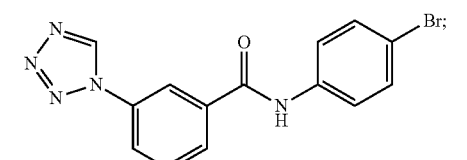

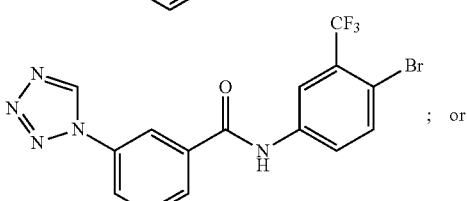

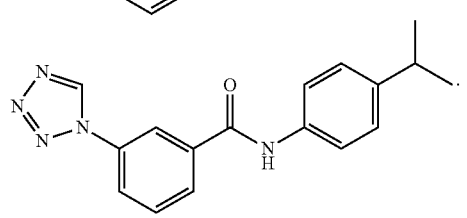

Embodiment 29

A method for treating a disease or condition treatable by activating a calcium-activated chloride ion channel in a subject, the method comprising administering the pharmaceutical composition according to any one of Embodiments 1-28 to the subject.

Embodiment 30

The method of Embodiment 29, wherein the calcium-activated chloride ion channel is TMEM16A.

Embodiment 31

The method of Embodiment 29 or 30, wherein the disease or condition is salivary gland dysfunction, cystic fibrosis, dry eye syndrome, dry mouth, or intestinal hypomotility.

Embodiment 32

The method of Embodiment 31, wherein the salivary gland dysfunction is Sjogren's syndrome.

Embodiment 33

The method of Embodiment 31, wherein the salivary gland dysfunction is caused by radiation injury.

Embodiment 34

A method for treating a disease or condition treatable by activating a calcium-activated chloride ion channel in a subject, the method comprising administering sequentially or concurrently (a) the pharmaceutical composition of any one of Embodiments 1-19 and (b) the pharmaceutical composition of any one of Embodiments 20-28.

Embodiment 35

The method of Embodiment 34, wherein the calcium-activated chloride ion channel is TMEM16A.

Embodiment 36

The method of Embodiment 34 or 35, wherein the disease or condition is salivary gland dysfunction, cystic fibrosis, dry eye syndrome, dry mouth, or intestinal hypomotility.

Embodiment 37

The method of Embodiment 36, wherein the salivary gland dysfunction is Sjogren's syndrome.

Embodiment 38

The method of Embodiment 36, wherein the salivary gland dysfunction is caused by radiation injury.

Embodiment 39

A compound having the following structure (I):

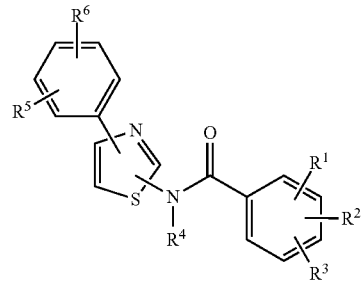

(I)

or a stereoisomer, tautomer, solvate, or pharmaceutically acceptable salt thereof, wherein $R^1$, $R^2$ and $R^3$ are each independently alkoxy; $R^5$ and $R^6$ are each independently hydrogen, alkoxy or halo; and $R^4$ is a 6-membered heteroaralkyl or 6-membered heterocyclylalkyl.

Embodiment 40

The compound of Embodiment 39, wherein the compound has the following structure (Ia):

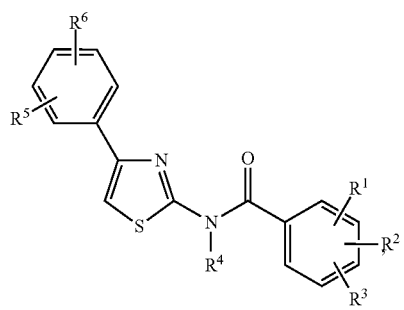

(Ia)

Embodiment 41

The compound of Embodiment 39, wherein the compound has one of the following structures (Ib) or (Ic):

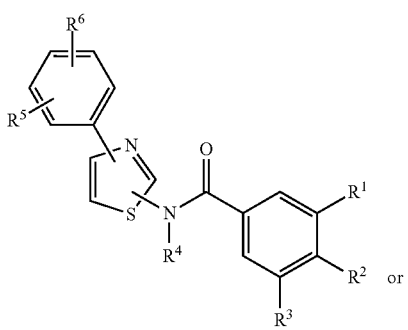

(Ib)

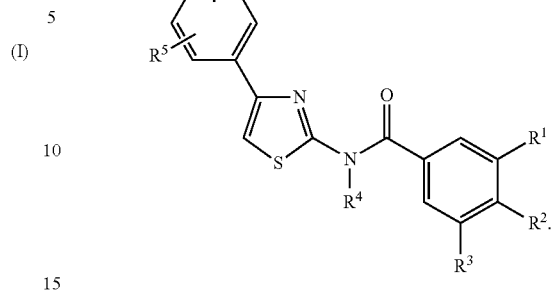

(Ic)

Embodiment 42

The compound of any of Embodiments 39-41, wherein at least one of $R^1$, $R^2$ or $R^3$ is methoxy.

Embodiment 43

The compound of any of Embodiments 39-42, wherein each of $R^1$, $R^2$ and $R^3$ is methoxy.

Embodiment 44

The compound of any of Embodiments 39-43, wherein $R^4$ is tetrahydropyranyl-methyl or pyridyl-methyl.

Embodiment 45

The compound of Embodiment 44, wherein $R^4$ is tetrahydropyran-2-yl-methyl, pyrid-4-yl-methyl or pyrid-2-yl-methyl.

Embodiment 46

The compound of any of Embodiments 39-45, wherein at least one of $R^5$ or $R^6$ is at the 4-position.

Embodiment 47

The compound of any of Embodiments 39-45, wherein $R^5$ is at the 2-position and $R^6$ is at the 5-position.

Embodiment 48

The compound of any of Embodiments 39-47, wherein at least one of $R^5$ or $R^6$ is hydrogen.

Embodiment 49

The compound of any of Embodiments 39-47, wherein each of $R^5$ and $R^6$ is hydrogen.

Embodiment 50

The compound of any of Embodiments 39-47, wherein at least one of $R^5$ or $R^6$ is methoxy.

Embodiment 51

The compound of any of Embodiments 39-47, wherein each of $R^5$ and $R^6$ is methoxy.

Embodiment 52

The compound of any of Embodiments 39-47, wherein at least one of $R^5$ or $R^6$ is chloro.

Embodiment 53

The compound of any of Embodiments 39-47, wherein at least one of $R^5$ or $R^6$ is fluoro.

Embodiment 54

The compound of any of Embodiments 39-47, wherein $R^5$ is hydrogen and $R^6$ is methoxy.

Embodiment 55

The compound of any of Embodiments 39-47, wherein $R^5$ is hydrogen and $R^6$ is chloro.

Embodiment 56

The compound of any of Embodiments 39-47, wherein $R^5$ is hydrogen and $R^6$ is fluoro.

Embodiment 57

The compound of Embodiment 39, wherein the compound has one of the following structures:

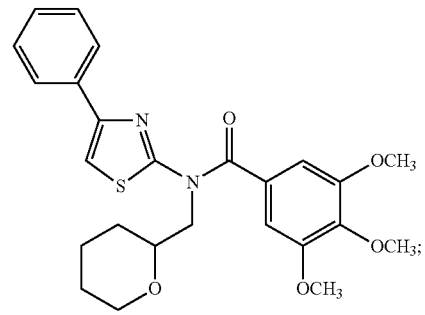

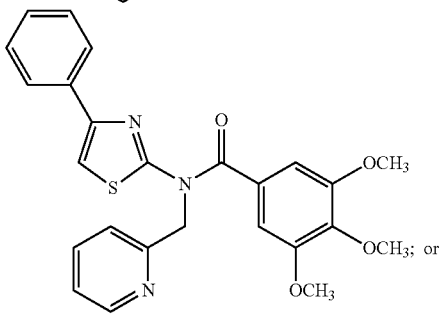

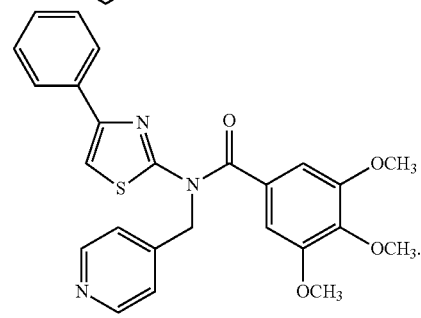

Embodiment 58

A pharmaceutical composition comprising a pharmaceutically acceptable excipient and a compound of any of Embodiments 39-57.

Embodiment 59

A compound having the following structure (II):

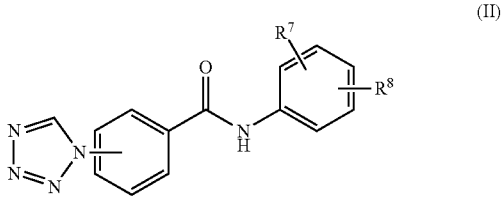

(II)

or a stereoisomer, tautomer, solvate, or pharmaceutically acceptable salt thereof, wherein $R^7$ is hydrogen or trifluoroalkyl; and $R^8$ is bromo or alkyl, wherein when $R^8$ is bromo, $R^7$ is trifluoroalkyl, and wherein when $R^7$ is H, $R^8$ is not isopropyl at the 4 position.

Embodiment 60

The compound of Embodiment 59, wherein the compound has the following structure (IIa):

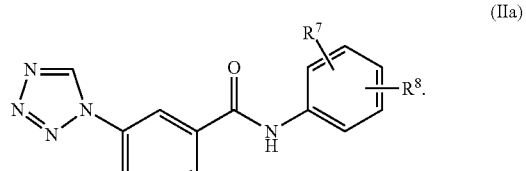

(IIa)

Embodiment 61

The compound of Embodiment 59, wherein the compound has one of the following structures (IIb) or (IIc):

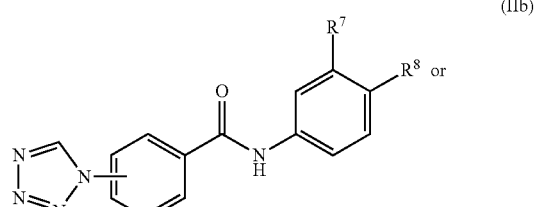

(IIb)

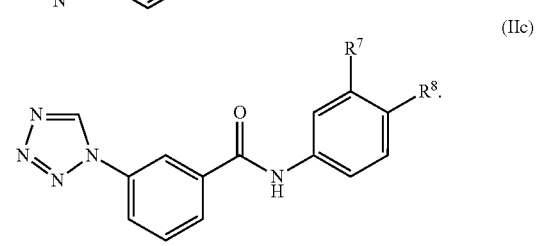

(IIc)

Embodiment 62

The compound of any of Embodiments 59-61, wherein $R^7$ is hydrogen.

Embodiment 63

The compound of any of Embodiments 59-61, wherein $R^8$ is bromo.

Embodiment 64

The compound of any of Embodiments 59-61 and 63, wherein $R^7$ is —$CF_3$.

Embodiment 65

The compound of any of Embodiments 59-62 and 64, wherein $R^8$ is alkyl, wherein when $R^7$ is H, $R^8$ is not isopropyl at the 4 position.

Embodiment 66

The compound of Embodiment 59, wherein the compound has the following structure:

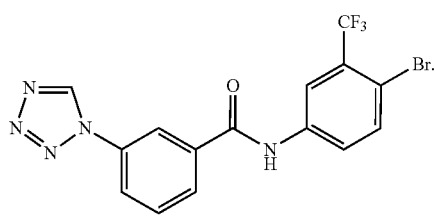

Embodiment 67

A pharmaceutical composition comprising a pharmaceutically acceptable excipient and a compound of any of Embodiments 59-66.

Embodiment 68

The pharmaceutical composition according to any one of Embodiments 1-28, 58, and 67 for treating a disease or condition treatable by activating a calcium-activated chloride ion channel.

Embodiment 69

The pharmaceutical composition according to any one of Embodiments 1-28, 58, and 67 for use in treating a disease or condition treatable by activating a calcium-activated chloride ion channel.

Embodiment 70

Use of the pharmaceutical composition according to any one of Embodiments 1-28, 58, and 67 for the manufacture of a medicament for treating a disease or condition treatable by activating a calcium-activated chloride ion channel.

Embodiment 71

The pharmaceutical composition of Embodiment 68 or 69 or the use of Embodiment 70, wherein the calcium-activated chloride ion channel is TMEM16A.

Embodiment 72

The pharmaceutical composition of Embodiment 68 or 69 or the use of Embodiment 70, wherein the disease or condition is salivary gland dysfunction, cystic fibrosis, dry eye syndrome, dry mouth, or intestinal hypomotility.

Embodiment 73

The pharmaceutical composition of Embodiment 72 or the use of Embodiment 72, wherein the salivary gland dysfunction is Sjogren's syndrome.

Embodiment 74

The pharmaceutical composition of Embodiment 72 or the use of Embodiment 72, wherein the salivary gland dysfunction is caused by radiation injury.

Embodiment 75

A preparation comprising (a) the pharmaceutical composition of any one of Embodiments 1-19 and (b) the pharmaceutical composition of any one of Embodiments 20-28 for treating a disease or condition treatable by activating a calcium-activated chloride ion channel in a subject, wherein the pharmaceutical composition of any one of Embodiments 1-19 and the pharmaceutical composition of any one of Embodiments 20-28 are formulated for administration sequentially or concurrently.

Embodiment 76

A preparation comprising (a) the pharmaceutical composition of any one of Embodiments 1-19 and (b) the pharmaceutical composition of any one of Embodiments 20-28 for use in treating a disease or condition treatable by activating a calcium-activated chloride ion channel in a subject, wherein the pharmaceutical composition of any one of Embodiments 1-19 and the pharmaceutical composition of any one of Embodiments 20-28 are formulated for administration sequentially or concurrently.

Embodiment 77

Use of a preparation comprising (a) the pharmaceutical composition of any one of Embodiments 1-19 and (b) the pharmaceutical composition of any one of Embodiments 20-28 for the manufacture of a medicament for treating a disease or condition treatable by activating a calcium-activated chloride ion channel in a subject, wherein the pharmaceutical composition of any one of Embodiments 1-19 and the pharmaceutical composition of any one of Embodiments 20-28 are formulated for administration sequentially or concurrently.

Embodiment 78

The preparation of Embodiment 75 and 76 or the use of Embodiment 77, wherein the calcium-activated chloride ion channel is TMEM16A.

Embodiment 79

The preparation of Embodiment 75 and 76 or the use of Embodiment 77, wherein the disease or condition is salivary gland dysfunction, cystic fibrosis, dry eye syndrome, dry mouth, or intestinal hypomotility.

Embodiment 80

The preparation of Embodiment 79 or the use of Embodiment 79, wherein the salivary gland dysfunction is Sjogren's syndrome.

Embodiment 81

The preparation of Embodiment 79 or the use of Embodiment 79, wherein the salivary gland dysfunction is caused by radiation injury.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIG. 1A-C. Identification of small-molecule TMEM16A activators by high-throughput screening. FIG. 1A. Screening protocol. FRT cells stably expressing TMEM16A and the halide-sensitive cytoplasmic fluorescent sensor YFP-H148Q/I152L/F46L were incubated for 10 min with test compound. Fluorescence was monitored in response to addition of iodide. FIG. 1B. Fluorescence measured in single wells of 96-well plates, showing vehicle and positive (ionomycin) controls and examples of inactive and active compounds. FIG. 1C. Structures of TMEM16A activators of six different chemical classes.

FIG. 2A-E. Characterization of TMEM16A activators. FIG. 2A. Cytoplasmic calcium measured by Fluo-4 fluorescence. 100 μM ATP (gray line) or 10 μM of indicated TMEM16A activators were added at the arrow. FIG. 2B. Apical membrane current measured in TMEM16A-expressing FRT cells in the presence of a transepithelial chloride gradient and after basolateral membrane permeabilization. (left and center) Representative current traces showing ATP (100 μM), $E_{act}$ or $F_{act}$ stimulated TMEM16A Cl⁻ current. T16A$_{inh}$-A01 (10 μM) added where indicated. Inset shows long-time $E_{act}$ effect. (right) Concentration-activation data summary (mean±S.E., n=4-6). FIG. 2C. Synergistic effect of $E_{act}$ and $F_{act}$. (left and center) Representative current traces showing synergy. (right) Data summary of low doses of TMEM16A activation (mean±S.E., n=5, * P<0.05). FIG. 2D. Apical membrane current measured in FRT cells transfected with mouse TMEM16A or TMEM16B. FIG. 2E. Effect of $E_{act}$ and $F_{act}$ on CFTR and ENaC. (left) FRT cells expressing wild type CFTR and YFP indicator were pretreated for 5 min with 10 μM $E_{act}$ and $F_{act}$. Forskolin (10 μM) added as indicated. (right) HBE cells were pre-treated for 5 min with 10 μM $E_{act}$ and $F_{act}$, with amiloride (10 μM) added as indicated.

FIG. 3A-C. Structure-activity analysis and synthesis of TMEM16A activators. FIG. 3A. Structural similarities between TMEM16A inhibitors and activators. Apical membrane current measurements show activation of TMEM16A by $B_{act}$ (top), inhibition of ionomycin (1 μM)-induced TMEM16A currents by pretreatment B and E class analogs (each 10 μM). FIG. 3B. Summary of structural determinants for TMEM16A activation (left, $E_{act}$ class; right $F_{act}$ class). FIG. 3C. Synthesis of $E_{act}$ and $F_{act}$ analogs (see Examples).

FIG. 4A-D. Patch-clamp analysis of Ca$^{2+}$ requirements for TMEM16A activation by $E_{act}$ and $F_{act}$. FIG. 4A. Apical membrane current measured in TMEM16A-expressing FRT cells. ER calcium stores were depleted by CPA (50 μM, 30 min) and 0 CaCl$_2$ in bath. ATP (100 μM), $F_{act}$ (10 μM), $E_{act}$ (10 μM) and T16A$_{inh}$-A01 (10 μM) were added as indicated.

FIG. 4B and FIG. 4C. Whole-cell TMEM16A currents were recorded at a holding potential at 0 mV, and pulsing to voltages between ±80 mV (in steps of 20 mV) in the absence and presence of 3 µM $E_{act}$ or 10 µM $F_{act}$. Free calcium concentration of pipette solutions were clamped at 0 µM, 0.07 µM, 0.15 µM, and 1 µM. $E_{act}$ (3 µM) or $F_{act}$ (10 µM) added as indicated. (right) Current/voltage (I/V) plots of mean currents at the middle of each voltage pulse. The $Ca^{2+}$ concentration is indicated to the right. FIG. 4D. TMEM16A inhibited by 10 µM $T16A_{inh}$-A01 after stimulation by $E_{act}$ or $F_{act}$.

FIG. 5A-B. Airway epithelial chloride secretion. FIG. 5A. Short-circuit current in CF HBE cells. $E_{act}$ and UTP (100 µM) were added in control (left) and IL-4 (10 ng/ml, 24 h, middle) treated CF HBE cells. (right) Summary of $E_{act}$-induced, $T16A_{inh}$-A01-sensitive peak current (mean±S.E., n=6-8, * P<0.05). ENaC was inhibited by 10 µM amiloride. FIG. 5B. $E_{act}$ (10 µM) and UTP (100 µM) induced CaCC Cl⁻ current measured in primary cultures of non-CF human tracheal gland (HTG) serous cells. (left and gmiddle) TMEM16A, CFTR and ENaC were inhibited by pretreatment with $T16A_{inh}$-A01, $CFTR_{inh}$-172 and amiloride, respectively. Inset: TMEM16A immunoblot in whole cell homogenates of CF HBE and HTG cells. (right) Summary of UTP and $E_{act}$-induced peak current in the presence and absence of $T16A_{inh}$-A01 (mean±S.E., n=3, * P<0.05).

FIG. 6A. TMEM16A immunohistochemistry in CF (left) and non-CF (right) human bronchi showing apical membrane expression in serous gland epithelial cells (arrows). Scale bar: 20 µm. FIG. 6B. Mucous (fluid) secretion in human bronchi. (top) Images of mucus bubbles formed under oil in response to basolateral application of 300 nM carbachol (CCh) and 20 µM $E_{act}$. TMEM16A was inhibited by 30 µM $T16A_{inh}$-A01. Individual fluid bubbles marked with arrowheads. Scale bar: 0.5 mm. (bottom) CCh and $E_{act}$-induced secretion rates. Where indicated, tissues were pre-treated with $T16A_{inh}$-A01 (30 µM). Each point is the average of measurements made from 20 glands (mean±S.E. * P<0.05). FIG. 6C. Summary of human gland fluid secretion rates measured at 20 min after addition of 20 µM $E_{act}$, and 30 min after application of 300 nM carbachol (CCh) and 10 µM forskolin (20-66 glands from 3 tracheas and 4 bronchus). In CF-bronchi, 6 glands from one donor were stimulated by $E_{act}$.

FIG. 7A. Expression of TMEM16A in human salivary gland. (left) TMEM16A immunostaining in human parotid gland. Scale bar: 20 µm. (right) Immunoblot of TMEM16A in FRT-TMEM16A and A253 cells. FIG. 7B. Whole-cell patch-clamp recordings in A253 cells. (left) CaCC and TMEM16A chloride current induced by 100 µM ATP and 10 µM $E_{act}$, respectively. (right) Current/voltage (I/V) plot of mean currents at the middle of each voltage pulse (voltages between ±80 mV in steps of 20 mV).

FIG. 8A. Representative traces from mouse ileal segments showing effects of $T16A_{inh}$-A01 (10 µM), carbachol (CCh, 1 µM) and $E_{act}$ (10 µM). FIG. 8B. Effect of CCh (1 µM) and $E_{act}$ (10 µM) following atropine (1 µM). FIG. 8C. Summary of contraction frequency (left), and resting and maximum tone (right) (mean±S.E., n=4-7, * P<0.05).

FIG. 9. Representative current traces are illustrated, showing ATP-, $E_{act}$-, or $F_{act}$9-stimulated TMEM16A Cl⁻ current. Apical membrane current measured in TMEM16A-expressing FRT cells in the presence of a transepithelial chloride gradient and after basolateral membrane permeabilization.

DETAILED DESCRIPTION

Figure 1C:
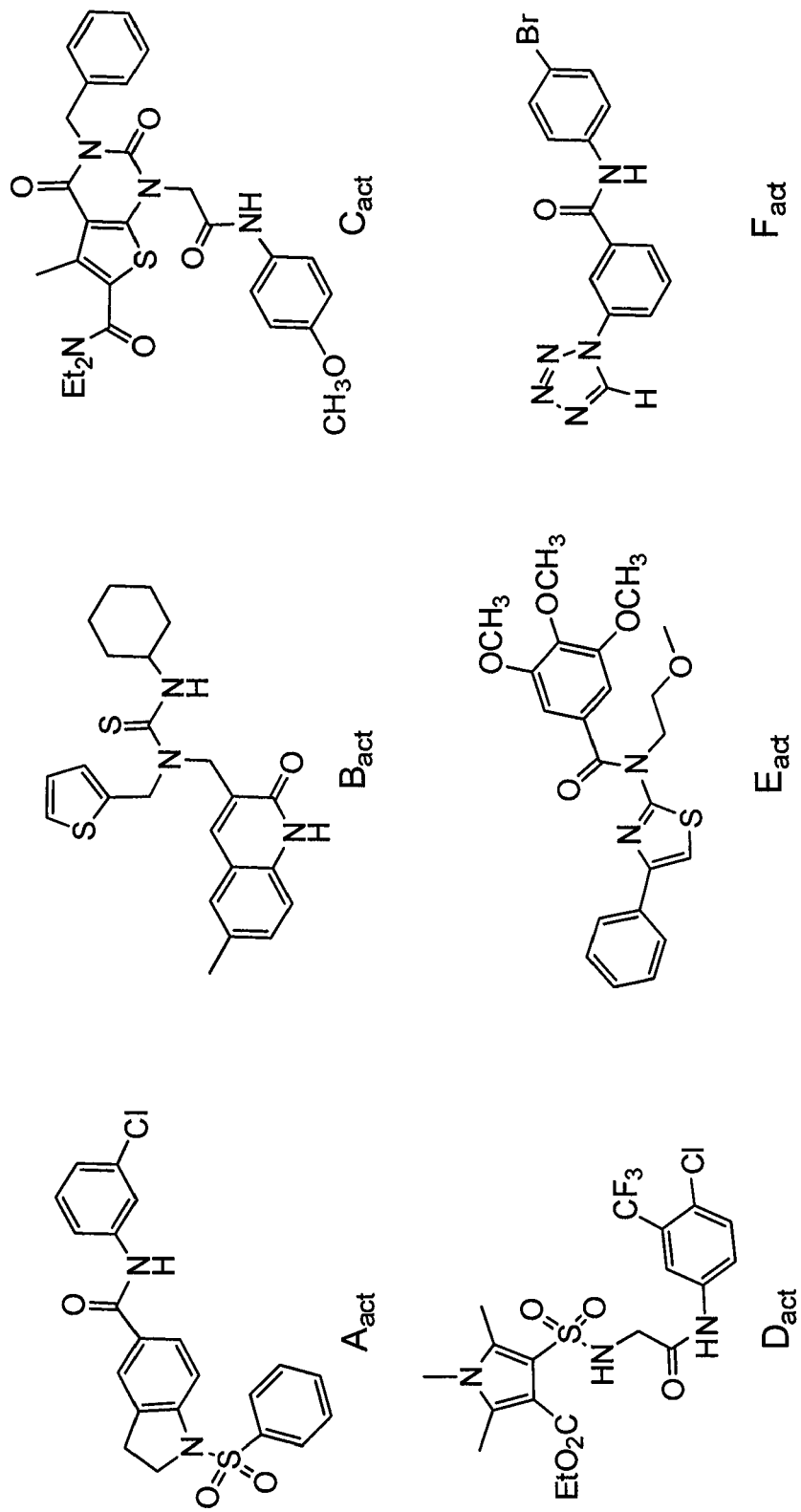

Small-molecule activators of calcium-activated chloride channels (CaCC) are described herein. These compounds include activators of the CaCC TMEM16A that target TMEM16A itself rather than upstream $Ca^{2+}$ signaling. The compounds described herein and compositions comprising these compounds provide potential drug candidates for treatment of salivary gland dysfunction, such as Sjogren's syndrome and salivary gland disorders following radiation injury, as well as for cystic fibrosis, dry eye syndrome, intestinal hypomotility, and other disorders treatable by activating a Cl⁻ channel (Verkman et al. (2009) *Nat. Rev. Drug. Discov.* 8, 153-171; Tabbara et al. (2000) *Curr Opin Ophthalmol* 11, 449-454). In cystic fibrosis, the rationale for CaCC activator therapy is the activation of alternative, non-CFTR chloride channels in airway epithelium where CFTR is dysfunctional. Two CaCC activator therapies for cystic fibrosis have been in clinical trials, including a $P2Y_2$ receptor antagonist (denufosol) (Kellerman et al. (2008) *Pulm. Pharmacol. Ther.* 21, 600-607), which acts through $Ca^{2+}$ elevation, and a bacterial polycyclic peptide (duramycin) (Steiner et al. (2008) *Naunyn. Schmiedebergs. Arch. Pharmacol.* 378, 323-333). A $P2Y_2$ receptor agonist is also in clinical trials for dry eye disease (Nichols et al. (2004) *Expert. Opin. Investig. Drugs.* 13, 47-54). CaCC activators that target CaCCs directly without cytoplasmic $Ca^{2+}$ elevation may offer more targeted therapy than general agonists of $Ca^{2+}$ signaling and, unlike receptor agonist therapy, could produce more sustained CaCC activation and hence offer greater efficacy. Small molecules described herein are TMEM16A-targeted activators that may be useful in treating cystic fibrosis, dry mouth, dry eye, salivary gland dysfunction or disorder, and intestinal hypomotility and other diseases and disorders described herein and in the art for which activation of CaCCs would be beneficial.

Calcium-activated Cl⁻ channels (CaCCs) are widely expressed in epithelial and non-epithelial cell types where they facilitate epithelial fluid secretion, smooth muscle contraction, neurosensory signaling, and other functions (Hartzell et al. (2005) *Annu. Rev. Physiol.* 67, 719-758; Verkman, A. S., and Galietta, L. J. (2009) *Nat. Rev. Drug. Discov.* 8, 153-171; Eggermont, J. (2004) *Proc. Am. Thorac. Soc.* 1, 22-27). TMEM16A (which is also known in the art as anoctamin-1, ANO1) was identified as a CaCC because its heterologous expression in oocytes and mammalian cells produced outwardly rectifying, $Ca^{2+}$-sensitive Cl⁻ currents (Yang et al. (2008) *Nature.* 455, 1210-1215; Caputo et al. (2008) *Science.* 322, 590-594; Schroeder et al. (2008) *Cell.* 134, 1019-1029). TMEM16A is expressed in epithelial cells in airways, salivary gland, intestine and other tissues, as well as in arterial smooth muscle, intestinal pacemaker cells, sensory neurons and various tumors (Yang supra; Ferrera et al., (2010) *Physiology (Bethesda).* 25, 357-363; Huang et al., (2009) *Proc. Natl. Acad. Sci. U.S.A.* 106, 21413-21418; Hwang et al. (2009) *J. Physiol.* 587, 4887-4904). Though TMEM16A knockout mice die just after birth because of tracheomalacia (Rock et al. (2008) *Dev. Biol.* 321, 141-149), electrophysiological measurements in the neonatal knockout mice suggested TMEM16A involvement in chloride secretion in salivary gland (Romanenko et al. (2010). *J. Biol. Chem.* 285, 12990-13001) and airway (Rock et al. (2009) *J. Biol. Chem.* 284, 14875-80) epithelia. Evidence has also been reported for TMEM16A involvement in intestinal and vascular smooth muscle contraction, nociception and bile formation (Hwang et al., supra; Dutta et al., (2009) *J. Biol. Chem.* 286, 766-776; Manoury et al. (2010) *J. Physiol.* 588, 2305-2314; Liu et al., (2010) *J. Clin. Invest.* 120, 1240-1252).

Small-molecule inhibitors of TMEM16A chloride conductance have recently been described. Some compounds, including tannic acid and related gallotannins (Namkung et al. (2010) *FASEB J.* 24, 4178-4186) and the arylaminothiophene $CaCC_{inh}$-A01 (De La Fuente et al. (2008) *Mol. Pharmacol.* 73, 758-768), function as non-selective CaCC inhibitors that inhibit TMEM16A and other, as yet unidentified, CaCC(s) in multiple cell types. See also International Application Publication No. WO 2009/079373. CaCC inhibition by gallotannins in red wines and green teas may account, in part, for their health benefits, including reduced risk of cardiovascular disease. TMEM16A-selective inhibitors were also identified, including the aminophenylthiazole $T16A_{inh}$-A01 (Namkung et al. (2011) *J. Biol. Chem.* 286, 2365-2374). $T16A_{inh}$-A01 inhibited CaCC Cl⁻ current in TMEM16A-transfected cells and in cultures of human salivary gland and IL-4 treated bronchial epithelia, but not in intestine, providing pharmacological data on TMEM16A involvement in CaCC function in various tissues.

TMEM16A (ANO1) is a calcium-activated chloride channel (CaCC) expressed in secretory epithelia, smooth muscle and other tissues. As described herein, cell-based functional screening of ~110,000 compounds revealed compounds that activated TMEM16A CaCC conductance without increasing cytoplasmic $Ca^{2+}$. The CaCC agonists described herein are activators (i.e., enhancers, stimulators, agonists) of the TMEM16A CaCC and include both types of compounds called herein 'activators' and 'potentiators,' which are terms used when discussing the mechanism of action and/or site to which the compounds bind on the CaCC. By patch-clamp, N-aroylaminothiazole 'activators' ($E_{act}$) strongly increased Cl⁻ current at zero (0) $Ca^{2+}$, whereas tetrazolylbenzamide 'potentiators' ($F_{act}$) were not active at zero (0) $Ca^{2+}$ but reduced the $EC_{50}$ for $Ca^{2+}$ dependent TMEM16A activation. Of 682 analogs tested, the most potent activator ($E_{act}$) and potentiator ($F_{act}$) produced large and more sustained CaCC Cl⁻ currents than general agonists of $Ca^{2+}$ signaling, with $EC_{50}$ 3-6 μM and CF conductance comparable to that induced transiently by $Ca^{2+}$-elevating purinergic agonists. Derivatives of activators were identified that acted as inhibitors, and fully inhibited TMEM16A Cl⁻ conductance, providing further evidence for direct TMEM16A binding by the compounds described herein. The TMEM16A activators increased CaCC conductance in human salivary and airway submucosal gland epithelial cells, and IL-4 treated bronchial cells, and stimulated submucosal gland secretion in human bronchi and smooth muscle contraction in mouse intestine. Small-molecule, TMEM16A-targeted activators may be useful for drug therapy of cystic fibrosis, dry mouth, salivary gland dysfunctions or disorders, and gastrointestinal hypomotility disorders, and may also be used for pharmacological dissection of TMEM16A function.

A functional, cell-based screen of small molecule collections revealed several chemical classes of TMEM16A activators that produced strong and more sustained Cl⁻ currents than $Ca^{2+}$-elevating purinergic agonists in multiple cell types without elevating cytoplasmic $Ca^{2+}$. As described herein, two classes of compounds with distinct activating mechanisms, 'activators' and 'potentiators', were identified. Though various agonists of cytoplasmic $Ca^{2+}$ have been available and studied in clinical trials, direct-acting CaCC modulators have not been reported previously. The more sustained CaCC activation produced by the compounds identified here could translate to improved efficacy compared to $Ca^{2+}$ agonists, such as $P2Y_2$ agonists, which generally produce only transient elevation in cytoplasmic $Ca^{2+}$ and, consequently, in Cl⁻ secretion. The recently reported Phase 3 trial of the $P2Y_2$ agonist denufosol (Kellerman et al. (2008) *Pulm. Pharmacol. Ther.* 21, 600-607), which failed to show clinical efficacy, may be related to its limited duration of action. In addition to producing more sustained activation of Cl⁻ conductance, direct-acting CaCC activators also have the theoretical advantage over $Ca^{2+}$ agonists of greater target specificity. (See also, e.g., Cheng et al. (2006) *J. Med. Chem.* 49, 1517-1525; Shipps et al. (2005) *Bioorg. Med. Chem. Lett.* 15, 115-119; Munchhof et al. (2009) *Bioorg. Med. Chem. Lett.* 19, 1428-1430; Lee et al. (2010) *Eur. J. Med. Chem.* 45, 5420-5427; Scheiff et al. (2010) *Bioorg. Med. Chem.* 18, 2195-2203; Stadelmann et al. (2010) *J. Antimicrob. Chemother.* 65, 512-519; Mokale et al. (2010) *Eur. J. Med. Chem.* 45, 3096-3100; Kawamatsu et al. (1981) *Eur. J. Med. Chem.* 16, 355-362).

The following N-aroylaminothiazole compounds and tetrazolylbenzamide compounds, and pharmaceutical compositions comprising these compounds that are CaCC activators may be useful for treating diseases and disorders treatable by activating a CaCC (e.g., TMEM16A), and thereby increasing CaCC conductance.

In one embodiment, provided herein is a compound of structure (I):

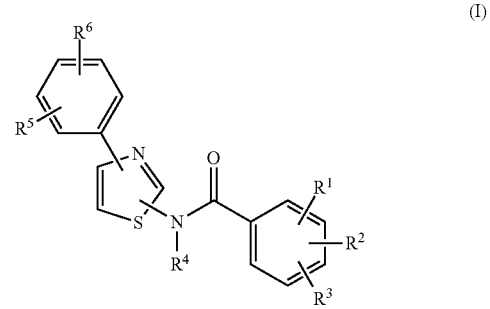

or a stereoisomer, tautomer, solvate, or pharmaceutically acceptable salt thereof,
wherein
$R^1$, $R^2$ and $R^3$ are each independently alkoxy;
$R^4$ is aralkyl, heteroaralkyl, heterocyclylalkyl, or alkoxyalkyl; and
$R^5$ and $R^6$ are each independently hydrogen, alkoxy, or halo.

In certain particular embodiments, the compound of structure (I) has the following structure (Ia):

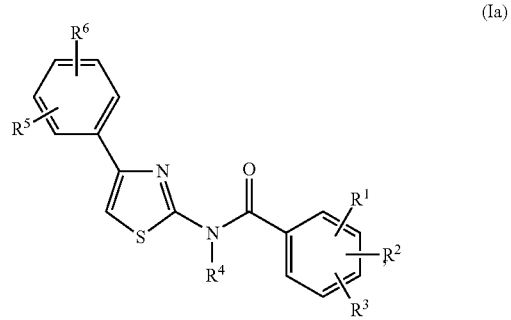

wherein each of $R^1$, $R^2$, $R^3$, $R^4$, $R^5$, and $R^6$ are the same as defined for structure (I).

In other embodiments, the compound of structure (I) has one of the following structures (Ib) or (Ic):

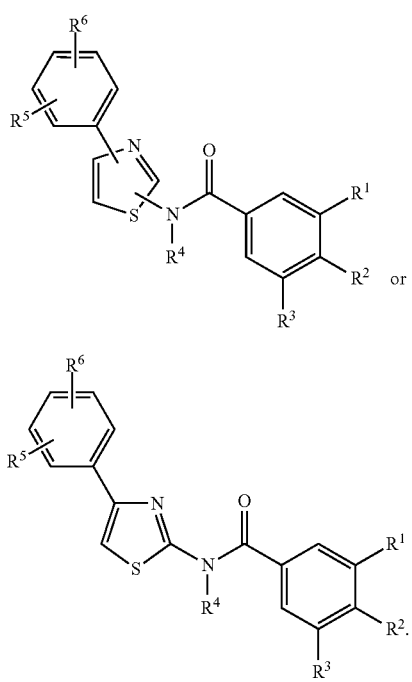

wherein each of $R^1$, $R^2$, $R^3$, $R^4$, $R^5$, and $R^6$ are the same as defined for structure (I).

In particular embodiments of structure (I), (Ia), (Ib) or (Ic), $R^1$, $R^2$, or $R^3$ are each independently $C_{1-6}$alkoxy; in other certain particular embodiments, $R^1$, $R^2$, or $R^3$ are each independently $C_{1-3}$alkoxy. In certain specific embodiments of structure (I), (Ia), (Ib) or (Ic), at least one of $R^1$, $R^2$, or $R^3$ is methoxy. In other specific embodiments, each of $R^1$, $R^2$, and $R^3$ is methoxy.

In yet other embodiments, the disclosure provides a compound of structure (I), (Ia), (Ib) or (Ic), wherein $R^4$ is a 6-membered heteroaralkyl or 6-membered heterocyclylalkyl. In other specific embodiments, $R^4$ is a 5- or 6-membered aralkyl, a 5- or 6-membered heteroaralkyl, or 5- or 6-membered heterocyclylalkyl. In particular embodiments, the heteroatom of the heteroaralkyl or the heterocyclylalkyl is N or O. In still other embodiments, the disclosure provides a compound of structure (I), (Ia), (Ib) or (Ic), wherein $R^4$ is benzyl, tetrahydrofuran-2-yl-methyl, furan-2-yl-methyl, 2-methoxyethyl (—$(CH_2)_2$—O—$CH_3$), tetrahydropyran-2-yl-methyl, pyrid-4-yl-methyl or pyrid-2-yl-methyl. For example, in yet further embodiments, $R^4$ is tetrahydropyranyl-methyl or pyridyl-methyl. In other certain embodiments, $R^4$ is tetrahydropyran-2-yl-methyl, pyrid-4-yl-methyl, or pyrid-2-yl-methyl.

In still other embodiments of the compound of structure (I), (Ia), (Ib) or (Ic), at least one of $R^5$ or $R^6$ is at the 4-position, and in other embodiments $R^5$ is at the 2-position and $R^6$ is at the 5-position. In other embodiments, at least one of $R^5$ or $R^6$ is hydrogen, and for example, in some embodiments, each of $R^5$ and $R^6$ is hydrogen. In yet other embodiments, at least one of $R^5$ or $R^6$ is methoxy, and in a more specific embodiment, each of $R^5$ and $R^6$ is methoxy. In still other embodiments, at least one of $R^5$ or $R^6$ is chloro. In certain specific embodiments, at least one of $R^5$ or $R^6$ is fluoro. In even more specific embodiments, $R^5$ is hydrogen and $R^6$ is methoxy. In other embodiments, $R^5$ hydrogen and $R^6$ is chloro, while in other embodiments $R^5$ is hydrogen and $R^6$ is fluoro.

In other embodiments of the compound of structure (I), the compound has one of the following structures:

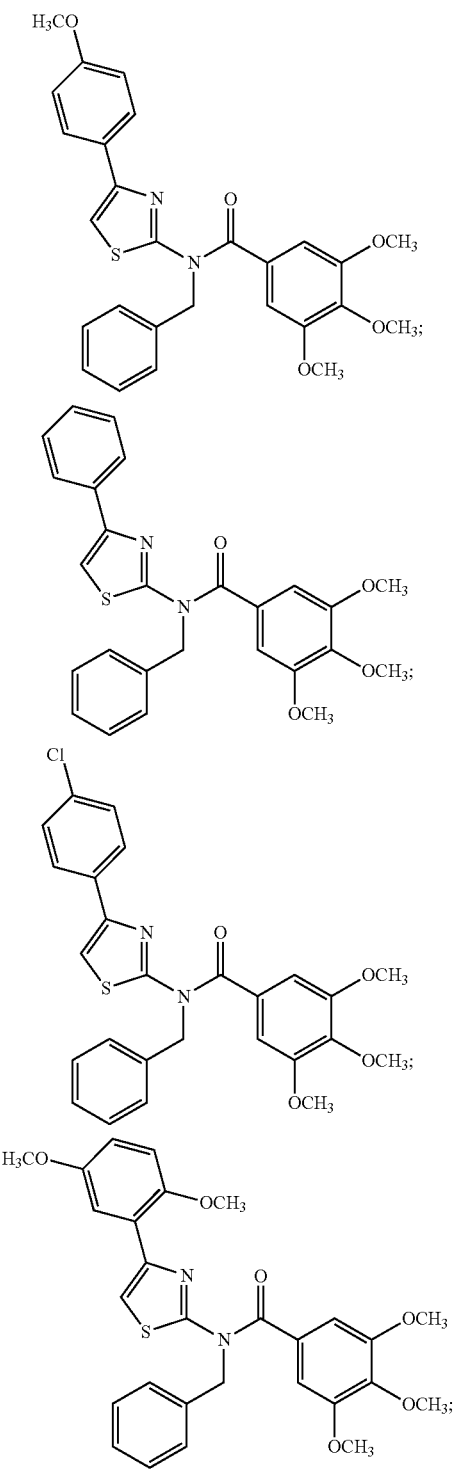

-continued
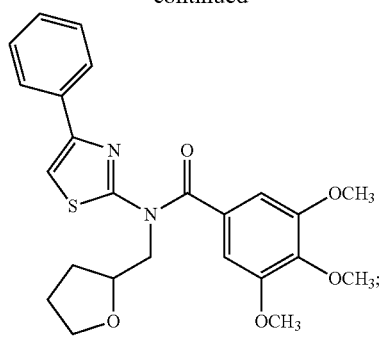
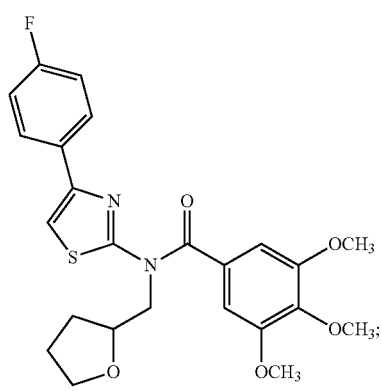
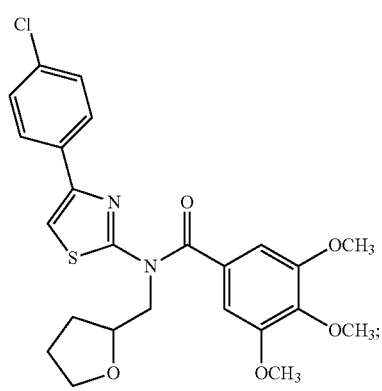
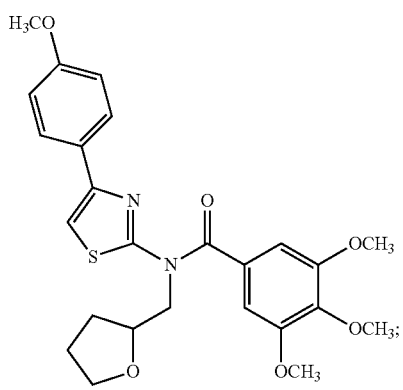
-continued
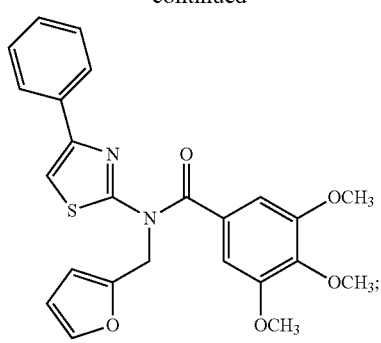
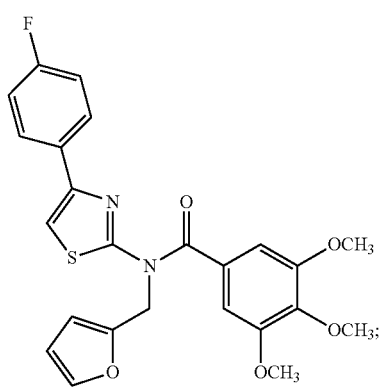
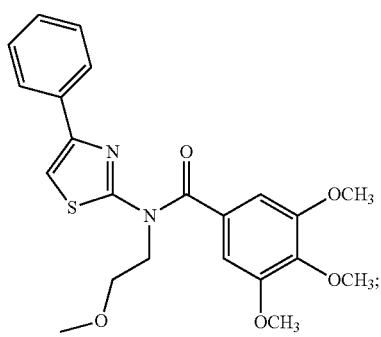
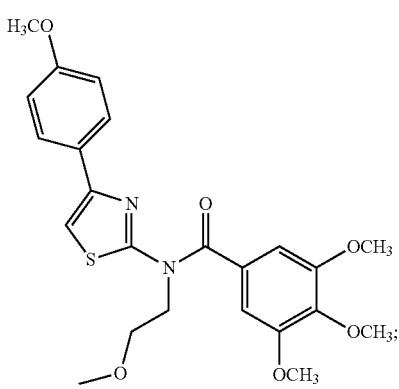

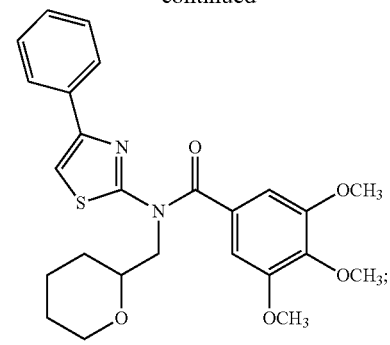

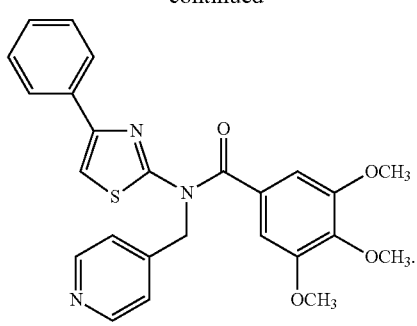

In another embodiment the present disclosure provides a compound of structure (II):

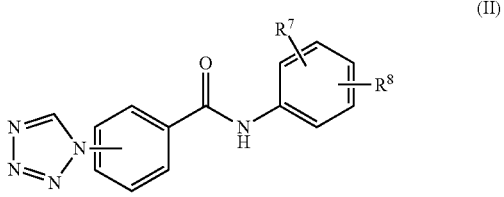

(II)

or a stereoisomer, tautomer, solvate, or pharmaceutically acceptable salt thereof,
wherein
R$^7$ is hydrogen or trifluoroalkyl; and
R$^8$ is bromo or alkyl.

In some certain embodiments of the compound of structure (II), when R$^8$ is bromo, R$^7$ is trifluoroalkyl.

In other embodiments of the compound of structure (II), the compound has the following structure (IIa):

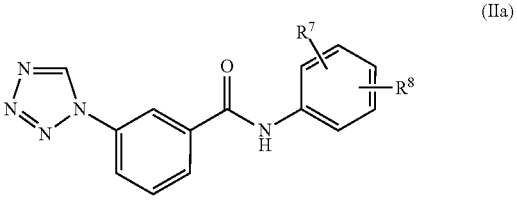

(IIa)

wherein R$^7$ and R$^8$ are defined as above for a compound of structure (II).

In yet other embodiments, the compound of structure (II) has one of the following structures (IIb) or (IIc):

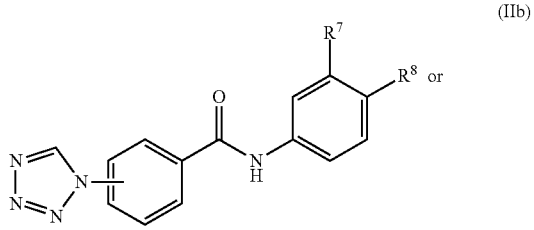

(IIb)

In still other embodiments, the compound of structure (I) has one of the following structures:

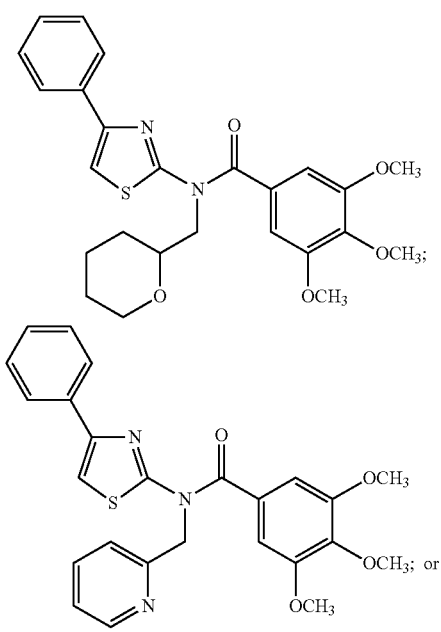

-continued (IIc)

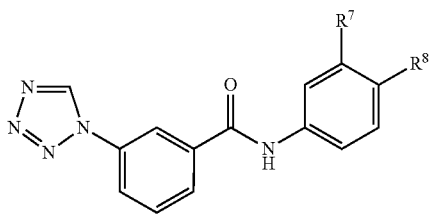

wherein R⁷ and R⁸ are defined as above for a compound of structure (II).

In certain embodiments of the compound of structure (II), (IIa), (IIb) or (IIc), R⁷ is hydrogen. In other embodiments, R⁷ is —CF₃.

In some other embodiments of the compound of structure (II), (IIa), (IIb) or (IIc), R⁸ is bromo. In certain embodiments, R⁸ is C$_{1-6}$ alkyl, and in other certain embodiments, R⁸ is C$_{1-3}$ alkyl. In a particular embodiment, R⁸ is isopropyl. In other particular embodiments, R⁸ is alkyl with the proviso that when R⁷ is H, R⁸ is not isopropyl (i.e., -2-propyl) at the 4 position.

In other embodiments of the compound of structure (II), the compound has one of the following structures:

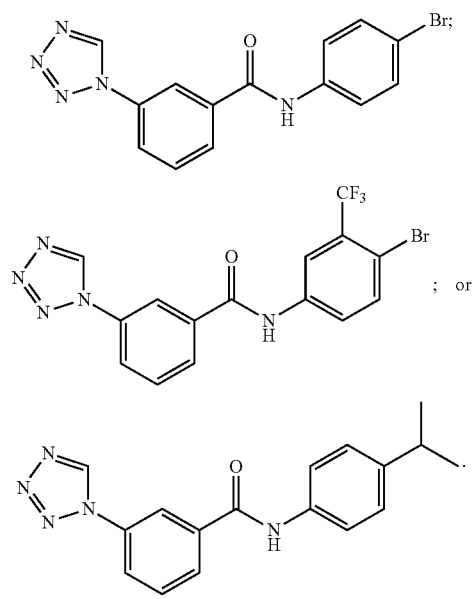

In other specific embodiments, the compound of structure (II) has one of the following structures:

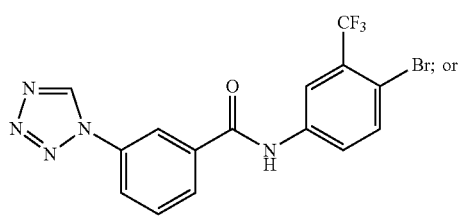

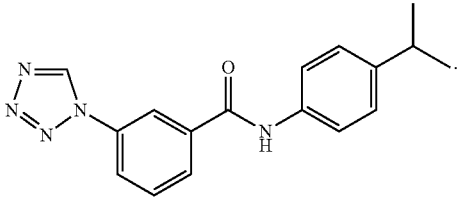

In still other embodiments, the present disclosure provides a method for treating a disease or condition treatable by activating a calcium-activated chloride ion channel in a subject, the method comprising administering a pharmaceutical composition comprising a pharmaceutically acceptable excipient and any one or more of the foregoing compounds of structure (I) or (II) to the subject. In certain embodiments of the foregoing method, the calcium-activated chloride ion channel is TMEM16A.

In other embodiments, the disease or condition to be treated is salivary gland dysfunction, cystic fibrosis, dry eye syndrome, dry mouth, or intestinal hypomotility. In certain specific embodiments the salivary gland dysfunction is Sjogren's syndrome. In other embodiments, the salivary gland dysfunction is caused by radiation injury.

In yet other embodiments, the current disclosure provides a method for treating a disease or condition treatable by activating a calcium-activated chloride ion channel in a subject, the method comprising administering sequentially in either order or concurrently (a) a pharmaceutical composition comprising a pharmaceutically acceptable excipient and any one or more of the foregoing compounds of structure (I) and (b) a pharmaceutical composition comprising a pharmaceutically acceptable excipient and any one or more of the foregoing compounds of structure (II).

In some embodiments of the foregoing method, the calcium-activated chloride ion channel is TMEM16A.

In other embodiments, the disease or condition is salivary gland dysfunction, cystic fibrosis, dry eye syndrome, dry mouth, or intestinal hypomotility. For example, in some embodiments the salivary gland dysfunction is Sjogren's syndrome. In other embodiments, the salivary gland dysfunction is caused by radiation injury.

As discussed in greater detail herein, also provided are pharmaceutical compositions comprising any one or more of the above-described N-aroylaminothiazole compounds and (i.e., the compounds of structure I and substructures ((Ia), (Ib), and (Ic), and specific compounds) and tetrazolylbenzamide compounds (i.e., the compounds of structure (II), ((IIa), (IIb), and (IIc), and specific compounds) and a pharmaceutically (i.e., physiologically) suitable (i.e., acceptable) excipient (such as a diluent, carrier, or adjuvant), which may be used in the methods described herein. The N-aroylaminothiazole and tetrazolylbenzamide compounds having the structures described herein are capable of activating (i.e., increasing, enhancing, stimulating) CaCC-mediated ion transport (i.e., activating in a statistically significant, clinically significant, and/or biologically significant manner), for example, activating TMEM16A-mediated chloride ion (i.e., Cl⁻) transport. In other embodiments provided herein, the N-aroylaminothiazole and tetrazolylbenzamide compounds and compositions comprising these compounds described above and herein may be used in methods for treating a disease, condition, or disorder that is treatable by activating CaCC-mediated ion transport. Exemplary diseases, conditions, and disorders include, but are not limited to, salivary gland dysfunction (such as Sjogren's syndrome, salivary gland disorders following radiation injury, dry mouth), as well as for cystic fibrosis, dry eye syndrome, intestinal hypomotility, and other disorders for which activating a Cl⁻ channel would be beneficial. Each of these methods and uses is described in greater detail herein.

Without wishing to be bound by any particular theory, the action of the compounds described herein (i.e., $E_{act}$ and $F_{act}$ compounds) may involve direct interaction with the TMEM16A protein because these compounds did not elevate cytoplasmic $Ca^{2+}$ and were effective in patch-clamp studies in which $[Ca^{2+}]$ was clamped by the pipette solution (see Examples). Further, the generation of TMEM16A inhibitors by minor structural modification of activators strongly support a direct binding mechanism. Based on the assumed topography and domain structure of TMEM16A (Yang et al., supra), the 'activator' N-aroylaminothiazole compounds ($E_{act}$) may interact at or very near the $Ca^{2+}$ binding site, perhaps at the cluster of four contiguous glutamic acid residues localized in the first intracellular loop (Ferrera et al., supra). The 'potentiator' tetrazolylbenzamide compounds ($F_{act}$), which increased the $Ca^{2+}$-sensitivity of TMEM16A activation, might act by an allosteric mechanism at a site distinct from the $Ca^{2+}$ binding site.

Definitions

The terms below, as used herein, have the following meanings, unless indicated otherwise. Certain chemical groups named herein are preceded by a shorthand notation indicating the total number of carbon atoms that are to be found in the indicated chemical group. For example, $C_{1-6}$ alkyl (or $C_1$-$C_6$ alkyl) describes an alkyl group, as defined below, has a total of 1, 2, 3, 4, 5, or 6 carbon atoms. Similarly, $C_{1-3}$ alkyl (or $C_1$-$C_3$ alkyl) describes an alkyl group, as defined below, has a total of 1, 2, or 3 carbon atoms. By way of additional example, $C_{1-20}$ alkyl (or $C_1$-$C_{20}$ alkyl) describes an alkyl group, as defined below, has a total of any number of carbon atoms between 1 and 20 (i.e., 1, 2, 3, 4, 5, 6, 7, 8, 9, 10, 11, 12, 13, 14 15, 16, 17, 18, 19, or 20 carbon atoms). The total number of carbons in the shorthand notation does not include carbons that may exist in substituents of the group described. In addition to the foregoing, as used herein, unless specified to the contrary, the following terms have the meaning indicated.

"Alkyl" means a straight chain or branched, noncyclic or cyclic, saturated aliphatic hydrocarbon. An alkyl group as described herein has from one to 12 carbon atoms, and which group is attached to the rest of the molecule by a single bond. Alkyls comprising any number of carbon atoms from 1 to 12 are included. An alkyl comprising up to 12 carbon atoms is referred to as a $C_1$-$C_{12}$ alkyl. Alkyls comprising other numbers of carbon atoms are represented similarly. Representative saturated straight chain alkyls include methyl, ethyl, n-propyl, n-butyl, n-pentyl, n-hexyl, and the like, while saturated branched alkyls include isopropyl (1-methylethyl), sec-butyl, isobutyl, tert-butyl (1,1-dimethylethyl or t-butyl), i-butyl, s-butyl, n-pentyl, isopentyl, 3-methylhexyl, 2-methylhexyl and the like. Representative saturated cyclic alkyls (e.g., $C_{3-20}$ cycloalkyl) include cyclopropyl, cyclobutyl, cyclopentyl, cyclohexyl, —CH₂cyclopropyl, —CH₂cyclobutyl, —CH₂cyclopentyl, —CH₂cyclohexyl, and the like. Cyclic alkyls, also referred to as "homocyclic rings," include di- and poly-homocyclic rings such as decalin and adamantyl. Alkyl groups include, but are not limited to, those represented by the following nomenclature: $C_1$-$C_{12}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, and $C_4$-$C_8$ alkyl.

An unsaturated straight or branched hydrocarbon chain radical group may contain at least one double bond or triple bond between adjacent carbon atoms and is referred to as an "alkenyl" or "alkynyl," respectively. Representative straight chain and branched alkenyls (e.g., $C_{2-12}$ alkenyl or $C_{2-6}$ alkenyl) include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. In the art, exemplary alkenyl groups may also be called ethenyl, prop-1-enyl, but-1-enyl, pent-1-enyl, penta-1,4-dienyl. In other embodiments, an alkenyl may comprise two to four carbon atoms. The alkenyl is connected to the rest of the molecule by a single bond, for example, ethenyl (i.e., vinyl), prop-1-enyl (i.e., allyl), but-1-enyl, pent-1-enyl, penta-1,4-dienyl, and the like. Representative straight chain and branched alkynyls (e.g., $C_{2-12}$ or $C_{2-6}$ alkynyl) include acetylenyl, propynyl, 1-butynyl, 2-butynyl, 1-pentynyl, 2-pentynyl, 3-methyl-1 butynyl, and the like. In the art, exemplary alkynyl groups may also be called ethynyl, but-2-ynyl, but-3-ynyl, pentynyl, hexynyl, and the like.

Unless stated otherwise specifically in the specification, an alkyl, alkenyl, or alkynyl group may be optionally substituted as described below. By way of example, "optionally substituted alkyl," encompasses unsubstituted alkyl and substituted alkyl as defined herein.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —OR$_a$ where R$_a$ is an alkyl radical as defined herein. Unless stated otherwise specifically in the specification, an alkoxy group may be optionally substituted as described below. $C_{1-6}$ alkoxy (or $C_1$-$C_6$ alkoxy) describes an alkoxy group that has a total of 1, 2, 3, 4, 5, or 6 carbon atoms and means that the alkyl moiety is $C_{1-6}$ alkyl. Similarly, $C_{1-3}$ alkoxy (or $C_1$-$C_3$ alkoxy) describes an alkoxy group that has a total of 1, 2, or 3 carbon atoms and means that the alkyl moiety is $C_{1-3}$ alkyl.

"Alkoxyalkyl" refers to a radical of the formula —R$_b$OR$_a$ where R$_a$ is an alkyl radical as defined and where R$_b$ is an alkylene radical as defined. Unless stated otherwise specifically in the specification, an alkoxyalkyl group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Halo" or "halogen" refers to bromo, chloro, fluoro or iodo.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; nitrogen, carbon or sulfur atom(s) in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5,18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heterocyclylalkyl" refers to a radical of the formula —$R_b$-$R_c$ where $R_b$ is an alkylene chain as defined above and $R_c$ is one or more heterocyclyl radicals as defined above, for example, tetrahydrofuranyl-methyl, tetrahydropyranyl-methyl and the like. A 6-membered heterocyclylalkyl refers to a heterocyclylalkyl, wherein the heterocyclyl moiety has 6 atoms in the ring. Unless stated otherwise specifically in the specification, a heterocyclalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"Heteroarylalkyl" refers to a radical of the formula —$R_b$-$R_c$ where $R_b$ is an alkylene chain as defined above and $R_c$ is one or more heteroaryl radicals as defined above, for example, furanyl-methyl, pyridyl-methyl and the like. A 6-membered heteroarylalkyl refers to a heteroarylalkyl, wherein the heteroaryl moiety has 6 atoms in the ring. Unless stated otherwise specifically in the specification, a heteroarylalkyl group may be optionally substituted.

"Trifluoroalkyl" refers to an alkyl group as defined above, wherein at three hydrogen atoms have been replaced with fluoro moieties. Trifluoroalkyls include trifluoromethyl and the like.

All the above groups may be either substituted or unsubstituted. The term "substituted" as used herein means any of the above groups (i.e., alkyl, alkylene, alkoxy, alkoxyalkyl, aryl, aralkyl, heterocyclyl, heterocyclylalkyl, heteroaryl, heteroarylalkyl and/or trifluoroalkyl), may be further functionalized wherein at least one hydrogen atom is replaced by a bond to a non-hydrogen atom substituent. Unless stated specifically in the specification, a substituted group may include one or more substituents selected from: oxo, —$CO_2H$, nitrile, nitro, —$CONH_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(\!=\!O)NR_gR_h$, —$NR_gC(\!=\!O)OR_h$, —$NR_gSO_2R_h$, —$OC(\!=\!O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(\!=\!O)R_g$, —$C(\!=\!O)OR_g$, —$CH_2SO_2R_g$, —$CH_2SO_2NR_gR_h$, —SH, —$SR_g$ or —$SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of Structures I and II and substructures thereof, as well as any and all substructures and specific compounds described herein is intended to encompass any and all pharmaceutically suitable salt forms.

Compounds of Structures I and II and substructures thereof may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

"Prodrug" is meant to indicate a compound that may be converted under physiological conditions or by solvolysis to a biologically active compound as described herein. Thus, the term "prodrug" refers to a metabolic precursor of a compound described herein that is pharmaceutically acceptable. A prodrug may be inactive when administered to a subject in need thereof, but is converted in vivo to an active compound. Prodrugs are typically rapidly transformed in vivo to yield the parent compound, for example, by hydrolysis in blood. The prodrug compound often offers advantages of solubility, druggability, tissue compatibility or delayed release in a mammalian organism (see, e.g., Bundgard, H., Design of Prodrugs (1985), pp. 7-9, 21-24 (Elsevier, Amsterdam). A discussion of prodrugs is also provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a subject. Prodrugs of a compound described herein may be prepared by modifying functional groups present in the compound in such a way that the modifications are cleaved, either in routine manipulation or in vivo, to the parent compound. Prodrugs include compounds described herein, wherein a hydroxy, amino, or mercapto group is bonded to any group that, when the prodrug of the compound is administered to a subject, cleaves to form a free hydroxy, free amino, or free mercapto group, respectively. Examples of prodrugs include, but are not limited to, acetate, formate, and benzoate derivatives of alcohol or amine functional groups in the compounds and the like.

With regard to stereoisomers, the compounds of structure (I) and structure (II), as well as any sub-structure herein, may have one or more chiral (or asymmetric) centers, for example, in any of $R^1$-$R^8$, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are nonsuperimposeable mirror images of one another. Thus, the compounds may occur in any isomeric form, including racemates, racemic mixtures, and as individual enantiomers or diastereomers. A tautomer refers to a proton shift from one atom of a molecule to another atom of the same molecule. All such isomeric forms of the compounds are included and contemplated, as well as mixtures thereof.

Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations,"

2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Compound Synthesis Procedures

Synthesis of the N-aroylaminothiazole compounds (i.e., the compounds of structure I and substructures ((Ia), (Ib), and (Ic), and specific compounds) and tetrazolylbenzamide compounds (I.e., the compounds of structure (II), ((IIa), (III)), and (IIc), and specific compounds) may be performed as described herein, including the Examples, using techniques familiar to a person skilled in the art. Examples 1 and 2 herein describe methods for synthesis of the N-aroylaminothiazole compounds described herein, and alternative methods are provided in Examples 4-6. These methods may be used for synthesis of the compounds of structure (I) by using appropriate reactants for preparation of the specific compound using the techniques and methods described herein, and that are routinely practiced in the art. The methods and techniques described in Example 3 and in Examples 6 and 7 may be used for preparation of a tetrazolylbenzamide compound of structure (II). These methods may be used for synthesis of the compounds of structure (II) by using appropriate reactants for preparation of the specific compound using the techniques and methods described herein, and that are routinely practiced in the art. By way of example, FIG. 3 provides a schematic of an N-aroylaminothiazole compound (called $E_{act}$) and a tetrazolylbenzamide compound (called $F_{act}$). See also Example 11.

Methods of Using and Characterizing N-Aroylaminothiazole and Tetrazolylbenzamide Compounds and Compositions Comprising the Compounds As described in greater detail herein, pharmaceutical compositions are provided, wherein the pharmaceutical compositions comprise a pharmaceutically suitable excipient (i.e., a pharmaceutically acceptable excipient or a physiologically suitable or acceptable excipient) and at least one of the N-aroylaminothiazole compounds (i.e., the compounds of structure I and substructures ((Ia), (Ib), and (Ic), and specific compounds) or at least one of the tetrazolylbenzamide compounds (i.e., the compounds of structure (II), ((IIa), (IIb), and (IIc), and specific compounds). In certain embodiments, at least one of the N-aroylaminothiazole compounds and at least one of the tetrazolylbenzamide compounds are administered concurrently or sequentially to a subject in need thereof. The N-aroylaminothiazole compounds and the tetrazolylbenzamide compounds described herein are capable of activating CaCC activity (i.e., increasing, enhancing, improving, or stimulating) transport of chloride ion in the CaCC channel or pore in a statistically, clinically and/or biologically significant manner) in a cell and therefore may be used for treating diseases, disorders, and conditions that are treatable by activating CaCC (e.g., TMEM16A) activity, which increases or enhances chloride ion transport. Such diseases, disorder, and conditions include those that result from or are related to dysfunctional CaCC activity (e.g., salivary gland dysfunction). Accordingly, methods of activating ion transport (e.g., increasing or enhancing chloride ion transport) by a CaCC are provided herein.

In one embodiment, a method is provided for treating a disease, disorder, or condition that is treatable by activating CaCC-mediated ion transport. In certain embodiments, such a disease, disorder, or condition is associated with aberrantly decreased CaCC-mediated ion transport or wherein tissue has been destroyed (e.g., salivary gland dysfunction subsequent to radiation injury). In other embodiments, methods are provided for treating diseases, disorders, or conditions that may be treated by activating (i.e., stimulating, enhancing, increasing) CaCC-mediated ion transport (such as but not limited to cystic fibrosis). Accordingly, in a specific embodiment, a method is provided for treating a disease, condition, or disorder treatable by activating CaCC, wherein the method comprises administering to a subject in need thereof a pharmaceutically suitable excipient and at least one of the N-aroylaminothiazole compounds and/or at least one of the tetrazolylbenzamide compounds described herein (i.e., a pharmaceutical composition as described herein), wherein ion transport mediated by the CaCC is increased or enhanced. In certain embodiments, the disease, disorder or condition is salivary gland dysfunction, cystic fibrosis, dry eye syndrome, dry mouth, or intestinal hypomotility. In more specific embodiments, the salivary gland dysfunction is dry mouth, Sjogren's syndrome, or results from salivary gland radiation injury, which may occur for example during radiation therapy of salivary gland cancer or other throat and mouth cancers.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the at least one N-aroylaminothiazole compound and/or at least one or more tetrazolylbenzamide compounds in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

As well understood by a person skilled in the art, treatment regimen (e.g., dose, frequency of dose, special instructions (e.g., administer with food, before intake of food, after intake of food)), induction and extent of any adverse effect or any toxic effect, and other safety and efficacy parameters may be accomplished by designing and carrying out pre-clinical (i.e., non-human animal studies and/or in vitro studies) and clinical studies. Typically, the results of such studies are evaluated and analyzed by appropriate statistical methods.

Dry mouth due to salivary gland dysfunction is seen following radiation therapy for head and neck cancers, in Sjogren's syndrome, and most commonly, with unknown (idiopathic) etiology. Dry eye (keratoconjunctivis sicca) is a related disorder that is very common in the elderly, which results from lacrimal or Meibomian gland dysfunction. TMEM16A is the major ion channel regulating saliva secretion by salivary gland acinar epithelial cells (Romanenko et al., supra). As such, TMEM16A activators are predicted to potentiate, or amplify, endogenous cholinergic signals to maximize saliva secretion from functional salivary gland acini. Because Cl⁻ and saliva fluid secretion require activity of basolateral membrane $K^+$ channels, TMEM16A-targeted activators are potentially advantageous over non-selective $Ca^{2+}$-elevating agonists as they would primarily amplify the effect of physiological stimuli rather than cause fluid secretion on their own.

Interstitial cells of Cajal (ICC) generate slow-wave pacemaker activity in smooth muscle in the gastrointestinal (GI) tract. TMEM16A is expressed in ICC but not in the GI smooth muscle cells (Huang et al., supra; Hwang et al., supra; Kashyap et al. (2011) *Neurogastroenterol. Motil. doi:* 10.1111/j.1365-2982.2011.01729.x.). A recent report showed that pharmacological inhibition or genetic deletion of TMEM16A abolished slow waves in murine small intestine (Hwang et al., supra). As described in the Examples, the TMEM16A-selective inhibitor T16A$_{inh}$-01 greatly reduced smooth muscle contraction in mouse intestine ex vivo, and a TMEM16A activator compound increased contraction, restoring contraction following atropine inhibition. Without wishing to be bound by theory, GI smooth muscle motility may be modulated by pharmacological activation or inhibition of TMEM16A, and TMEM16A may be involved in the regulation of intestinal smooth muscle contractility and other CaCCs in the regulation of contraction frequency. TMEM16A activators may be useful for treating GI motility disorders such as slow transit constipation, and may be useful for treating of disorders associated with hypermotility, wherein the compounds act to inhibit hypermotility. Of interest, TMEM16A modulators changed the strength but not the frequency of intestinal smooth muscle contraction. Pharmacological inhibition of CaCCs by non-specific inhibitors of CaCCs (for example, niflumic acid, DIDS) reduced the frequency and blocked slow waves in murine intestine (Hwang et al., supra).

In particular embodiments of the methods described herein, the subject is a human or non-human animal. A subject in need of the treatments described herein may exhibit symptoms or sequalae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In one embodiment, compounds and compositions described herein may be used for treating subjects who have cystic fibrosis. Cystic fibrosis is a lethal genetic disease afflicting approximately 30,000 individuals in the United States. Approximately 1 in 2500 Caucasians is born with the disease, making it the most common lethal, recessively inherited disease in that population.

Cystic fibrosis affects the secretory epithelia of a variety of tissues, altering the transport of water, salt, and other solutes into and out of the blood stream. In particular, the ability of epithelial cells in the airways, liver, pancreas, small intestine, reproductive tract and other tissues to transport chloride ions, and accompanying sodium and water, is severely reduced in cystic fibrosis patients, resulting in respiratory, pancreatic and intestinal ailments. The principle clinical manifestation of cystic fibrosis is the resulting respiratory disease, characterized by airway obstruction due to the presence of thick mucus that is difficult to clear from airway surfaces. This thickened airway liquid contributes to recurrent bacterial infections and progressively impairs respiration, eventually resulting in death.

In cystic fibrosis, defective chloride transport is generally due to a mutation in a chloride channel known as the cystic fibrosis transmembrane conductance regulator (CFTR; see Riordan et al., *Science* 245:1066-73, 1989). As described herein, the compounds and compositions comprising these compounds may be used to activate CaCC activity to ameliorate the symptoms and sequalae of cystic fibrosis.

Pharmaceutical Compositions and Methods of Using Pharmaceutical Compositions

Also provided herein are pharmaceutical compositions comprising any one or more of the N-aroylaminothiazole compounds and/or one or more of the tetrazolylbenzamide compounds of structure I and structure II, respectively (and substructures and specific structures thereof). The compounds described herein may be formulated in a pharmaceutical composition for use in treatment or preventive (or prophylactic) treatment (e.g., reducing the likelihood of occurrence or exacerbation of disease or one or more symptoms of the disease).

In pharmaceutical dosage forms, any one or more of the compounds of structure I or structure II, substructures, and specific structures described herein may be administered in the form of a pharmaceutically acceptable derivative, such as a salt, or they may also be used alone or in appropriate association, as well as in combination, with other pharmaceutically active compounds. The methods and excipients described herein are merely exemplary and are in no way limiting. An effective amount or therapeutically effective amount refers to an amount of a compound or a composition comprising one or more compounds administered to a subject, either as a single dose or as part of a series of doses, which is effective to produce a desired therapeutic effect.

Optimal doses may generally be determined using experimental models and/or clinical trials. The optimal dose may depend upon the body mass, weight, or blood volume of the subject. In general, the amount of a compound described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising at least one of the compounds described herein for treating a disease or condition may depend upon the subject's condition, that is, stage of the disease, severity of symptoms caused by the disease, general health status, as well as age, gender, and weight, and other factors apparent to a person skilled in the medical art. Similarly, the dose of the compound for treating a disease or disorder treatable by activating CaCC as described herein may be determined according to parameters understood by a person skilled in the medical art.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least compound as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein that comprise at least one of the N-aroylaminothiazole compounds and/or at least one of the tetrazolylbenzamide compounds of structure I and structure II, respectively (and substructures and specific structures thereof) may be administered to a subject in need by any one of several routes that effectively deliver an effective amount of the compound. Such administrative routes include, for example, oral, parenteral, enteral, rectal, intranasal, buccal, sublingual, intramuscular, and transdermal.

As described herein, methods are described wherein at least one N-aroylaminothiazole compound of structure I (and substructures and specific structures) and at least one tetrazolylbenzamide structure II (and substructures and specific structures) are administered concurrently or sequentially (i.e., one compound is administered prior to or subsequent to the other compound). For concurrent administration, the compounds may be formulated in the same pharmaceutical composition or each compound may be formulated separately into separate pharmaceutical compositions, which may further comprise one or more of the same pharmaceutically acceptable excipients. When the compounds are formulated in separate compositions, such compositions may be referred to as a first pharmaceutical composition and a second pharmaceutical composition, for convenience. A composition comprising at least a first pharmaceutical composition and a second pharmaceutical composition may also be called a preparation. When at least one N-aroylaminothiazole compound of structure I (and substructures and specific structures) and at least one tetrazolylbenzamide structure II (and substructures and specific structures) are administered sequentially, the compounds are formulated into separate pharmaceutical compositions (which may be called herein a first pharmaceutical composition and a second pharmaceutical composition and which may be described as being the components of a preparation). For each of concurrent administration when the compounds are formulated into separate pharmaceutical compositions and sequential administration, the compositions may be administered by the same route or by different routes, which routes are described herein. When the compounds are administered sequentially, the time interval between each administration of the different compositions comprising the respective compounds can be determined in clinical trials by person skilled in the art.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and*

*Practice of Pharmacy* (Gennaro, 21$^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, at least one of the compounds described herein can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

The CaCC activating compounds described herein can be formulated in pharmaceutical compositions as suppositories by mixing with a variety of bases such as emulsifying bases or water-soluble bases. These compounds may be administered rectally via a suppository. The suppository can include vehicles such as cocoa butter, carbowaxes and polyethylene glycols, which melt at body temperature, yet are solidified at room temperature.

Any of the N-aroylaminothiazole compounds and tetrazolylbenzamide compounds described herein may be used in aerosol formulation to be administered via inhalation. The compounds may be formulated into pressurized acceptable propellants such as dichlorodifluoromethane, propane, nitrogen and the like.

Any one or more of the N-aroylaminothiazole compounds and/or any one or more of the tetrazolylbenzamide compounds described herein may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a N-aroylaminothiazole compound or tetrazolylbenzamide compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5): 655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228 (1-2):99-107; Suzuki et al., *Biol. Pharm. Bull.* 2001; 24(6):698-700; Alberti et al., *J. Control Release* 2001; 71(3):319-27; Goldstein et al., *Urol-* ogy 2001; 57(2):301-5; Kiijavainen et al., *Eur. J. Pharm. Sci.* 2000; 10(2):97-102; and Tenjarla et al., *Int. J. Pharm.* 1999; 192(2):147-58.

When a N-aroylaminothiazole compounds or tetrazolylbenzamide compound is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. An N-aroylaminothiazole compound or tetrazolylbenzamide compound may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Also provided herein are methods of manufacturing the pharmaceutical compositions described herein that comprise at least one of the N-aroylaminothiazole compounds and/or at least one of the tetrazolylbenzamide compounds, as described herein. In one embodiment, the method of manufacture comprises synthesis of the compound. Synthesis of one of more of the compounds described herein may be performed according to methods described herein and practiced in the art. In another method of manufacture, the method comprises comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound, formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Methods for Characterizing and Using the N-Aroylaminothiazole and Tetrazolylbenzamide Compounds Also provided herein are methods that are useful, for example, for characterizing the potency of the N-aroylaminothiazole compounds and the tetrazolylbenzamide compounds (and derivatives and analogs thereof) to activate CaCC-mediated ion transport (particularly TMEM16A-mediated chloride ion transport); for monitoring the level (i.e., for example, concentration level, mass level, or $EC_{50}$ level) of a N-aroylaminothiazole and/or tetrazolylbenzamide compound that has been administered to a subject.

In certain embodiments, these methods may be performed in vitro, such as with using a biological sample as described herein that comprises, for example, cells obtained from a tissue, body fluid, or culture-adapted cell line, or other biological source as described in detail herein below. The step of contacting refers to combining, mixing, or in some manner familiar to persons skilled in the art that permits the compound and the cell to interact such that any effect of the compound on CaCC activity (e.g., the capability of a N-aroylaminothiazole compound or tetrazolylbenzamide compound to activate CaCC ion conductance or the level to which the compound increases CaCC ion transport) can be measured according to methods described herein and routinely practiced in the art. Methods described herein for activating ion transport by CaCC are understood to be performed under conditions and for a time sufficient that permit the CaCC (e.g., TMEM16A) and the compound to interact. Additional N-aroylaminothiazole and tetrazolylbenzamide compounds may be identified and/or characterized by such a method of activating ion transport by CaCC, performed with isolated cells in vitro. Conditions for a particular assay include temperature, buffers (including salts, cations, media), and other components that maintain the integrity of the cell and the compound, which a person skilled in the art will be familiar and/or which can be readily determined. A person skilled in the art also readily appreciates that appropriate controls can be designed and included when performing the in vitro methods and in vivo methods described herein.

Methods for characterizing the compounds described herein, for determining an effective concentration to achieve a therapeutic benefit, for monitoring the level of a N-aroylaminothiazole and/or tetrazolylbenzamide compounds in a biological sample, and for other purposes as described herein and apparent to a person skilled in the art, may be performed using techniques and procedures described herein and routinely practiced by a person skilled in the art. Exemplary methods include, but are not limited to, fluorescence cell-based assays (see, e.g., Ma et al., *J. Clin. Invest.* 110:1651-58 (2002)), short circuit apical chloride ion current measurements and patch-clamp analysis (see, e.g., Muanprasat et al., *J. Gen. Physiol.* 124:125-37 (2004); Ma et al., *J. Clin. Invest.* (2002), supra; Sonawane et al., *FASEB J.* 20:130-32 (2006); see also, e.g., Carmeliet, *Verh. K. Acad. Geneeskd. Belg.* 55:5-26 (1993); Hamill et al., *Pflugers Arch.* 391:85-100 (1981)). Immunoassays, including but not limited to immunohistochemistry, immunoblotting techniques, methods for determining gland fluid secretion, and techniques and methods for determining intestinal smooth muscle contraction are described herein and routinely practiced by persons skilled in the art.

Other embodiments and uses will be apparent to one skilled in the art in light of the present disclosures. The following examples are provided merely as illustrative of various embodiments and shall not be construed to limit the claims in any way.

EXAMPLES

The following materials and methods were used in the examples described herein.

Chemicals and Solutions

Amiloride, ATP, UTP and other chemicals, unless otherwise indicated, were purchased from Sigma. 1-(2-methoxyethyl)-2-thiourea was purchased from Oakwood Products (West Columbia, S.C.). $T16A_{inh}$-A01 and $CFTR_{inh}$-172 were synthesized as described (Ma et al. (2002) *J. Clin. Invest.* 110, 1651-1658). The compound collections used for screening included: ~100,000 synthetic small molecules from ChemDiv (San Diego, Calif.) and Asinex, and ~7500 purified natural products from Analyticon (Potsdam, Germany), Timtek (Newark, N.J.), and Biomol (Plymouth Meeting, Pa.). Compounds were maintained as DMSO stock solutions. Structure-activity analysis was done on analogs purchased from ChemDiv and Asinex. The $HCO_3^-$-buffered solution contained (in mM): 120 NaCl, 5 KCl, 1 $MgCl_2$, 1 $CaCl_2$, 10 D-glucose, 5 HEPES, and 25 $NaHCO_3$ (pH 7.4). In the half-CF solution 65 mM NaCl in the $HCO_3^-$-buffered solution was replaced by Na gluconate.

Cell Culture

FRT cells were stably transfected with human TMEM16A (TMEM16A(abc), cDNA provided by Dr. Luis Galietta, Gaslini Institute, Genoa, Italy) and the halide sensor YFP-H148Q/I152L/F46L. Cells were plated in 96-well black-walled microplates (Corning Inc., Corning, N.Y.) at a density of 20,000 cells per well in Coon's modified F12 medium supplemented with 5% fetal calf serum, 2 mM L-glutamine, 100 U/mL penicillin and 100 µg/mL streptomycin. The human submandibular cell line A253 (ATCC HTB 41) was cultured in complete McCoy's 5A medium supplemented with 10% fetal bovine serum, 100 U/mL penicillin and 100 µg/mL streptomycin.

Tracheal and bronchial tissues were obtained from non-CF and CF patients following lung transplantation or from postmortem examinations performed within 24 h after death. Non-CF tissues were from individuals without significant pulmonary airway disease. The Committee on Human Research at the University of California, San Francisco approved the use of human tissues for these studies. Primary cultures of non-CF and CF human bronchial epithelial (HBE; CF HBE) cells were grown at an air-liquid interface as described (Levin et al. (2006) *J. Biol. Chem.* 281, 25803-25812). Cells were plated at a density of $5 \times 10^5$ per $cm^2$ onto 12-mm diameter, 0.4 µm pore polycarbonate cell culture inserts (Snapwell; Corning, Lowell, Mass.) pre-coated with human placental collagen (15 µg/$cm^2$; Sigma). Cultures were grown at an air-liquid interface in ALI medium at 37° C. in 5% $CO_2$/95% air (Fulcher et al. (2005) *Methods Mol. Med.* 107, 183-206). Medium was changed every 2-3 days. Cultures were used 21-30 days after plating at which time transepithelial resistance ($R_{te}$) was 400-1000 Ohm/$cm^2$ and an ASL film was seen.

Primary cultures of non-CF human tracheal gland serous (HTG) cells were generated from the trachea and mainstem bronchi under conditions that induced serous cell differentiation (Finkbeiner et al. (2010) *In Vitro Cell. Dev. Biol. Anim.* 46, 450-456). Briefly, after removal of surface epithelium, the gland-rich submucosal tissues were dissected from between the cartilaginous rings. Small segments of gland tubules and acinar structures were isolated by enzymatic digestion as described. Gland fragments were plated in T-25 flasks in DMEM/F12 supplemented with 20% fetal bovine serum (FBS), penicillin ($10^5$ U/l), streptomycin (100 mg/l), gentamicin (100 mg/l) and amphotericin B (2.5 mg/l). The next day, cultures were rinsed with PBS and plating medium was replaced with Bronchial Epithelial Growth Medium (BEGM; Lonza, Basel, Switzerland). Medium was changed every 24 h for 3 days and every 2 days thereafter. When the outgrowths of cells from attached acini reached ~80% confluence, they were removed by trypsinization (0.05% trypsin, 0.02% EDTA) and plated ($3 \times 10^5$ cells) onto 12 mm cell culture inserts coated with human placental collagen (15 µg/$cm^2$). Serous gland cells were grown at an air-liquid interface on 0.4 µm pore polyester cell culture inserts (Snapwell; Corning, Lowell, Mass.) in DMEM/F12 supplemented with insulin (10 µg/ml), transferrin (5 retinoic acid ($5 \times 10^{-8}$M) hydrocortisone (0.5 µg/ml), triidothyronine (20 ng/ml), bovine serum albumin (2 mg/ml), 0.1% Ultroser G serum substitute (Pall Corporation, Port Washington, N.Y.) and gentamicin (50 mg/l). Cells were studied after 10-14 days, with $R_{te} > 100$ $\Omega \cdot cm^2$.

Short-Circuit Current

Snapwell inserts containing TMEM16A-expressing FRT, HBE, CF HBE or HTG cells were mounted in Ussing chambers (Physiologic Instruments, San Diego, Calif.). Amiloride, $CFTR_{inh}$-172, UTP, ATP, $T16A_{inh}$-A01 and TMEM16A activators were added to the apical solution and an equal volume of vehicle was added at the same time to the basolateral solution. Symmetrical $HCO_3^-$-buffered solutions were used for HBE, CF HBE and HTG cells. For FRT cells, the hemichambers were filled with a half-$Cl^-$ solution (apical) and the $HCO_3^-$-buffered solution (basolateral), and the basolateral membrane was permeabilized with 250 µg/mL amphotericin B, as described (Namkung et al. (2010), supra). Cells were bathed for a 10 min stabilization period and aerated with 95% $O_2$/5% $CO_2$ at 37° C. or room temperature. Apical membrane current (for FRT cells) and short-circuit current were measured using an EVC4000 Multi-Channel V/I Clamp (World Precision Instruments, Sarasota, Fla.) and recorded using PowerLab/8sp (AD Instruments, Castle Hill, Australia).

Patch-Clamp

Whole-cell recordings were made at room temperature on TMEM16A-expressing FRT cells and human submandibular A253 cells. The bath solution contained (in mM): 140 NMDG-Cl, 1 $CaCl_2$, 1 $MgCl_2$, 10 glucose and 10 HEPES (pH 7.4). The pipette solution contained (in mM): 130 CsCl, 0.5 EGTA, 1 $MgCl_2$, 1 Tris-ATP, and 10 HEPES (pH 7.2). Different concentrations of free calcium in pipette solution were obtained by replacing 0.5 mM EGTA with 5 mM EGTA, and using different amounts of $CaCl_2$ in the pipette solution. Pipettes were pulled from borosilicate glass and had resistances of 3-5 MΩ after fire polishing. Seal resistances were between 3 and 10 GΩ. After establishing the whole-cell configuration, TMEM16A was activated by 100 µM ATP, TMEM16A activators or different concentrations of free calcium in the pipette solution. Whole-cell currents were elicited by applying hyperpolarizing and depolarizing voltage pulses from a holding potential of 0 mV to potentials between −100 mV and +100 mV in steps of 20 mV. Recordings were made at room temperature using an Axo-patch-200B (Axon Instruments). Currents were digitized with a Digidata 1440A converter (Axon Instruments), filtered at 5 kHz, and sampled at 1 kHz.

Cytoplasmic Calcium Measurements

FRT cells in 96-well black-walled microplates were loaded with Fluo-4 NW per the manufacturer's protocol (Invitrogen, Carlsbad, Calif.). Fluo-4 fluorescence was measured with a FLUOstar Optima fluorescence plate reader equipped with syringe pumps and custom Fluo-4 excitation/emission filters (485/538 nm).

Immunoblot

CF HBE and HTG cells were lysed with cell lysis buffer (50 mM pH 7.4, 1% NP-40, 0.25% sodium deoxycholate, 150 mM NaCl, 1 mM EDTA, 1 mM $Na_3VO_4$, and protease inhibitor mixture (Roche Applied Science, Indianapolis, Ind.)). Cell debris was removed by centrifugation, and proteins in the supernatant were resolved by SDS-polyacrylamide gel electrophoresis and immunoblotted using standard procedures (transfer to polyvinylidene difluoride membrane, 1 h blocking in 5% nonfat dry milk, primary TMEM16A antibody (1:1000 dilution, ab16293, Abcam Inc., Cambridge, Mass.) and secondary antibody incubations, and enhanced chemiluminescence detection).

Immunohistochemistry

Paraffin tissue sections (5 μm) were dewaxed in two changes of Clear-Rite (Thermo Scientific, Waltham, Mass.) then rehydrated through a series of graded alcohols. Slides were submerged in 3% hydrogen peroxide for 10 min to quench endogenous peroxidase activity. Heat-induced antigen retrieval was performed by boiling slides in Borg antigen retrieval buffer (Biocare Medical, Concord, Calif.) for 10 min at 125° C. Slides were blocked with protein block (DAKO, Carpinteria, Calif.) for 10 min and incubated for 60 min with TMEM16A primary antibody (NBP1-49559, Novus Biologicals, Littleton, Colo.). Antibody detection was done using the SuperPicture Polymer Kit (Invitrogen, Carlsbad, Calif.). 3,3'-diaminobenzidine) was used to develop the stains. Slides were counterstained with hematoxylin and photographed.

Gland Fluid Secretion

Human airways were obtained from human subjects following lung transplantation and the California Lung Transplantation Donation Network. For optical recording of mucus (fluid) secretion in airway glands, a fragment of human tracheas or bronchus of approximately 1 $cm^2$ with underlying glands was dissected from the cartilage and mounted in a 37° C. chamber allowing serosal solution exchange. The mucosal surface was rinsed and blotted dry with a cotton swab and further dried with an air stream, after which ~100 μl of water-saturated mineral oil was placed on the surface. Agonists and inhibitors were added to the serosal side by complete bath replacement. Mucus bubbles in the oil layer were imaged using a Nikon SMZ stereozoom epifluorescence microscope (Nikon, Tokyo, Japan) equipped with P-HR Plan Apo 1.6× objective lens (working distance 24 mm) and Hamamatsu ORCA-ER CCD camera. Mucus bubble volume was deduced from bubble size as described (Thiagarajah et al. (2004) *Faseb J.* 18, 875-877).

Intestinal Smooth Muscle Contraction

Wild type CD1 mice (age 8-10 weeks) were killed by avertin overdose (200 mg/kg). The ileum removed and washed with ice-cold $HCO_3^-$-buffered solution. The ends of the ileal segments were tied with silk thread and connected to a force transducer. Beal segments were equilibrated for 60 min with a resting force of ~1 mN, with changes of the bathing solution every 15 min. Tension was monitored continuously with a fixed-range precision force transducer (TSD, 125 C; Biopac, Goleta, Calif.) connected to a differential amplifier (DA 100B; Biopac). Data were recorded using MP100, Biopac digital acquisition system and analyzed using Acknowledge 3.5.7 software.

Preparation of Compounds

Compounds were prepared according to the following procedures (see Examples 1-7). Flash chromatography was performed on a CombiFlash Companion chromatography system (Teledyne Isco, Nebr.). $^1$H and $^{13}$C NMR were obtained on a Bruker 300 MHz instrument. High-resolution mass spectrometry was done at a core facility at the University of California, Riverside, Calif. Elemental analyses were done at the Micro-Mass Facility, University of California, Berkeley, Calif.

Example 1

N-(2-Methoxyethyl)-4-phenyl-2-thiazolamine (1)

A solution of 2-bromoacetylphenone (1.59 g, 7.99 mmol) and 1-(2-methoxyethyl)-2-thiourea (1.02 g, 7.61 mmol) in ethanol (30 mL) was refluxed under argon for 4 h. After the reaction mixture was cooled to room temperature, saturated aqueous $NaHCO_3$ was slowly added. Ethanol was removed under reduced pressure. The resulting suspension was extracted twice with $CH_2Cl_2$. The combined organic phase was washed with water, dried ($Na_2SO_4$) and concentrated. Chromatography [silica, hexanes:ethyl acetate (9:1 to 4:1)] yielded a white crystalline solid (1.62 g, 91%). Mp 57-60° C. $^1$H NMR (300 MHz, $CDCl_3$) δ 3.39 (s, 3H), 3.53 (m, 2H), 3.64 (m, 2H), 5.46 (br, 1H), 6.70 (s, 1H), 7.27 (m, 1H), 7.37 (m, 2H), 7.80 (m, 2H). $^{13}$C NMR (75 mHz, $CDCl_3$) δ 45.2, 58.8, 70.7, 101.0, 126.0, 127.6, 128.5. ESI-MS calculated for $C_{12}H_{15}N_2OS$ 235.0900. found 235.0902. (See also FIG. 3C.)

Example 2

N-(2-Methoxyethyl)-N-(4-phenyl-2-thiazolyl)-2,3,4-trimethoxybenzeneacetamide

A solution of 1 (1.00 g, 4.27 mmol) and anhydrous pyridine (690 mL, 8.54 mmol) in anhydrous toluene (40 mL) was stirred for 5 min. To the reaction mixture was added a solution of 3,4,5-trimethoxybenzoyl chloride (1.47 g, 6.41 mmol) in anhydrous toluene (20 mL). The mixture was refluxed under argon for 4.5 h, cooled to room temperature, and poured into water and ethyl acetate. The organic phase was collected, dried ($Na_2SO_4$) and concentrated. Chromatography [silica, hexanes:ethyl acetate (4:1 to 3:1)] yielded a crystalline solid (1.33 g, 73%). Mp 97-100° C. $^1$H NMR (300 MHz, $CDCl_3$) δ 3.28 (s, 3H), 3.86 (t, J=5.4, 2H), 3.88 (s, 6H), 3.90 (s, 6H), 4.48 (t, J=5.4, 211), 6.92 (s, 2H), 7.26 (s, 1H), 7.33 (m, 1H), 7.43 (m, 2H), 7.90 (m, 2H). $^{13}$C NMR (75 mHz, $CDCl_3$) δ 49.6, 56.2, 58.9, 61.0, 69.7, 105.4, 109.4, 126.0, 127.9, 128.7. ESI-MS Calculated for $C_{22}H_{25}N_2O_5S$ 429.1479. found 429.1477. (See also FIG. 3C.)

Other compounds of structure (I) were prepared in an analogous manner to that described in Examples 1 and 2.

Example 3

N-(4-bromophenyl)-3-(1H-tetrazol-1-yl)benzamide

Thionyl chloride (477 mL, 6.58 mmol) and 3-(1H-tetrazol-1-yl)benzoic acid. (50 mg, 0.263 mmol) was heated to 80° C. in a screw-cap vial. After a clear solution was observed, the residue solid on the wall was washed by gentle shaking. After 1.5 h, the reaction was cooled to room temperature. The reaction mixture was concentrated to dryness under reduced pressure. The resulting white solid was suspended in $CH_2Cl_2$ (1.5 mL) and treated with p-bromoaniline (90 mg, 0.526 mmol) and triethylamine (100 mL, 0.719 mmol). The reaction was stirred at room temperature for 14 h, mixed with silica gel and concentrated to dryness. Chromatography [silica, $CH_2Cl_2$:methanol (98:2 to 1:3)] yielded an off-white solid (48 mg, 53%). Decomp point 203° C. $^1$H NMR (300 MHz, DMSO-$d_6$) d 7.58 (d, J=4.9, 2H), 7.79 (d, J=4.9, 2H), 7.85 (8, J=8.0, 1H), 8.10-8.18 (m, 2H), 8.47-8.51 (m, 1H), 10.22 (s, 1H), 10.62 (br, 1H, NH). $^{13}$C NMR (75 mHz, DMSO-$d_6$) δ 120.18, 122.08, 123.92, 128.50, 130.11, 131.30, 142.25. ESI-MS Calculated for $C_{14}H_{10}BrN_5O$ 344.0141. found 344.0152.

Other compounds of structure (II) were prepared in an analogous manner to that described in Example 3.

Example 4

4-phenyl-2-thiazolamine (2)

Thiourea (935 mg, 12.3 mmol) and 2-bromoacetylphenone (2.56 g 11.2 mmol) were suspended in water (50 mL).

The mixture was stirred vigorously at room temperature for 16 hours. The resulting suspension was poured into saturated NaHCO$_3$ solution and filtered. The solid residue was washed thoroughly with water and dried to yield a white solid (1.89 g, 96%). $^1$H NMR (300 MHz, CDCl$_3$) δ 3.39 (s, 3H), 3.53 (m, 2H), 3.64 (m, 2H), 5.46 (br, 1H), 6.70 (s, 1H), 7.27 (m, 1H), 7.37 (m, 2H), 7.80 (m, 2H). $^{13}$C NMR (75 mHz, CDCl$_3$) δ 45.2, 58.8, 70.7, 101.0, 126.0, 127.6, 128.5.

Example 5

N-(2,3,4-Trimethoxybenzoyl)-4-phenyl-2-thiazolamine (3)

A solution of 2 (500 mg, 2.84 mmol) and 3,4,5-trimethoxybenzoyl chloride (788 mg, 3.41 mmol) in CH$_2$Cl$_2$ (20 mL) was treated with DMAP (485 mg, 3.98 mmol) at room temperature for 1 hour. The mixture was washed with water and Brine. The organic phase was dried (Na$_2$SO$_4$) and concentrated. Chromatography [silica, hexanes:methylene chloride:ethyl acetate (6:3:1)] yielded a white solid (726 mg, 70%). $^1$H NMR (300 MHz, CDCl$_3$) δ 3.39 (s, 3H), 3.53 (m, 2H), 3.64 (m, 2H), 5.46 (br, 1H), 6.70 (s, 1H), 7.27 (m, 1H), 7.37 (m, 2H), 7.80 (m, 2H). $^{13}$C NMR (75 mHz, CDCl$_3$) δ 45.2, 58.8, 70.7, 101.0, 126.0, 127.6, 128.5.

Example 6

N-(4-pyridylmethyl)-N-(4-phenyl-2-thiazolyl)-2,3,4-trimethoxybenzeneacetamide

A solution of 3 (100 mg, 0.270 mmol) and triphenylphosphinee (141 mL, 0.540 mmol) in anhydrous THF (3 mL) was treated with tetrahydropyran-2-methanol (45.6 μL, 0.405 mmol). The mixture was cooled to 0° C. and DIAD (106 μL, 0.540 mmol) was added. The reaction mixture was stirred at 0° C. for 1 h and then room temperature overnight. The reaction mixture was concentrated and Chromatography [silica, hexanes:ethyl acetate (3:1)] yielded a white solid (93 mg, 73%). $^1$H NMR (300 MHz, CDCl$_3$) δ3.28 (s, 3H), 3.86 (t, J=5.4, 2H), 3.88 (s, 6H), 3.90 (s, 6H), 4.48 (t, J=5.4, 2H), 6.92 (s, 2H), 7.26 (s, 1H), 7.33 (m, 1H), 7.43 (m, 2H), 7.90 (m, 2H). $^{13}$C NMR (75 mHz, CDCl$_3$) δ 49.6, 56.2, 58.9, 61.0, 69.7, 105.4, 109.4, 126.0, 127.9, 128.7. ESI-MS Calculated for C$_{25}$H$_{28}$N$_2$O$_5$S 469.1792. found 469.1796.

Other compounds of structure (I) were prepared according to the general procedures described in Examples 4-6.

Example 7

N-(4-isopropylphenyl)-3-(1H-tetrazol-1-yl)benzamide

Thionyl chloride (344 μL, 4.74 mmol) and 3-(1H-tetrazol-1-yl)benzoic acid (30 mg, 0.158 mmol) was heated to 80° C. in a screw-cap vial. After a clear solution was observed, the residue solid on the wall was washed by gentle shaking. After 1.5 h, the reaction was cooled to room temperature. The reaction mixture was concentrated to dryness under reduced pressure. The resulting white solid was suspended in CH$_2$Cl$_2$ (0.5 mL) and treated with p-bromoaniline (87 μL, 0.632 mmol) and triethylamine (110 μL, 0.789 mmol). The reaction was stirred at room temperature for 14 h, mixed with silica gel and concentrated to dryness. Chromatography [silica, CH$_2$Cl$_2$:methanol (98:2 to 1:3)] yielded an light-brown solid (28 mg, 58%). $^1$H NMR (300 MHz, DMSO-d$_6$) δ 7.58 (d, J=4.9, 2H), 7.79 (d, J=4.9, 2H), 7.85 (d, J=8.0, 1H), 8.10-8.18 (m, 2H), 8.47-8.51 (m, 1H), 10.22 (s, 1H), 10.62 (br, 1H, NH). $^{13}$C NMR (75 mHz, DMSO-d$_6$) δ 120.18, 122.08, 123.92, 128.50, 130.11, 131.30, 142.25. ESI-MS Calculated for C$_{17}$H$_{17}$N$_5$O 308.1515. found 344.0152.

Other compounds of structure (II) were prepared according to the general procedures described in Example 7.

Example 8

Screening of Synthetic Libraries

TMEM16A activators were identified from screening of ~110,000 synthetic drug-like compounds, purified natural products and approved/investigational drugs. The cell-based screen employs FRT cells coexpressing human TMEM16A and the I$^-$-sensing yellow fluorescent protein YFP-H148Q/1152L/F46L. FRT cells were chosen because of their low basal I$^-$ and Cl$^-$ transport, rapid growth on uncoated plastic, strong stable expression of transfected proteins, and formation of tight junctions for measurements of transepithelial short-circuit current (Ma et al., supra).

High-throughput screening was done using an automated screening platform (Beckman) equipped with FluoStar fluorescence plate readers (BMG Lab Technologies, Durham, N.C.) as described (Ma et al., supra). Each well of a 96-well plate was washed 3 times with PBS (200 μL/wash), leaving 50 μL PBS. Test compounds (0.5 μL) were added to each well at 25 μL final concentration. After 10 min, 96-well plates were transferred to a plate reader for fluorescence assay. Each well was assayed individually for TMEM16A-mediated I$^-$ influx by recording fluorescence continuously (400 ms per point) for 2 s (baseline), then 50 μL of a 140 mM I$^-$ solution was added. The initial rate of I$^-$ influx was computed from fluorescence data by non-linear regression.

As diagrammed in FIG. 1A, test compounds at 25 μM final concentration were added 10 min prior to I$^-$ addition. The 10 min incubation was chosen to allow for compound transport into cytoplasm and to minimize false positives from compounds that elevate cytoplasmic Ca$^{2+}$ transiently. Fluorescence from individual wells of 96-well plates was measured just prior to and for 6 s after I$^-$ addition for computation of initial I$^-$ influx rate. FIG. 1B shows representative fluorescence data from single wells showing positive (ionomycin) and negative (vehicle only) controls, and examples of inactive and active compounds.

Example 9

Characterization of TMEM16A Activators

Primary screening yielded 40 compounds that increased I$^-$ influx by >2 mM/s at 25 μM (>50% of maximal I$^-$ influx produced by 100 μM ATP) and had EC$_{50}$ of less than 10 μM. FIG. 1C shows structures of active compounds from six chemical classes. Secondary screens were done to identify compounds that increased I$^-$ influx by targeting TMEM16A. Measurements on TMEM16A null cells (expressing YFP alone) showed that none of the active compounds increased influx. However, C$_{act}$ and D$_{act}$ increased TMEM16A-mediated efflux by producing sustained elevation of cytoplasmic Ca$^{2+}$ (FIG. 2A). Of the remaining compounds that did not elevate Ca$^{2+}$, the N-aroylaminothiazole E$_{act}$ and the tetrazolylbenzamide F$_{act}$ (see FIG. 1C) were chosen for further characterization because they produced maximal TMEM16A activation (compared to ATP effect) in apical membrane current measurements, whereas $A_{act}$ and $B_{act}$ produced only ~50% maximal activation.

FIG. 2B (left and center) shows measurements of apical membrane current in TMEM16A-expressing FRT cells in which the cell basolateral membrane was permeabilized with Amphotericin B and a mucosal-to-serosal Cl⁻ gradient was applied. The purinergic agonist ATP, which transiently elevates cytoplasmic $Ca^{2+}$, produced a large but transient elevation in Cl⁻ current. $E_{act}$ and $F_{act}$ produced large, concentration-dependent increases in Cl⁻ current, which were inhibited by the TMEM16A-selective inhibitor $T16A_{inh}$-A01. The current increase was sustained for >10 min (FIG. 2B, inset). The concentration-activation data gave $EC_{50}$ of ~3 µM for $E_{act}$ and ~6 µM for $F_{act}$ (FIG. 2B, right). FIG. 2C shows synergy between $E_{act}$ and $F_{act}$ for TMEM16A activation, suggesting distinct mechanisms of action. Whereas 1-3 µM $F_{act}$ produced little TMEM16A activation alone, it greatly increased TMEM16A current following 1 µM $E_{act}$. Data are also shown for a second Fact compound ($F_{act}9$, see Table 1) in FIG. 9.

FIG. 2D (left) shows that $E_{act}$ was effective in producing Cl⁻ current in mouse TMEM16A, which supports its testing in mouse tissues. FIG. 2D (right) shows activation by $E_{act}$ of TMEM16B, the other TMEM16 isoform having CaCC activity. Neither $E_{act}$ nor $F_{act}$ affected CFTR conductance or ENaC Na⁺ conductance (FIG. 2E), which are often found in epithelial cell mucosal membranes where TMEM16A is expressed.

Example 10

Structure-Activity Analysis of TMEM16A Activators

More than 1000 analogs of the B, E and F classes were tested for TMEM16A inhibition activity, reasoning that small structural changes can convert an agonist into an antagonist. FIG. 3A illustrates the structures of exemplary compounds of the B and E classes fully inhibited TMEM16A Cl⁻ conductance. In each case relatively minor chemical structural changes (see FIG. 3A) converted an activator to an inhibitor, supporting the conclusion that these compounds target TMEM16A directly.

The common scaffold for $E_{act}$ and for T16Ainh-A01 is as follows.

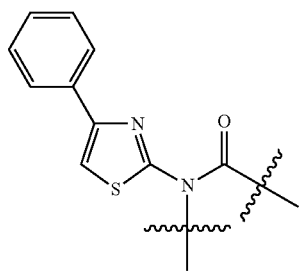 [SMILES: *C(=O)N(*)c1nc(-c2ccccc2)cs1]

The common scaffold for $B_{act}$ and for $B_{inh}$ (B class inhibitor) is as follows.

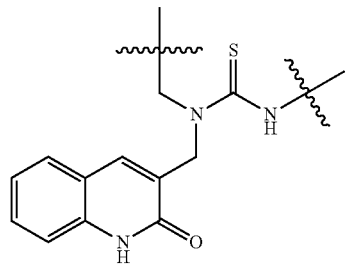 [SMILES: *CN(Cc1cc2ccccc2[nH]c1=O)C(=S)N*]

Example 11

Synthesis of TMEM16A Activators $E_{act}$ and $F_{act}$ analogs were assayed to establish structure-activity relationships and to select the best compounds for synthesis in highly pure form for biological studies. Of 673 commercially available class E analogs screened, 18 compounds increased TMEM16A Cl⁻ conductance. Nine out of the ten most potent compounds had a 2,3,4-trimethoxyphenyl (TMOP) group at the $R^a$ position (Table 1). Similar compounds but with 4-methoxyphenyl or 2,5-dimethoxyphenyl at $R^a$ were inactive, as summarized in FIG. 3B (left). Of the active compound with TMOP at $R^a$, the most potent compounds had benzyl, (tetrahydrofuran-2-yl)methyl, or methoxyethyl groups at $R^b$. Compounds containing an additional carbon on the benzyl group were inactive, as were compounds with methylene replacing the oxygen in methoxyethyl group. Methoxyethyl at $R^b$ and phenyl group at $R^e$ gave one of the most potent analogs. Limited SAR on the F class was done on 9 synthesized analogs, as analogs were not available from commercial sources. While 4-bromo at $R^a$ increased TMEM16A conductance, the 2-bromo or 3-bromo analogs did not, and compounds containing 4-chloro, 4-nitro, 4-ethoxycarbonyl or 4-dimethylamino had low activity.

Figure 3C:
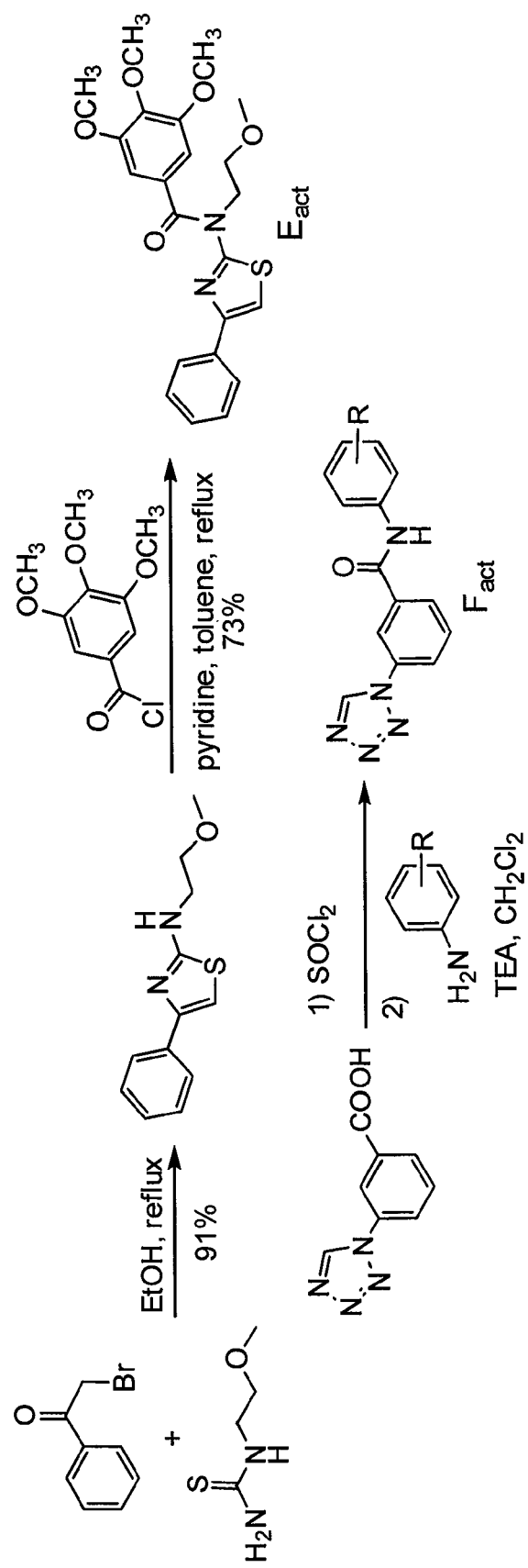

The most potent compounds of the E and F classes were synthesized in highly pure form for further characterization and biological studies (see general synthesis scheme in FIG. 3C and Examples herein). $E_{act}$ was synthesized in two steps. 2-Aminothiazole was obtained by reflux of 2-bromoacetylphenone and 1-(2-methoxyethyl)-2-thiourea in ethanol (FIG. 3C). $E_{act}$ was obtained by reaction of 2-aminothiazole and 2,3,4-trimethoxybenzoyl chloride using anhydrous pyridine in anhydrous toluene. The yield (73%) was comparable to that reported for similar reactions between N-alkyl-2-aminothiazoles and benzoyl chloride (Satoh et al. (2009) *Bioorg. Med. Chem. Lett.* 19, 5464-5468). $F_{act}$ analogs were synthesized from 3-(1H-tetrazol-1-yl)benzoic acid and the corresponding anilines. Because amide formation with 1,1'-carbonyldiimidazole as the coupling agent did not drive the reaction to completion, a two-step, one-pot procedure was adopted (DiMauro et al. (2006) *J. Med. Chem.* 49, 5671-5686). The benzoic acid was first treated with neat $SOCl_2$ at 80° C. for 1.5 h. After removal of excess $SOCl_2$ by rotary evaporation, the resulting acid chloride was suspended in $CH_2Cl_2$ and treated with anilines and TEA to yield $F_{act}$ compounds in 48-65% yield.

TABLE 1

Structure-activity analysis of $E_{act}$ and $F_{act}$ analogs. $EC_{50}$ values determined from fluorescence plate reader assay.

$E_{act}$ $R^a$ = 3,4,5-trimethoxyphenyl

| $R^b$ | $R^c$ | $EC_{50}$ (µM) |
|---|---|---|
| benzyl | 4-methoxyphenyl | 4 |
|  | phenyl | 1 |
|  | 4-chlorophenyl | 4 |
|  | 2,5-dimethoxyphenyl | 5 |
| (tetrahydrofuran-2-yl)methyl | phenyl | 4 |
|  | 4-fluorophenyl | 3 |
|  | 4-chlorophenyl | 3 |
|  | 4-methoxyphenyl | 8 |
| (furan-2-yl)methyl | phenyl | 9 |
|  | 4-fluorophenyl | 9 |
| 2-methoxyethyl | phenyl | 3 |
|  | 2,5-dimethoxyphenyl | Inactive |
|  | 4-methoxyphenyl | 5 |
|  | pyrid-4-yl | inactive |
| (tetrahydropyran-2-yl)methyl | phenyl | 3 |
| (pyrid-4-yl)methyl | phenyl | 2 |
| (pyrid-2-yl)methyl | phenyl | 9 |

$F_{act}$

| R | $EC_{50}$ (µM) |
|---|---|
| 4-bromophenyl | 37 |
| 3-bromophenyl | inactive |
| 2-bromophenyl | inactive |
| 4-bromo-3-trifluoromethylphenyl | 55 |
| 4-chlorophenyl | inactive |
| 4-nitrophenyl | inactive |
| 4-ethoxycarbonylphenyl | inactive |
| 4-(N,N-dimethylamino)phenyl | inactive |
| 4-(2-propyl)phenyl ($F_{act}$9) | 11 |

Example 12

Figure 4A:
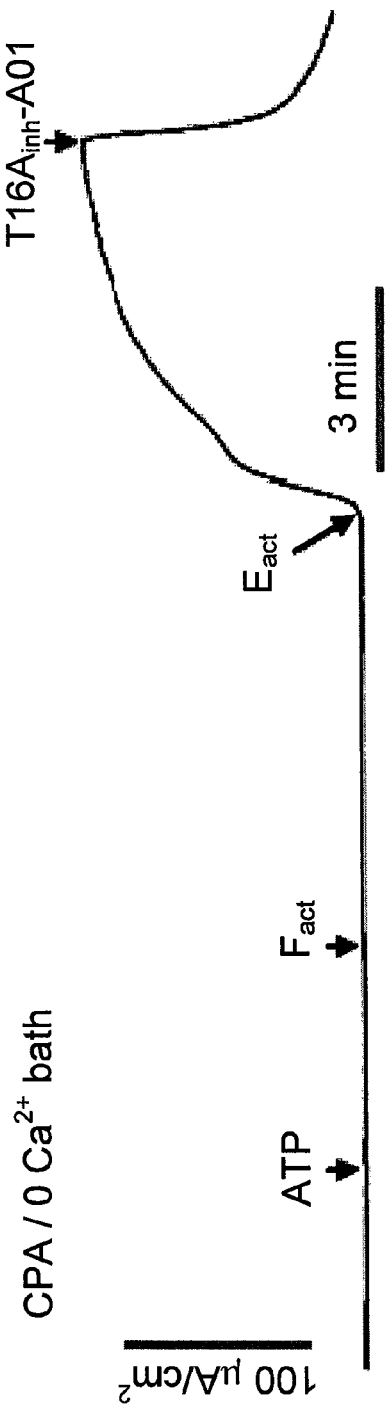
Figure 4B:
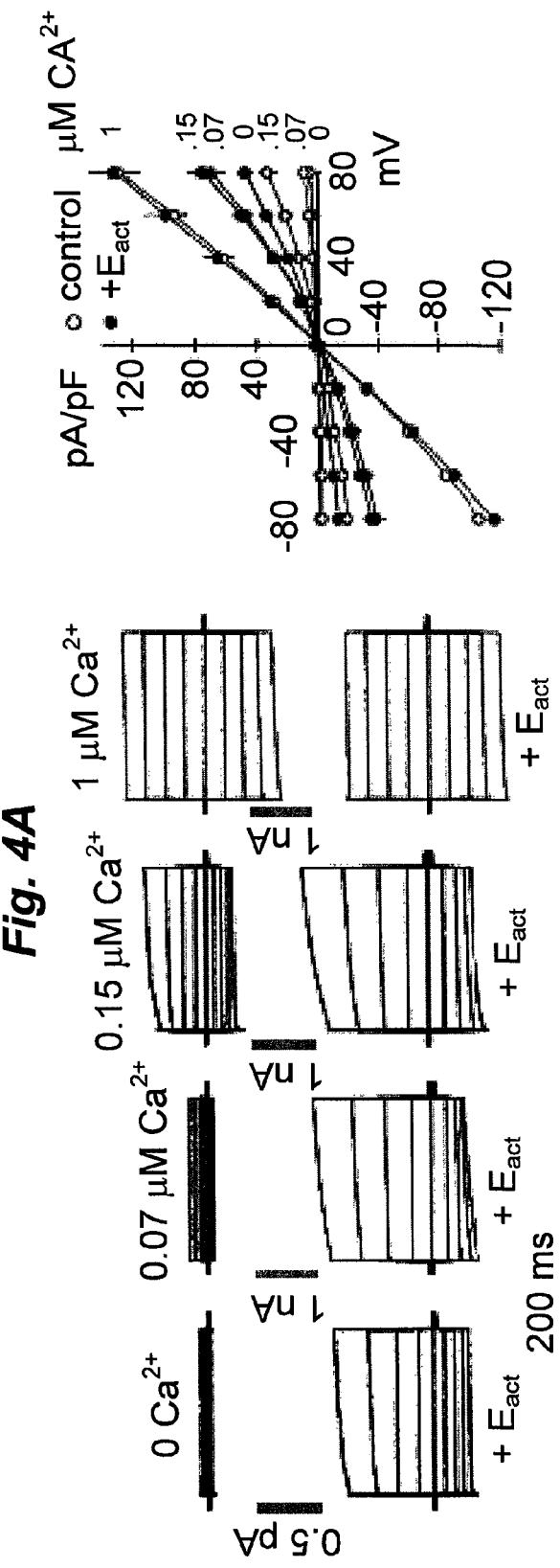

Patch-Clamp Analysis of $Ca^{2+}$ Requirements for TMEM16A Activation by Exemplary Activators The $Ca^{2+}$ dependence of TMEM16A activation by $E_{act}$ and $F_{act}$ was investigated. Apical membrane current measurements done with zero $Ca^{2+}$ apical and basolateral solutions in the presence of cyclopiazonic acid (to deplete intracellular $Ca^{2+}$ stores) showed TMEM16A Cl⁻ currents induced by $E_{act}$, but not by ATP or $F_{act}$ (FIG. 4A). Whole-cell currents were then recorded by patch-clamp at different cytoplasmic (pipette) [$Ca^{2+}$]. In the absence of activators, FIG. 4B (top) shows increasing TMEM16A Cl⁻ current with outward rectification at relatively low [$Ca^{2+}$] and near linear currents at high [$Ca^{2+}$], in agreement with prior patch-clamp studies of TMEM16A (Yang et al., supra). $E_{act}$ strongly activated TMEM16A at 0 $Ca^{2+}$, producing outwardly rectifying currents, with more linear currents at higher [$Ca^{2+}$] (FIG. 4B, bottom and right). In contrast, $F_{act}$ did not product Cl⁻ current at 0 $Ca^{2+}$, but increased Cl⁻ current (compared to no compound) at submaximal $Ca^{2+}$ (FIG. 4C). Maximum TMEM16A Cl⁻ current at high [$Ca^{2+}$] was not further increased by $E_{act}$ or $F_{act}$. Thus, $E_{act}$ and $F_{act}$ activate TMEM16A by different mechanisms: $E_{act}$ as a largely $Ca^{2+}$-independent 'activator', and $F_{act}$ as a 'potentiator' of $Ca^{2+}$ activation. T16A$_{inh}$-A01 completely blocked Cl⁻ currents produced by $E_{act}$ or $F_{act}$ (FIG. 4D).

Example 13

Epithelial Fluid Secretion and Intestinal Smooth Muscle Contraction

Prior studies using TMEM16A inhibitors and RNAi knockdown indicated that TMEM16A is a minor component of total CaCC conductance in human bronchial surface epithelial cell cultures under basal conditions, but that TMEM16A is strongly upregulated after IL-4 treatment for 24 h (Namkung et al., 2011, supra). Supporting this conclusion, the results described herein indicated that $E_{act}$ did not induce Cl⁻ current in untreated human Cl⁻ bronchial epithelial cells, whereas UTP, which elevates cytoplasmic $Ca^{2+}$ and hence non-TMEM16A CaCC(s), produced a large Cl⁻ current (FIG. 5A, left). Surprisingly, $E_{act}$ induced Cl⁻ current in IL-4 treated CF bronchial cells, which was blocked by the TMEM16A-selective inhibitor T16A$_{inh}$-A01 (FIG. 5A, center and right).

Prior reports suggested the involvement of TMEM16A in CaCC activity in airway submucosal glands (Fischer et al. (2010) *Am. J. Physiol. Lung Cell. Mol. Physiol.* 299, L585-594; Lee et al. (2010) *Am. J. Physiol. Lung Cell. Mol. Physiol.* 298, L210-231 Epub 2009 Dec. 4). To verify TMEM16A function, short-circuit current measurements were performed in primary cultures of human tracheal submucosal gland epithelial cells that were grown under conditions that preserve serous-type phenotype (Finkbeiner et al., supra). FIG. 5B (left) shows increased Cl⁻ current in response to UTP and $E_{act}$, which was largely abolished by T16A$_{inh}$-A01 pretreatment. FIG. 5B (middle) shows increased Cl⁻ conductance with $E_{act}$ in the absence of UTP pretreatment. Immunoblot (figure inset) confirmed TMEM16A protein in the glandular epithelial cell cultures. Averaged peak Cl⁻ currents are summarized in FIG. 5B (right).

Example 14

Airway Submucosal Gland Fluid Secretion in Human Bronchi

Figure 6A:
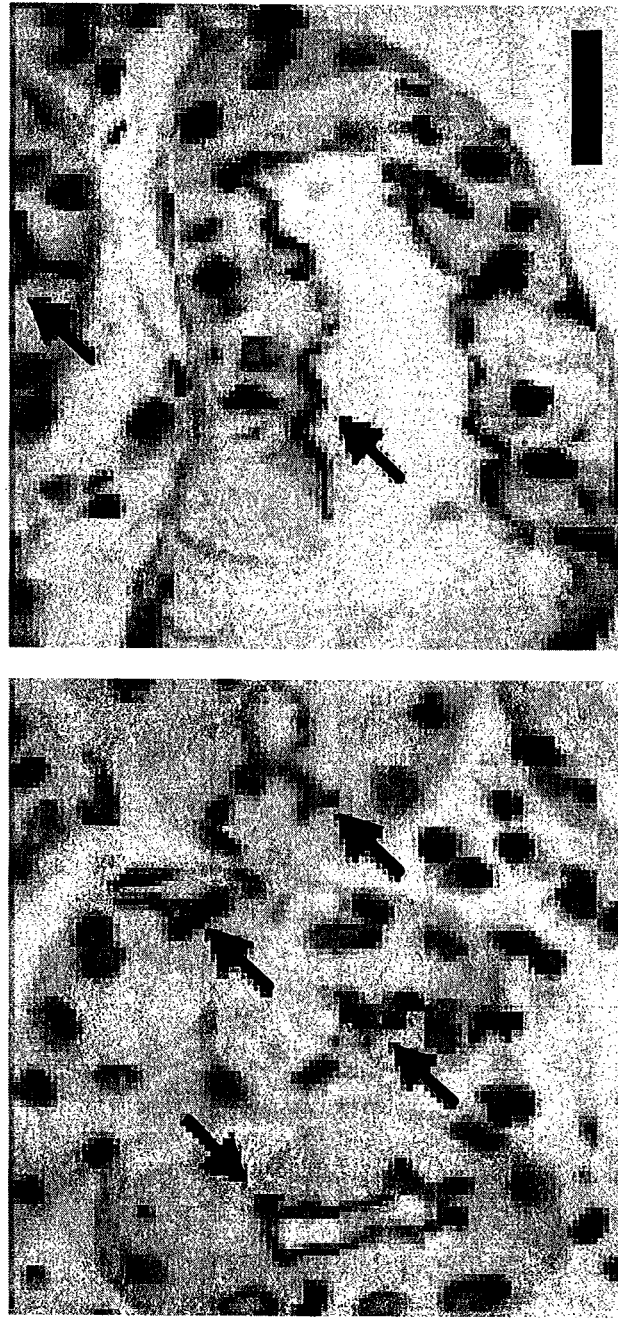
FIG. 6A-C. Airway submucosal gland fluid secretion in human bronchi.
Figure 6B:
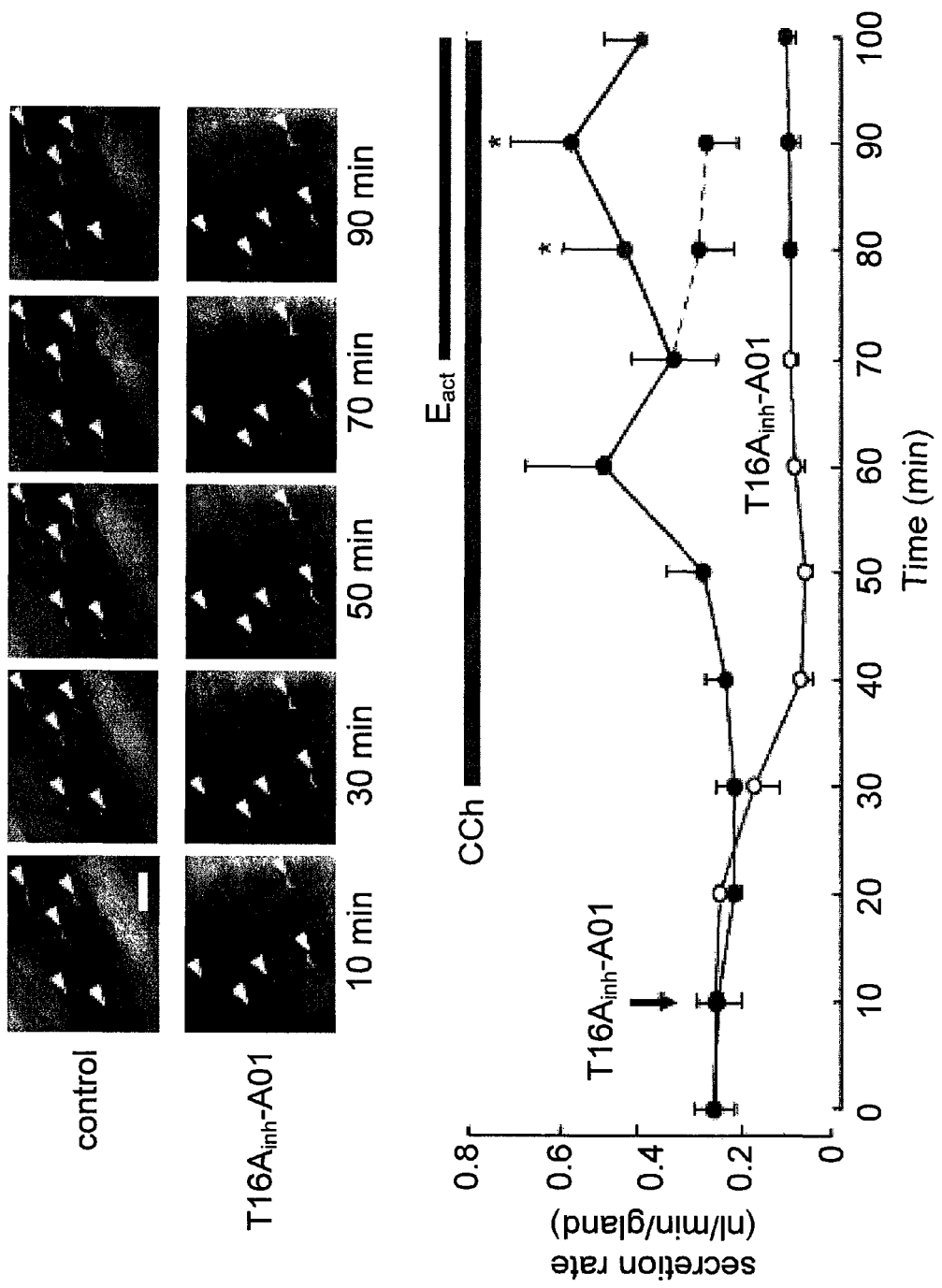
Figure 6C:
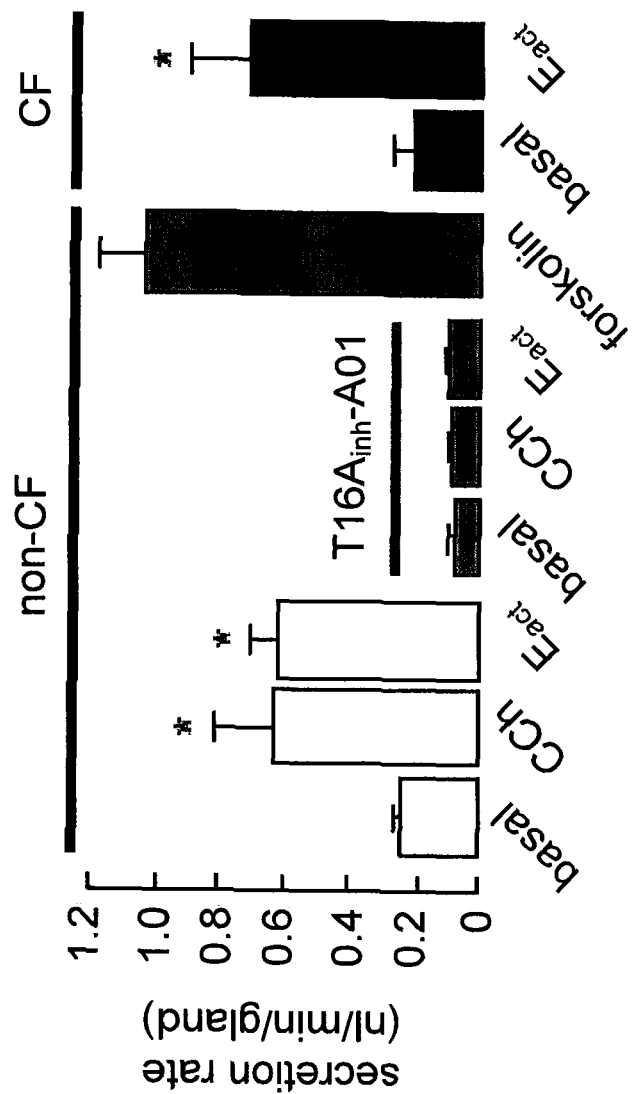

Immunostaining of human non-CF and CF bronchi showed TMEM16A expression at the luminal membrane of submucosal gland serous cells, but not gland mucous cells or surface epithelial cells (FIG. 6A). Similar staining was found in non-CF and CF human bronchi. Fluid secretion was measured in individual submucosal glands from the increasing size of mucus (fluid) bubbles in which airway fragments were mounted in a 37° C. perfusion chamber and the mucosal solution was covered with oil. FIG. 6B (top) shows mucus bubbles following addition of carbachol and $E_{act}$ in human bronchi. FIG. 6B (bottom) summarizes the secretion rate from many mucus droplets, showing non-zero basal secretion, and significantly increased secretion following serosal application of submaximal carbachol and $E_{act}$. T16A$_{inh}$-A01 pre-treatment abolished basal and agonist-stimulated gland fluid secretion. The data summary in FIG. 6C shows $E_{act}$-induced gland fluid secretion in non-CF and CF bronchi of comparable magnitude to that induced by maximal cAMP stimulation by forskolin.

Example 15

Figure 7A:
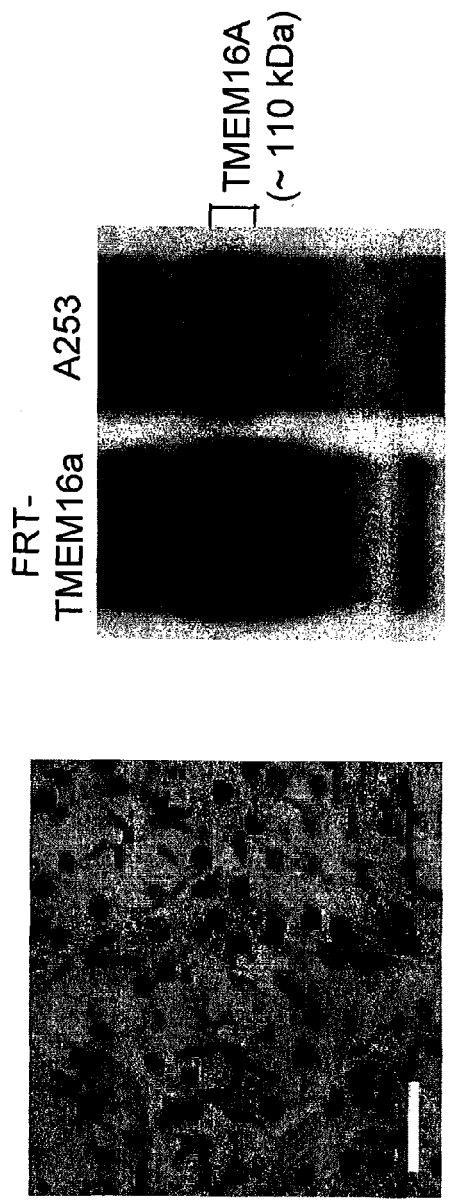
FIG. 7A-B. Salivary gland epithelial cell Cl⁻ secretion.
Figure 7B:
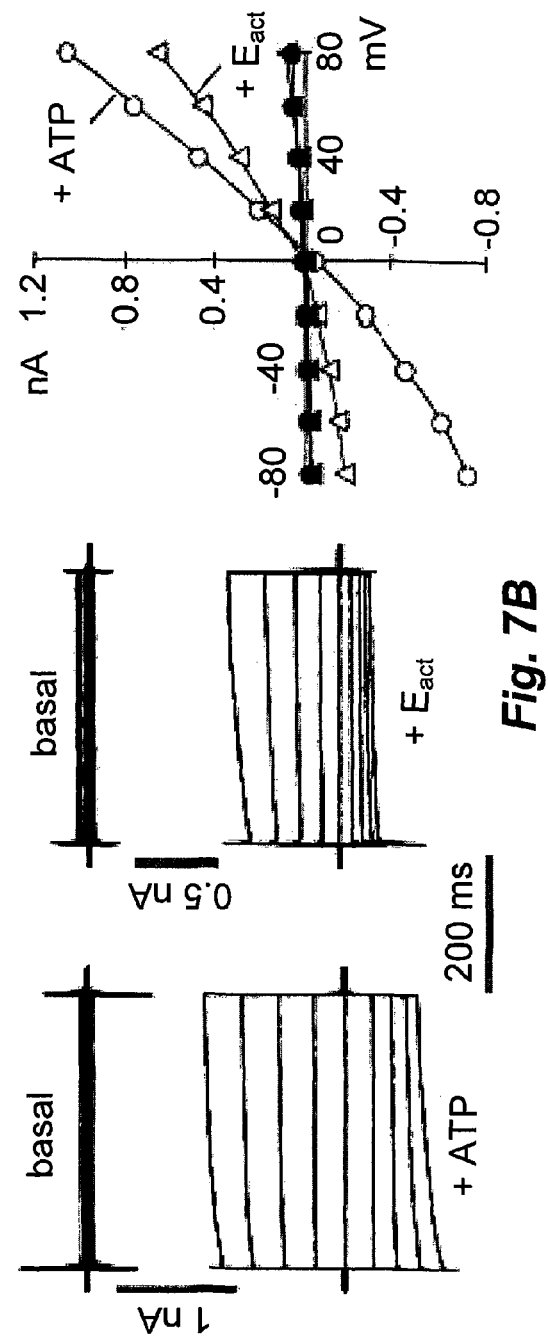

Effect of CaCC Activators on Salivary Gland Epithelial Cell Chloride Secretion and Intestinal Smooth Muscle Contraction Prior studies implicated TMEM16A as the principle CaCC in salivary gland epithelium (Yang et al., supra; Romanenko et al., supra; Namkung et al., 2011, supra). TMEM16A immunostaining showed that TMEM16A is expressed on the apical surface of acinar epithelial cells in human parotid gland (FIG. 7A, left). A253 cells, a human salivary gland epithelial cell line, express TMEM16A (FIG. 7A, right). By whole-cell patch-clamp $E_{act}$ strongly increased Cl⁻ current in A253 cells (FIG. 7B).

Figure 8A:
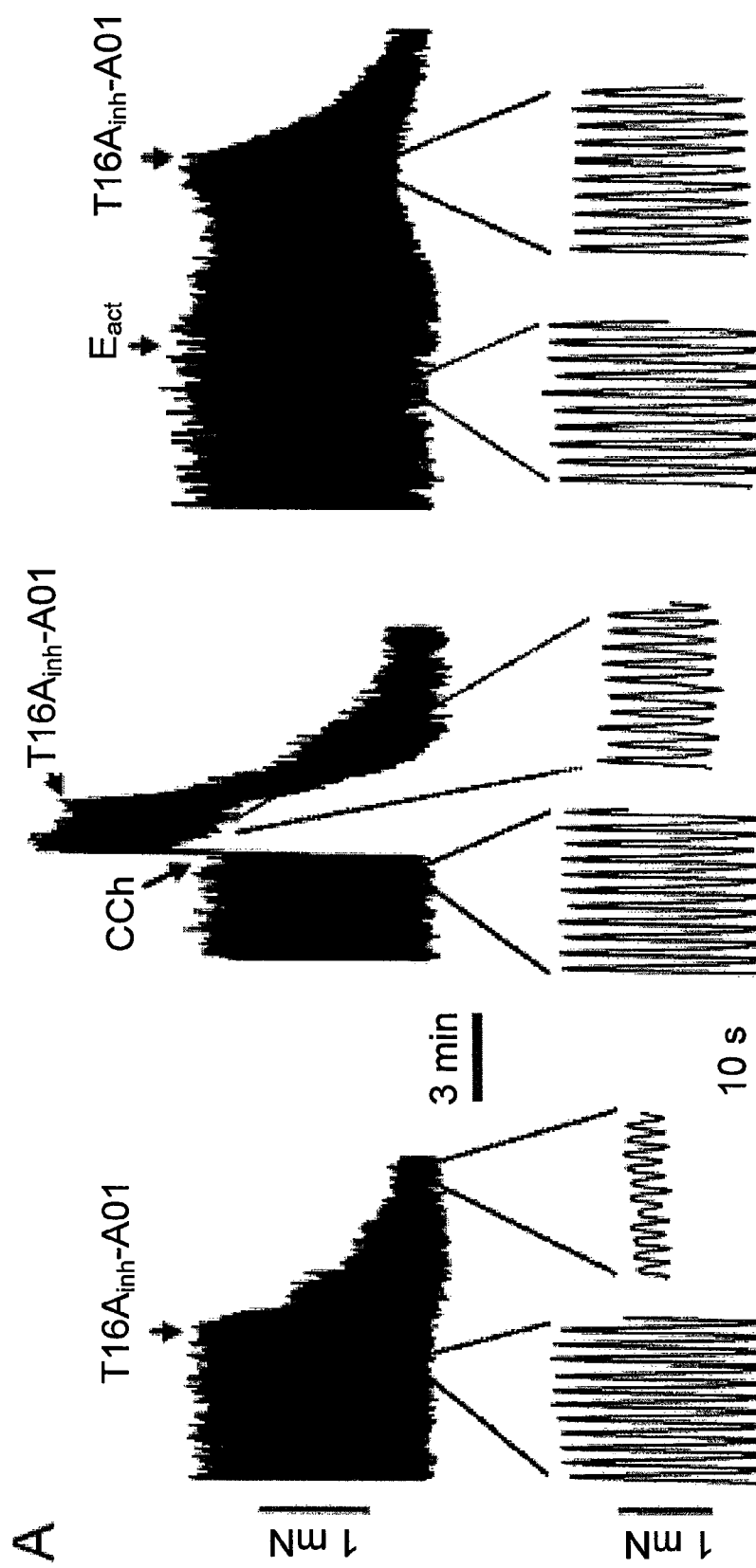
FIG. 8A-C. Intestinal smooth muscle contraction.
Figure 8B:
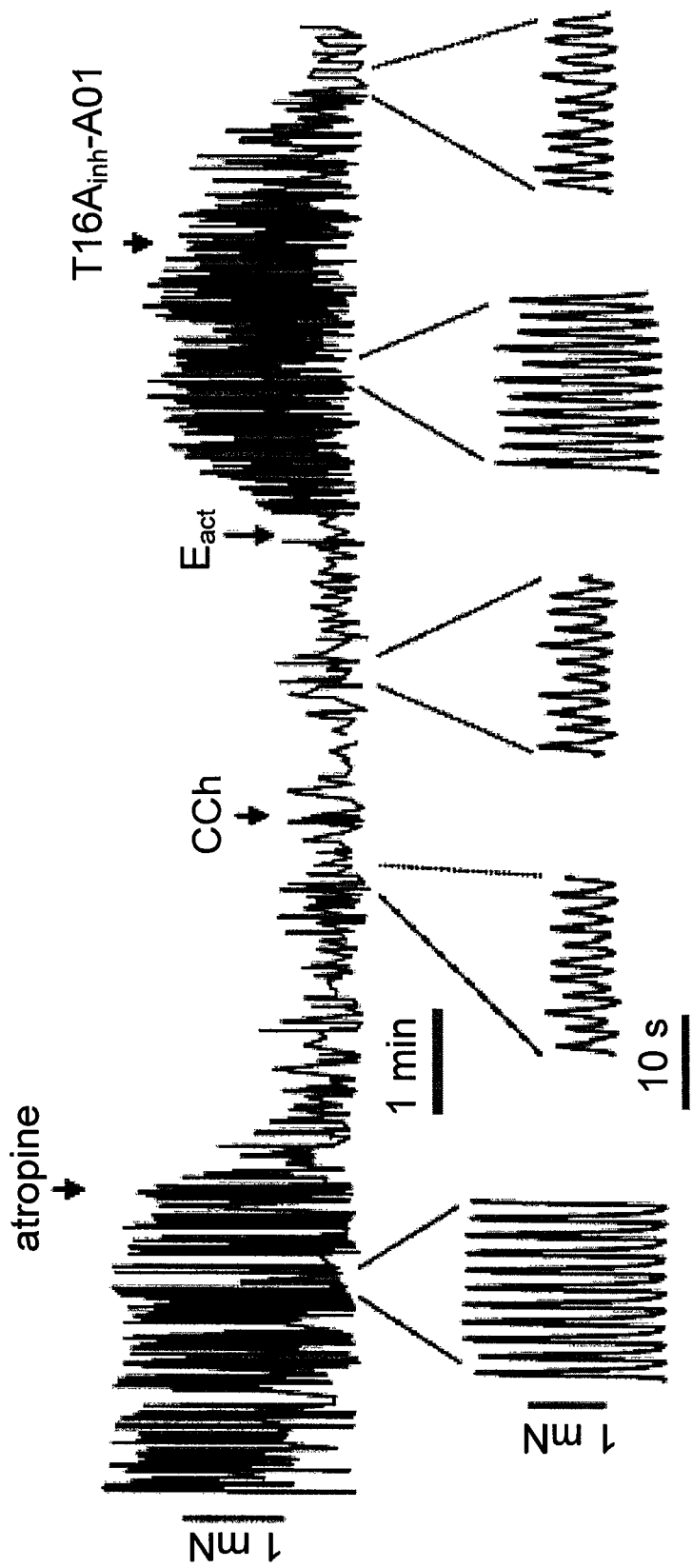
Figure 8C:
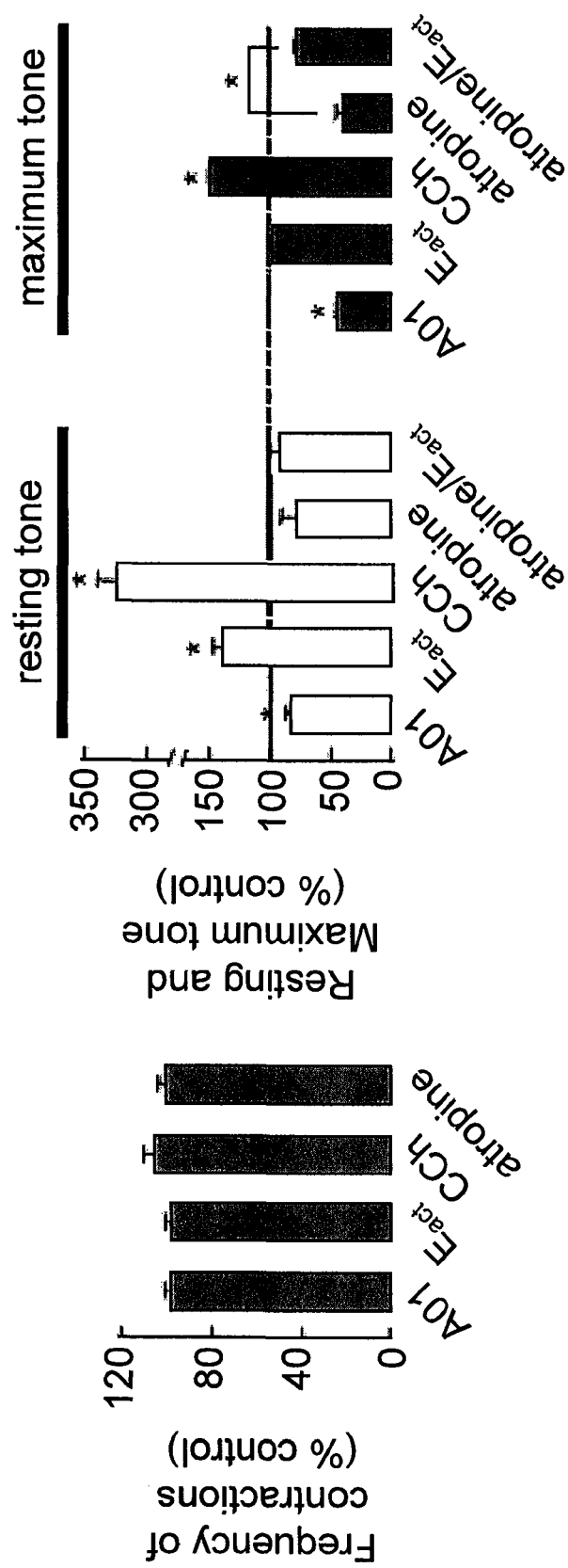

TMEM16A in expressed in the interstitial cells of Cajal, the pacemaker cells that control smooth muscle contraction dynamics in stomach and intestine (Huang et al., supra; Gomez-Pinilla et al. (2009) *Am. J. Physiol. Gastrointest. Liver Physiol.* 296, G1370-1381). The effect of $E_{act}$ on mouse ileal smooth muscle contraction was investigated using an ex vivo intestinal preparation. FIG. 8A shows considerable constitutive activity of mouse ileal muscle segments at baseline, with large, spontaneous intestinal contractions that were inhibited by T16A$_{inh}$-A01 (left panel). Resting and maximum tone were increased by carbachol, without change in contraction frequency (middle panel). $E_{act}$ produced a very small increase in resting but not maximum tone (right panel). Without wishing to be bound by theory, the constitutive TMEM16A activity in this ex vivo preparation could obscure $E_{act}$ activity. To reveal $E_{act}$ effects, atropine was first added to inhibit basal contractions. FIG. 8B shows that atropine prevented the carbachol effect, which is Ca²⁺-dependent, and revealed a large increase in contraction amplitude following $E_{act}$, whose action is Ca²⁺-independent. FIG. 8C summarizes data on contraction frequency, resting tone and maximal tone.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A pharmaceutical composition comprising a pharmaceutically acceptable excipient and a compound of structure (I):

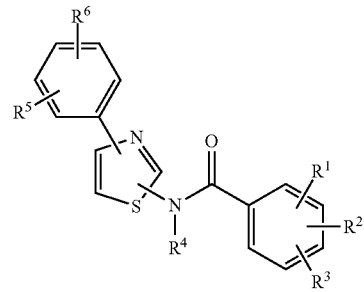

or a stereoisomer, tautomer, solvate, or pharmaceutically acceptable salt thereof, wherein
 $R^1$, $R^2$ and $R^3$ are each independently alkoxy;
 $R^4$ is heteroaralkyl, or heterocyclylalkyl; and
 $R^5$ and $R^6$ are each independently hydrogen, alkoxy or halo,
wherein the pharmaceutical composition is inhalable and the pharmaceutically acceptable excipient is not dimethyl sulfoxide (DMSO).

2. The pharmaceutical composition of claim 1, wherein the compound has one of the following structures (Ia), (Ib) or (Ic):

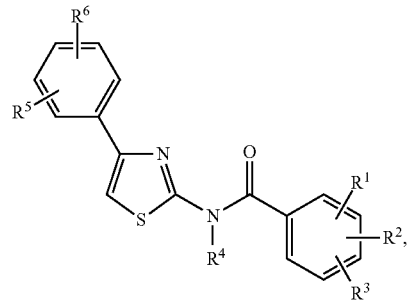

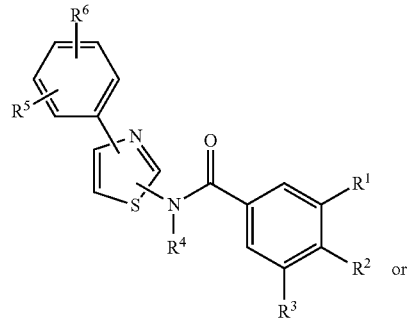

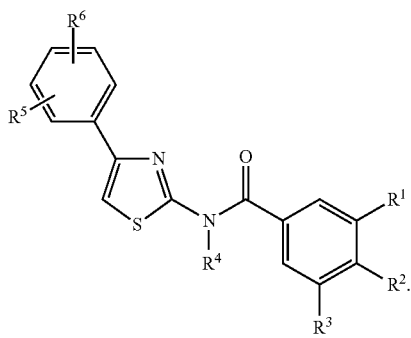

3. The pharmaceutical composition of claim 1, wherein at least one of $R^1$, $R^2$ or $R^3$ is methoxy.

4. The pharmaceutical composition of claim 1, wherein R⁴ is tetrahydrofuran-2-yl-methyl, furan-2-yl-methyl, tetrahydropyran-2-yl-methyl, pyrid-4-yl-methyl or pyrid-2-yl-methyl.

5. The pharmaceutical composition of claim 1, wherein at least one of R⁵ or R⁶ is hydrogen.

6. The pharmaceutical composition of claim 1, wherein at least one of R⁵ or R⁶ is methoxy, chloro, or fluoro.

7. The pharmaceutical composition of claim 1, wherein the compound has one of the following structures:

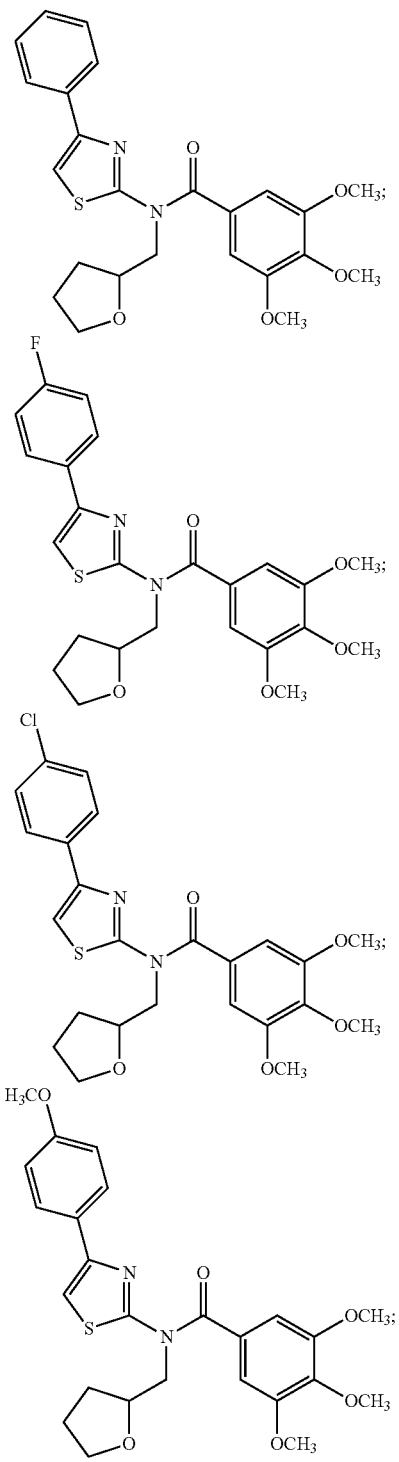

-continued

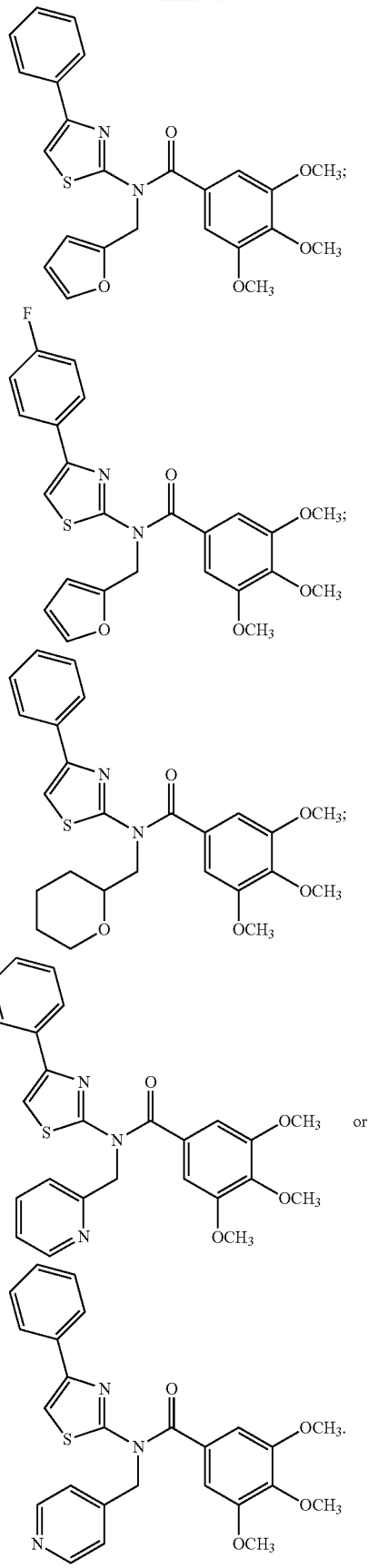

8. The pharmaceutical composition of claim 1, wherein the compound has one of the following structures:
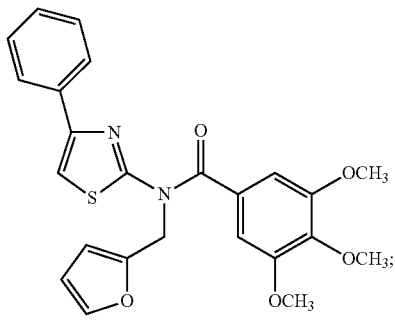
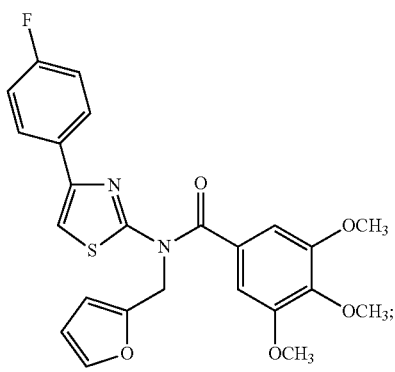
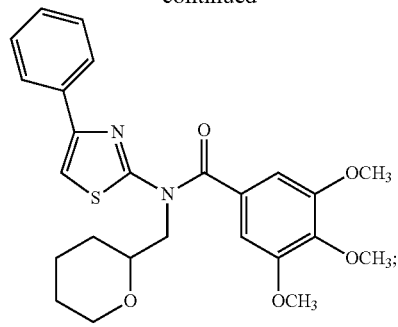
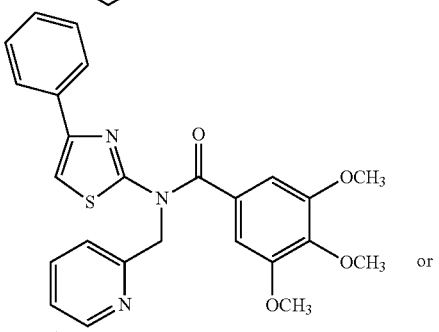 or
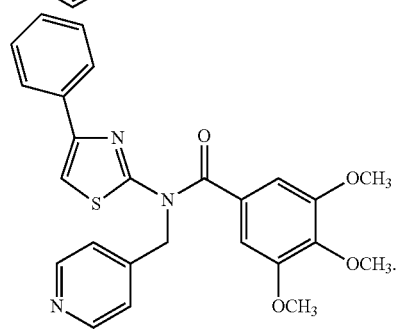
* * * * *

UNITED STATES PATENT AND TRADEMARK OFFICE
CERTIFICATE OF CORRECTION

PATENT NO. : 9,790,218 B2
APPLICATION NO. : 14/237079
DATED : October 17, 2017
INVENTOR(S) : Alan S. Verkman et al.

It is certified that error appears in the above-identified patent and that said Letters Patent is hereby corrected as shown below:

In the Specification

Column 1, Line 17:
Delete "and EY13574".

Signed and Sealed this
Third Day of December, 2024

Katherine Kelly Vidal
*Director of the United States Patent and Trademark Office*